(12) United States Patent
Ananthan et al.

(10) Patent No.: US 10,087,148 B2
(45) Date of Patent: Oct. 2, 2018

(54) QUINAZOLINES AS BIOGENIC AMINE TRANSPORT MODULATORS

(71) Applicants: Subramaniam Ananthan, Birmingham, AL (US); Richard B. Rothman, Baltimore, MD (US)

(72) Inventors: Subramaniam Ananthan, Birmingham, AL (US); Richard B. Rothman, Baltimore, MD (US)

(73) Assignees: THE UNITED STATES OF AMERICA AS REPRESENTED BY THE SECRETARY, DEPARTMENT OF HEALTH AND HUMAN SERVICES OFFICE OF TECHNOLOGY TRANSFER, NATIONAL INSTITUTE OF HEALTH, Washington, DC (US); SOUTHERN RESEARCH INSTITUTE, Birmingham, AL (US)

( * ) Notice: Subject to any disclaimer, the term of this patent is extended or adjusted under 35 U.S.C. 154(b) by 0 days.

(21) Appl. No.: 14/960,023

(22) Filed: Dec. 4, 2015

(65) Prior Publication Data

US 2016/0159751 A1 Jun. 9, 2016

Related U.S. Application Data

(60) Provisional application No. 62/087,998, filed on Dec. 5, 2014.

(51) Int. Cl.
| | | |
|---|---|---|
| *C07D 239/94* | (2006.01) | |
| *C07D 401/12* | (2006.01) | |
| *C07D 401/14* | (2006.01) | |
| *C07D 403/12* | (2006.01) | |

(52) U.S. Cl.
CPC ......... *C07D 239/94* (2013.01); *C07D 401/12* (2013.01); *C07D 401/14* (2013.01); *C07D 403/12* (2013.01)

(58) Field of Classification Search
CPC .. C07D 239/94; C07D 401/12; C07D 401/14; C07D 403/12
See application file for complete search history.

(56) References Cited

U.S. PATENT DOCUMENTS

| | | |
|---|---|---|
| 5,439,895 A | 8/1995 | Lee et al. |
| 7,410,975 B2 * | 8/2008 | Lipford ................ A61K 31/122 514/266.2 |
| 9,873,702 B2 | 1/2018 | Ananthan et al. |
| 2009/0137623 A1 | 5/2009 | Kumar et al. |
| 2011/0118289 A1 | 5/2011 | Giordani et al. |
| 2012/0232068 A1 | 9/2012 | Johnson et al. |

FOREIGN PATENT DOCUMENTS

| | | |
|---|---|---|
| WO | WO-2004/092196 A2 | 10/2004 |
| WO | WO 2006/071095 * | 7/2006 |
| WO | WO-2006/097441 A1 | 9/2006 |
| WO | WO-2009/001060 A2 | 12/2008 |
| WO | WO-2009/064388 A2 | 5/2009 |
| WO | WO-2010/056907 A2 | 5/2010 |
| WO | WO-2011/028741 A1 | 3/2011 |
| WO | WO-2011/072695 A1 | 6/2011 |
| WO | WO-2014/138518 A2 | 9/2014 |
| WO | WO-2016/090296 A1 | 6/2016 |
| WO | WO-2016/090299 A1 | 6/2016 |

OTHER PUBLICATIONS

Dass et al., Journal of Scientific & Industrial Research (1952), 11B, 461-3.*
Wawer et al., ChemMedChem (2009), 4(9), 1431-1438.*
Almarsson, et al., "Crystal engineering of the composition of pharmaceutical phases. Do pharmaceutical co-crystals represent a new path to improved medicines?," The Royal Society of Chemistry, Chem. Commun., 2004, pp. 1889-1896.
Ananthan et al., "Identification of a Novel Partial Inhibitor of Dopamine Transporter Among 4-Substituted 2-Phenylquinazolines," Bioorg. Med. Chem. Lett. 12, 2225-2228 (2002).
Basile et al., "Characterization of the Antinociceptive Actions of Bicifadine in Models of Acute, Persistent, and Chronic Pain ," J. Pharmacol. Exp. Ther. 321, 1208-1225 (2007).
Cao, et al., (2002) "Nitric oxide inhibits uptake of dopamine and N-methyl-4-phenylpyridinium (MPP+) but not release of MPP+ in rat C6 glioma cells expressing human dopamine transporter,". Br J Pharmacol 137:1155-1162.
Charney et al., "Monoamine Dysfunction and the Pathophysiology and Treatment of Depression," J. Clin. Psychiatry, 59, 11-14 (1998).
Delgado et al., "Depression: the case for a monoamine deficiency," J. Clin. Psychiatry, 61 (Suppl 6), 7-11 (2000).
Felten, et al., (2011) "Genetically determined dopamine availability predicts disposition for depression. Brain and behavior,"1:109-118.
Forrest, et al., (2011) "The structural basis of secondary active transport mechanisms," Biochim Biophys Acta 1807:167-188.
Gainetdinov RR and Caron MG (2003) "Monoamine transporters: from genes to behavior," Annu Rev Pharmacol Toxicol 43:261-284.
Gether U, et al., (2006) "Neurotransmitter transporters: molecular function of important drug targets," Trends Pharmacol Sci 27:375-383.

(Continued)

*Primary Examiner* — Rebecca L Anderson
(74) *Attorney, Agent, or Firm* — Ballard Spahr LLP

(57) ABSTRACT

The present disclosure relates to certain amine derivatives of fused bicyclic heterocycles that inhibit the amine reuptake function of the biogenic amine transporters, dopamine transporter (DAT), serotonin transporter (SERT) and norepinephrine transporter (NET). Compounds of the present disclosure are potent inhibitors of the reuptake of dopamine (DA), serotonin (5-hydroxytryptamine, 5-HT) and norepinephrine (NE) with full or partial maximal efficacy. The compounds with partial maximal efficacy in inhibiting reuptake of all three biogenic amines are herein referred to as partial triple uptake inhibitors (PTRIs). Compounds of the present disclosure are useful for treating depression, pain and substance abuse and relapse to substance abuse and addiction to substances such as cocaine, methamphetamine, nicotine and alcohol. This abstract is intended as a scanning tool for purposes of searching in the particular art and is not intended to be limiting of the present invention.

12 Claims, 4 Drawing Sheets

(56) References Cited

OTHER PUBLICATIONS

Greengard P (2001) "The neurobiology of slow synaptic transmission," Science 294:1024-1030.
Hache et al., "Monoaminergic Antidepressants in the Relief of Pain: Potential Therapeutic Utility of Triple Reuptake Inhibitors (TRIs)," Pharmaceuticals, 4, 285-342 (2011).
Hirschfeld, "History and Evolution of the Monoamine Hypothesis of Depression," J. Clin. Psychiatry, 61 (Suppl 6), 4-6 (2000).
Khoshbouei H, et al., (2003) "Amphetamine-induced dopamine efflux. A voltage-sensitive and intracellular Na+-dependent mechanism," J Biol Chem 278:12070-12077.
Kurian, et al., (2011) "Clinical and molecular characterisation of hereditary dopamine transporter deficiency syndrome: an observational cohort and experimental study," The Lancet Neurology 10:54-62.
Montague PR and Berns GS (2002) "Neural economics and the biological substrates of valuation," Neuron 36:265-284.
Nightingale, et al. (2005) "Studies of the Biogenic Amine Transporters. XI. Identification of a 1-[2-[Bis(4-fluorophenyl)methoxy]ethyl]-4-(3-phenylpropyl)piperazine (GBR12909) Analog That Allosterically Modulates the Serotonin Transporter," J Pharmacol Exp Ther 314:906-915.
Pariser et al., "Studies of the Biogenic Amine Transporters. 12. Identification of Novel Partial Inhibitors of Amphetamine-Induced Dopamine Release," J. Pharmacol. Exp. Ther. 326, 286-295 (2008).
Prins et al., "Triple reuptake inhibitors for treating subtypes of major depressive disorder: the monoamine hypothesis revisited," Expert Opin. Investig. Drugs 20, 1107-1130 (2011).
Ren et al., "Descending modulation in persistent pain: an update," Pain 100, 1-6 (2002).
Ressler et al., "Role of Serotonergic and Noradrenergic Systems in the Pathophysiology of Depression and Anxiety Disorders," Depress. Anxiety, 12 (Suppl 1), 2-19 (2000).
Rothman et al., "Studies of the Biogenic Amine Transporters. 13. Identification of "Agonist" and "Antagonist" Allosteric Modulators of Amphetamine-Induced Dopamine Release," J. Pharmacol. Exp. Ther. 329, 718-728 (2009).
Rothman et al., "Studies of the Biogenic Amine Transporters. VIII: Identification of a Novel Partial Inhibitor of Dopamine Uptake and Dopamine Transporter Binding,"Synapse, 43, 268-274 (2002).
Rothman, et al., (2001) "Amphetamine-type central nervous system stimulants release norepinephrine more potently than they release dopamine and serotonin," Synapse 39:32-41.
Rothman, et al., (2002) "Interaction of the anorectic medication, phendimetrazine, and its metabolites with monoamine transporters in rat brain," Eur J Pharmacol 447:51-57.
Rothman, et al., (2003) "In vitro characterization of ephedrine-related stereoisomers at biogenic amine transporters and the receptorome reveals selective actions as norepinephrine transporter substrates," J Pharmacol Exp Ther 307:138-145.
Rothman, et al., (2009) "Studies of the Biogenic Amine Transporters. 13. Identification of "Agonist" and "Antagonist" Allosteric Modulators of Amphetamine-Induced Dopamine Release," J Pharmacol Exp Ther. 392:718-728.
Salamone, et al., (2009) "Dopamine, behavioral economics, and effort," Frontiers in behavioral neuroscience 3:13.
Schmitt KC and Reith ME (2010) "Regulation of the dopamine transporter: aspects relevant to psychostimulant drugs of abuse," Ann NY Acad Sci 1187:316-340.
Schmitt, et al., (2013) "Nonclassical pharmacology of the dopamine transporter: atypical inhibitors, allosteric modulators, and partial substrates," The Journal of pharmacology and experimental therapeutics 346:2-10.
Sitte, et al., (1998) "Carrier-mediated release, transport rates, and charge transfer induced by amphetamine, tyramine, and dopamine in mammalian cells transfected with the human dopamine transporter," J Neurochem 71:1289-1297.
Tanda, et al., (2009) "Discovery of drugs to treat cocaine dependence: behavioral and neurochemical effects of atypical dopamine transport inhibitors," Adv Pharmacol 57:253-289.
Zhou et al., "Spinal serotonin receptors mediate descending facilitation of a nociceptive reflex from the nuclei reticularis gigantocellularis and gigantocellularis pars alpha in the rat," Brain Res. 550, 35-48 (1991).
Zhu et al., "Recombinant HIV-1TAT1-86 allosterically modulates dopamine transporter activity," Synapse, 65, 1251-54 (2011).
International Search Report and Written Opinion dated Feb. 11, 2016 for international application PCT/US2015/064075, filed on Dec. 4, 2015 (Applicant—Subtamaniam Ananthan) (14 pages).
International Search Report and Written Opinion dated Feb. 11, 2016 for international application PCT/US2015/064079, filed on Dec. 4, 2015 (Applicant—Subtamaniam Ananthan) (15 pages).
Non-Final Office Action dated Sep. 12, 2016 for U.S. Appl. No. 14/960,012, filed Dec. 4, 2015 (Applicant/Inventor—Subtamaniam Ananthan) (8 pages).
International Preliminary Report on Patentability dated Jun. 6, 2017 by the International Searching Authority for International Application No. PCT/US15/64075, which was filed on Dec. 4, 2015 and published as WO 2016/090296 on Jun. 9, 2016 (Applicant—Subramaniam Ananthan) (5 pages).
International Preliminary Report on Patentability dated Jun. 6, 2017 by the International Searching Authority for International Application No. PCT/US2015/064079, which was filed on Dec. 4, 2015 and published as WO 2016/090299 on Jun. 9, 2016 (Applicant—Subramaniam Ananthan) (5 pages).
Response to Non Final Rejection was filed on Feb. 7, 2017 with the USPTO for U.S. Appl. No. 14/960,012, filed Dec. 4, 2015 and published as US 2016-0159809 A1 on Jun. 9, 2016 (Inventor—Subramaniam Ananthan) (27 pages).
Final Rejection dated Jun. 5, 2017 by the USPTO for U.S. Appl. No. 14/960,012, filed Dec. 4, 2015 and published as US 2016-0159809 A1 on Jun. 9, 2016 (Inventor—Subramaniam Ananthan) (7 pages).
Response to Final Rejection was filed on Aug. 4, 2017 with the USPTO for U.S. Appl. No. 14/960,012, filed Dec. 4, 2015 and published as US 2016-0159809 A1 on Jun. 9, 2016 (Inventor—Subramaniam Ananthan) (12 pages).
Dener, et al., "Solid-Phase Synthesis of 2,4-Diaminoquinazoline Libraries". Journal of Combinatorial Chemistry 2001, vol. 3, No. 6, p. 590-597.
Notice of Allowance dated Sep. 6, 2017 by the USPTO office for U.S. Appl. No. 14/960,012, filed Dec. 4, 2015, and granted as U.S. Pat. No. 9,873,702 on Jan. 23, 2018 (Inventor-Subramaniam Ananthan)(9 pages).
Issue Notification dated Jan. 3, 2018 by the USPTO office for U.S. Appl. No. 14/960,012, filed Dec. 4, 2015, and granted as U.S. Pat. No. 9,873,702 on Jan. 23, 2018 (Inventor-Subramaniam Ananthan)(1 page).

* cited by examiner

QUINAZOLINES AS BIOGENIC AMINE TRANSPORT MODULATORS

CROSS-REFERENCE TO RELATED APPLICATIONS

This application claims the benefit of U.S. Provisional Application No. 62/087,998, filed on Dec. 5, 2014, which is incorporated herein fully by reference in its entirety.

STATEMENT REGARDING FEDERALLY SPONSORED RESEARCH

This invention was made with government support under grant number DA029962, awarded by the National Institute on Drug Abuse of the National Institutes of Health. The government has certain rights in the invention.

BACKGROUND

Dopamine, serotonin and norepinephrine are the three important neurotransmitters in the human brain. The extracellular concentration of these neurotransmitters are regulated by the membrane bound transporters, the dopamine transporter (DAT), serotonin transporter (SERT) and norepinephrine transporter (NET) by reuptake of the neurotransmitters from the neuronal cleft.

Dysfunction of the monoamine neurotransmitter function has been implicated in a number of CNS (Central Nervous System) diseases such as depression (see, e.g. Charney et al., *J. Clin. Psychiatry*, 59, 11-14 (1998); Delgado et al., *J. Clin. Psychiatry*, 61 (Suppl 6), 7-11 (2000); Ressler et al., *Depress. Anxiety*, 12 (Suppl 1), 2-19 (2000); Hirschfeld, *J. Clin. Psychiatry*, 61 (Suppl 6), 4-6 (2000); Prins et al., *Expert Opin. Investig. Drugs* 20, 1107-1130 (2011)). Selective serotonin reuptake inhibitors (SSRIs) and dual serotonin and norepinephrine reuptake inhibitors (SNRIs) have been widely used as antidepressants. The SSRIs and SNRIs however have slow onset of action and take several weeks of treatment before improvement in symptoms and some inhibitors cause side effects such as insomnia and sexual dysfunction. Moreover, a significant number of patients do not respond to currently available antidepressants.

Reduced levels of endogenous DA, 5-HT and NE have been suggested to play a role in acute and chronic pain at both the spinal and supraspinal levels (Ren et al., *Pain* 100, 1-6 (2002)). Reuptake inhibitors of these neurotransmitters consequently can attenuate pain by preventing presynaptic uptake of these neurotransmitters leading to sustained activation of the descending pain inhibitory pathways (Zhuo et al., *Brain Res.* 550, 35-48 (1991)). Pharmacological studies suggest that drugs simultaneously inhibiting reuptake of DA, 5-HT and NE may provide a broader spectrum of pain relief than single or dual acting agents (see Hache et al., *Pharmaceuticals*, 4, 285-342 (2011)). Indeed studies with the triple reuptake inhibitor bicifadine have shown that it is efficacious as an antinociceptive agent with antiallodynic and antihyperalgesic activity in acute, persistent and chronic pain models (Basile et al., *J. Pharmacol. Exp. Ther.* 321, 1208-1225 (2007)), and has been evaluated in clinical trials for the treatment of pain.

Despite the identification of weak partial inhibitors of the dopamine transporter in earlier studies (Ananthan et al., *Bioorg. Med. Chem. Lett.* 12, 2225-2228 (2002); Rothman et al., *Synapse*, 43, 268-274 (2002); Pariser et al., *J. Pharmacol. Exp. Ther.* 326, 286-295 (2008); Rothman et al., *J. Pharmacol. Exp. Ther.* 329, 718-728 (2009); Zhu et al., *Synapse*, 65, 1251 (2011)), the compounds that can effectively function as reuptake inhibitors of dopamine, serotonin, and norepinephrine have remained elusive. Thus, there remains a need for reuptake inhibitors selective for all three neurotransmitters. In addition to a favorable balance of inhibition potency among the three transporters, compounds that have submaximal efficacy in inhibiting the reuptake by allosteric or other mechanisms could provide therapeutic advantages over full efficacy inhibitors due to their ability to normalize the neurotransmitter levels depending upon the state of neurotransmitter.

SUMMARY

In accordance with the purpose(s) of the invention, as embodied and broadly described herein, the invention, in one aspect, relates to reuptake inhibitors of dopamine, serotonin, and norepinephrine and methods of making and using same.

The present disclosure relates to the synthesis and pharmacological profiles of the new triple reuptake inhibitors. Disclosed are compounds represented by formula (I):

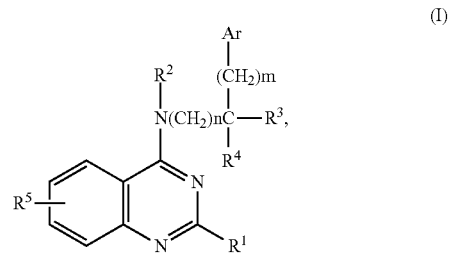

wherein n is 0, 1 or 2; m is 0, 1 or 2; $R^1$ is a substituted phenyl; $R^2$ is H or lower alkyl group; Ar is a phenyl or a heterocyclic group; $R^3$ is H, alkyl, aryl, aralkyl, heteroaryl or heteroarylalkyl; $R^4$ is H, alkyl, hydroxy, alkoxy, aryloxy, heteroaryloxy, amino, alkylamino or dialkylamino; $R^3$ and $R^4$ together form a carbocycle or heterocycle; $R^5$ is H, halogen, alkyl, aryl, hydroxy, alkoxy, aryloxy, amino, alkylamino or dialkylamino, pharmaceutically acceptable salts thereof, deuterated forms thereof, isomers thereof, solvates thereof, and mixtures thereof.

Also disclosed are pharmaceutical compositions comprising a pharmaceutically acceptable carrier and at least one of the above disclosed compounds of Formula I, pharmaceutically acceptable salts thereof, deuterated forms thereof, isomers thereof, solvates thereof, and mixtures thereof.

Also disclosed are methods for treating a patient suffering from depression, pain or addiction to substances such as cocaine, methamphetamine, nicotine and alcohol which comprising administering to said patient an effective amount of at least one of the above disclosed compounds of Formula I, pharmaceutically acceptable salts thereof, deuterated forms thereof, isomers thereof, solvates thereof or mixtures thereof.

Also disclosed are methods of inhibiting binding of a monoamine transporter ligand to a monoamine transporter such as dopamine transporter, serotonin transporter and norepinephrine transporter.

Also disclosed are methods of inhibiting the activity of at least one monoamine transporter such as dopamine transporter, serotonin transporter and norepinephrine transporter.

Also disclosed are methods of preparing compounds of Formula I. For example, the method can comprise reacting 2,4-dichloroquinazolines with an amine, followed by coupling with a heterocyclic compound.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BRIEF DESCRIPTION OF THE DRAWINGS

The accompanying figures, which are incorporated in and constitute a part of this specification, illustrate several aspects and together with the description serve to explain the principles of the invention.

Figure 1A:
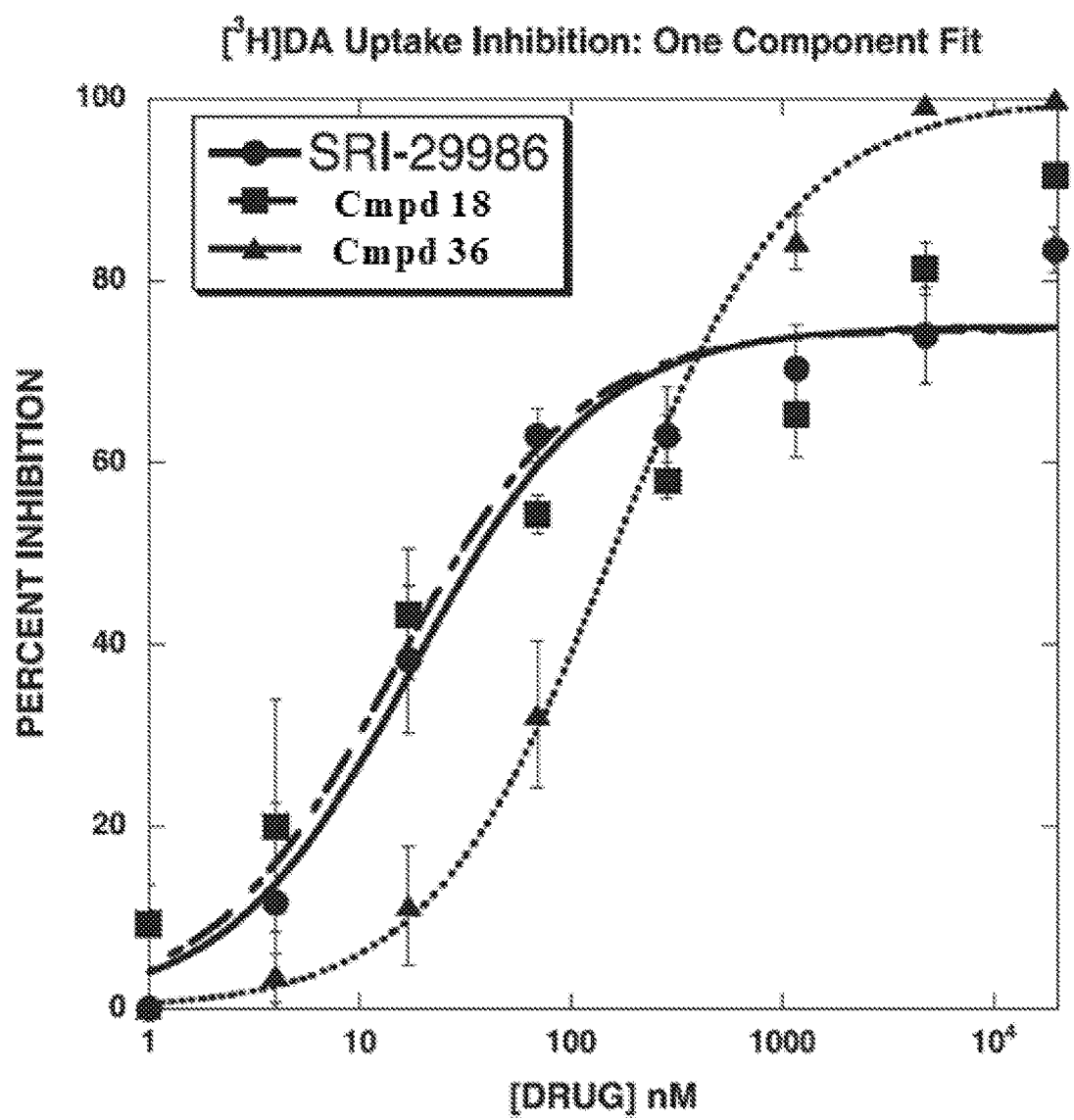
FIG. 1A and FIG. 1B show representative data illustrating that compound 18 partially inhibits [$^3$H]DA uptake and compound 36 fully inhibits [$^3$H]DA uptake when fit to a one-component (1A) or a two-component (1B) model.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

Listed below are definitions of various terms used to describe this disclosure. These definitions apply to the terms as they are used throughout this specification, unless otherwise limited in specific instances, either individually or as part of a larger group.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" mean that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorders prior to the administering step. In various aspects, the one or more disorders are a CNS disorder.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a CNS disorder prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "treating" refers to relieving the disease, disorder, or condition, i.e., causing regression of the disease, disorder, and/or condition. The term "preventing" refers to preventing a disease, disorder, or condition from occurring in a human or an animal that may be predisposed to the disease, disorder and/or condition, but has not yet been diagnosed as having it; and/or inhibiting the disease, disorder, or condition, i.e., arresting its development.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

The term "aryl" refers to monocyclic or bicyclic aromatic hydrocarbon groups having 6 to 12 carbon atoms in the ring portion, such as phenyl, naphthyl, biphenyl, and diphenyl groups, each of which may be substituted. Some typical substitutions for the aryl group include alkyl, alkenyl, alkynyl, cycloalkyl, halogen substituted alkyl, alkoxy, halogen substituted alkoxy, nitro, cyano, halogen, aryl, aryloxy, alkoxycarbonyl, hydroxy, protected hydroxyl, alkanoyl, sulfamoyl, alkylthio, alkylsulfonyl, hydroxysulfonyl, amino which may have groups such as alkyl, alkanoyl, cycloalkyl, aryl and aroyl groups, morpholinylcarbonylalkenyl, morpholinylcarbonylalkyl, pyrrolyl, prazolyl, dihydropyrazolyl, imiazolyl, triazolyl, pyridyl, pyrrolidinyl which may have oxo groups, morpholinyl, thiomorpholinyl, amidino, guanidino or heteocyclic groups.

The term "alkyl" refers to straight or branched chain unsubstituted hydrocarbon groups of 1 to 6 carbon atoms and even more typically 1 to 4 carbon atoms.

Examples of suitable alkyl groups include methyl, ethyl and propyl. Examples of branched alkyl groups include isopropyl and t-butyl.

The alkoxy group typically contains 1 to 6 carbon atoms. Suitable alkoxy groups typically contain 1-6 carbon atoms and include methoxy, ethoxy, propoxy and butoxy.

The term "alkenyl" refers to straight or branched chain unsubstituted hydrocarbon groups typically having 3 to 6 carbon atoms.

The term "aralkyl" or alkylaryl refers to an aryl group bonded directly through an alkyl group, such as benzyl or phenethyl.

The term "cycloalkyl" refers to cyclic hydrocarbon ring systems typically containing 3-9 carbon atoms, with typical examples being cyclopropyl, cyclobutyl, cyclopentyl, cyclohexyl, and cycloheptyl.

The term "cycloalkylalkyl" refers to alkyl substituted cyclic hydrocarbon ring system wherein the cyclic hydrocarbon typically contains 3-6 carbon atoms, a typical example being cyclopropylalkyl.

The term "heteroaryl" refers to 5 membered or 6 membered aromatic ring possessing one or more heteroatoms. Examples of heteroaryl groups are 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl, and each of which can optionally be substituted.

The term "heteroarylalky" refers to a heteroaryl group bonded directly through an alkyl group.

The term "heterocyclo" refers to an optionally substituted, saturated or unsaturated aromatic or nonaromatic cyclic group, for example, which is a 3 to 7 membered monocyclic ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. Examples of N-heterocyclo groups are pyridyl, pyrrolidinyl, piperidinyl, piperazinyl, pyrrolyl, pyrazolyl, pyrazinyl, pyrimidinyl, pyridazinyl, imidazoyl and imidazolidinyl, 1,2,3 triazole and 1,2,4 triazole. Examples of O-heterocyclic groups are furanyl and pyranyl. Examples of S-heterocyclic groups are thiopyran and thiophene. Examples of heterocyclic groups containing both N and O are morpholinyl, oxazole, and isooxazole. Example of heterocyclic groups containing both N and S are thiomorpholine, thiazole and isothiazole.

Examples of halo groups are Cl, F, Br and I. An example of a haloalkyl group is trifluoromethyl.

Compounds described herein may comprise atoms in both their natural isotopic abundance and in non-natural abundance. Thus, it is understood that the compounds of the present disclosure relate to all optical isomers and stereoisomers at the various possible atoms of the molecule, unless specified otherwise. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent. Thus, in various aspects, the deuterated forms contain heavy hydrogen including deuterium and/or tritium.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The compounds described in the invention can be present as a solvate. "Solvates" refers to the compound formed by the interaction of a solvent and a solute and includes hydrates. Solvates are usually crystalline solid adducts containing solvent molecules within the crystal structure, in either stoichiometric or nonstoichiometric proportions. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g., Almarasson, O., et al. (2004) *The Royal Society of Chemistry*, 1889-1896. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartrate, and the like.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

Compounds of the present disclosure are represented by formula (I).

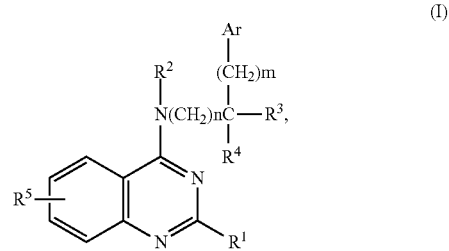

wherein n is 0, 1 or 2; m is 0, 1 or 2; $R^1$ is a substituted phenyl; $R^2$ is H or lower alkyl group; Ar is a phenyl or heterocyclic group; $R^3$ is H, alkyl, aryl, aralkyl, heteroaryl or heteroarylalkyl; $R^4$ is H, alkyl, hydroxy, alkoxy, aryloxy, heteroaryloxy, amino, alkylamino or dialkylamino; $R^3$ and $R^4$ together form a carbocycle or heterocycle; $R^5$ is H, halogen, alkyl, aryl, hydroxy, alkoxy, aryloxy, alkylamino or dialkylamino.

In one embodiment of the invention, n is: 0, 1 or 2; m is: 0, 1 or 2; $R^1$ is a phenyl group containing one or more substituents; $R^2$ is: H or lower alkyl group; Ar is: (a) a phenyl or substituted phenyl; or (b) a heteroaryl selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, each optionally substituted; $R^3$ is: (a) H, alkyl or cycloalkyl; (b) phenyl or substituted phenyl; or (c) heteroaryl selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, each optionally substituted; (d) aralkyl selected from benzyl, phenethyl, each optionally substituted; (e) heteroarylalkyl such as 2-pyridylmethyl, 3-pyridylmethyl, 4-pyridylmethyl, 2-thienylmethyl, 3-thienylmethyl, 2-furanymethyl, 3-furanymethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanyethyl, 3-furanylethyl, 2-pyrrolylethyl, 3-pyrrolylethyl, and heteroarylalkyls wherein heteroaryl contains two or more heteroatoms, each optionally substituted; $R^4$ is H, alkyl, hydroxy, alkoxy, aryloxy, heteroaryloxy, amino, alkylamino, or dialkylamino including a dialkylamine that is a nitrogen heterocycle such as aziridine, azetidine, pyrrolidine, piperidine, morpholine, piperazine, azepane, diazepane and azocane. These rings may contain additional substituents or groups such as alkyl, aryl, arylalkyl, heteroaryl, heteroarylalkyl, alkenyl, alkoxy, hydroxyl, protected hydroxyl, alkanoyl, carboxy, alkoxycarbonyl and carbamoyl. They also may have one or more oxo, thioxo, imino, methylene or additional atoms such as O, N, S, P, Se and Te, and be part of a fused bicyclic or polycyclic saturated or unsaturated system. $R^3$ and $R^4$ together form a carbocycle or heterocycle consisting of 3-9 atoms; $R^5$ is: (a) H, lower alkyl or aryl group; (b) halogen such as fluoro, chloro, bromo and iodo; or (c) hydroxyl, alkoxy, dialkylaminoalkoxy, aryloxy, amino, alkylamino and dialkylamino.

Preferred substituents in the phenyl, aryl and heteroaryl ring include: H, hydroxyl, chlorine, fluorine, bromine, trifluoromethyl, cyano, amino, carboxy, sulfo, sulfamoyl, unsubstituted or hydroxyl substituted C1-C6 alkyl, unsubstituted or hydroxyl substituted C1-C6 alkylthio, unsubstituted or substituted C2-C6 alkenyl, unsubstituted or substituted C2-C6 alkynyl, alkoxy, unsubstituted or substituted aryl or unsubstituted or substituted heteroaryl.

Preferred compounds according to the present disclosure are represented by the following formulae:

Compound having the formula (II):

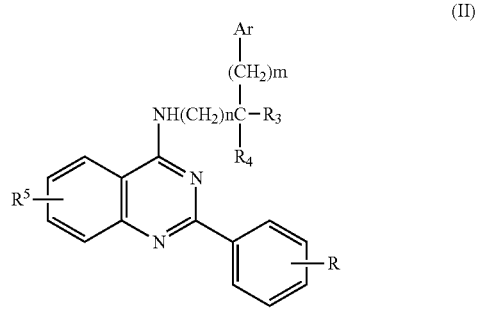

(II)

wherein $R^3$, $R^4$, $R^5$, Ar, n and m are as defined above, and R represents a lower alkyl, dialkylamino, or sulfonylamino group; pharmaceutically acceptable salts thereof, deuterated forms thereof, isomers thereof, solvates thereof, and mixtures thereof.

Compound having the formula (III):

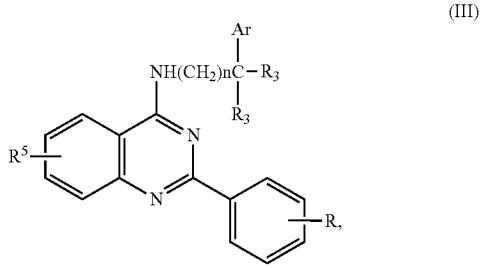

(III)

wherein $R^3$, $R^4$, $R^5$, Ar, and n and R represents a lower alkyl, dialkylamino, or sulfonylamino group; pharmaceutically acceptable salts thereof, deuterated forms thereof, isomers thereof, solvates thereof, and mixtures thereof.

Compound having the formula (IV):

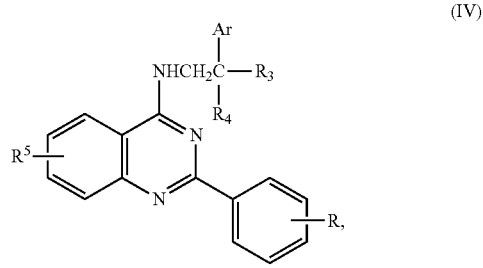

(IV)

wherein $R^3$, $R^4$, $R^5$, and Ar are as defined above and R represents a lower alkyl, dialkylamino, or sulfonylamino group pharmaceutically acceptable salts thereof, deuterated forms thereof, isomers thereof, solvates thereof, and mixtures thereof.

Compound having the formula (V):

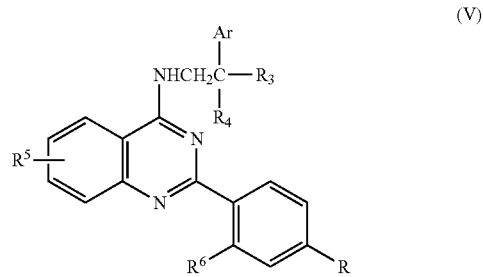

(V)

wherein $R^3$, $R^4$, $R^5$, and Ar are as defined above, R represents a lower alkyl, dialkylamino, or sulfonylamino group and $R^6$ is H, halogen, methyl, trifluoromethyl, lower alkyl or alkoxy group, pharmaceutically acceptable salts thereof, deuterated forms thereof, isomers thereof, solvates thereof, and mixtures thereof.

In one aspect, n is selected from 0, 1, and 2. In a still further aspect, n is selected from 0 and 1. In yet a further aspect, n is selected from 1 and 2. In an even further aspect, n is 0. In a still further aspect, n is 1. In yet a further aspect, n is 2.

In one aspect, m is selected from 0, 1, and 2. In a still further aspect, m is selected from 0 and 1. In yet a further aspect, m is selected from 1 and 2. In an even further aspect, m is 0. In a still further aspect, m is 1. In yet a further aspect, m is 2.

1. Structure

Suitable substituents are described herein below.

a. $R^1$ Groups

In one aspect, $R^1$ is a substituted phenyl.

In a further aspect, $R^1$ is phenyl substituted with 1, 2, or 3 groups independently selected from halogen, hydroxy, C1-C4 alkyl, C1-C4 alkoxy, aryloxy, —(C=O)(C1-C4 alkyl), —CO$_2$(C1-C4 alkyl), —SO$_2$H, —SO$_2$(C1-C4 alkyl), —NHSO$_2$(C1-C4 alkyl), —N(CH$_3$)SO$_2$(C1-C4 alkyl), —(C1-C4 alkyl)-C1-C4 alkoxy, —(C1-C4 alkyl)-(C1-C4)(C1-C4)-dialkylamino, aryl, heteroaryl, C1-C4 alkylamino, and (C1-C4)(C1-C4)dialkylamino. In a still further aspect, $R^1$ is phenyl substituted with 1 or 2 groups independently selected from halogen, hydroxy, C1-C4 alkyl, C1-C4 alkoxy, aryloxy, —(C=O)(C1-C4 alkyl), —CO₂(C1-C4 alkyl), —SO₂H, —SO₂(C1-C4 alkyl), —NHSO₂(C1-C4 alkyl), —N(CH₃)SO₂(C1-C4 alkyl), —(C1-C4 alkyl)-C1-C4 alkoxy, —(C1-C4 alkyl)-(C1-C4)(C1-C4)-dialkylamino, aryl, heteroaryl, C1-C4 alkylamino, and (C1-C4)(C1-C4) dialkylamino. In yet a further aspect, $R^1$ is phenyl monosubstituted with a group selected from halogen, hydroxy, C1-C4 alkyl, C1-C4 alkoxy, aryloxy, —(C=O)(C1-C4 alkyl), —CO₂(C1-C4 alkyl), —SO₂H, —SO₂(C1-C4 alkyl), —NHSO₂(C1-C4 alkyl), —N(CH₃)SO₂(C1-C4 alkyl), —(C1-C4 alkyl)-C1-C4 alkoxy, —(C1-C4 alkyl)-(C1-C4) (C1-C4)-dialkylamino, aryl, heteroaryl, C1-C4 alkylamino, and (C1-C4)(C1-C4)dialkylamino.

In a further aspect, $R^1$ is phenyl substituted with 1, 2, or 3 groups independently selected from halogen, —OH, —SH, —CN, —NO₂, —NH₂, C1-C4 alkyl, C1-C4 alkoxy, C1-C4 alkylamino, and (C1-C4)(C1-C4)dialkylamino. In a still further aspect, $R^1$ is phenyl substituted with 1 or 2 groups independently selected from halogen, —OH, —SH, —CN, —NO₂, —NH₂, C1-C4 alkyl, C1-C4 alkoxy, C1-C4 alkylamino, and (C1-C4)(C1-C4)dialkylamino. In yet a further aspect, $R^1$ is phenyl monosubstituted with a group selected from halogen, —OH, —SH, —CN, —NO₂, —NH₂, C1-C4 alkyl, C1-C4 alkoxy, C1-C4 alkylamino, and (C1-C4)(C1-C4)dialkylamino.

In a further aspect, $R^1$ is phenyl substituted with a group selected from —OH, —Cl, —F, —Br, —CF₃, —CN, —NH₂, —SO₂NH₂, —OSO₃H, —CO₂(C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or substituted heteroaryl. In a still further aspect, $R^1$ is phenyl substituted with a group selected from —OH, —Cl, —F, —Br, —CF₃, —CN, —NH₂, —SO₂NH₂, —OSO₃H, —CO₂(C1-C4 alkyl), C1-C6 alkyl, C1-C6 thioalkyl, C2-C6 alkenyl, C2-C6 alkynyl, C1-C6 hydroxy, C1-C6 alkoxy, C5-C6 aryl, and C3-C5 heteroaryl. In yet a further aspect, $R^1$ is phenyl substituted with a group selected from —OH, —Cl, —F, —Br, —CF₃, —CN, —NH₂, —SO₂NH₂, —OSO₃H, —CO₂(C1-C4 alkyl), C1-C4 alkyl, C1-C4 thioalkyl, C2-C4 alkenyl, C2-C4 alkynyl, C1-C4 hydroxy, C1-C4 alkoxy, C5-C6 aryl, and C3-C5 heteroaryl.

In a further aspect, $R^1$ is phenyl substituted with 1, 2, or 3 groups independently selected from —OH, —Cl, —F, —Br, —CF₃, —CN, —NH₂, —SO₂NH₂, —OSO₃H, —CO₂ (C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or substituted heteroaryl. In a still further aspect, $R^1$ is phenyl substituted with 1, 2, or 3 groups independently selected from —OH, —Cl, —F, —Br, —CF₃, —CN, —NH₂, —SO₂NH₂, —OSO₃H, —CO₂(C1-C4 alkyl), C1-C6 alkyl, C1-C6 thioalkyl, C2-C6 alkenyl, C2-C6 alkynyl, C1-C6 hydroxy, C1-C6 alkoxy, C5-C6 aryl, and C3-C5 heteroaryl. In yet a further aspect, $R^1$ is phenyl substituted with 1, 2, or 3 groups independently selected from —OH, —Cl, —F, —Br, —CF₃, —CN, —NH₂, —SO₂NH₂, —OSO₃H, —CO₂(C1-C4 alkyl), C1-C4 alkyl, C1-C4 thioalkyl, C2-C4 alkenyl, C2-C4 alkynyl, C1-C4 hydroxy, C1-C4 alkoxy, C5-C6 aryl, and C3-C5 heteroaryl.

In a further aspect, $R^1$ is phenyl substituted with 1 or 2 groups independently selected from —OH, —Cl, —F, —Br, —CF₃, —CN, —NH₂, —SO₂NH₂, —OSO₃H, —CO₂(C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or substituted heteroaryl. In a still further aspect, $R^1$ is phenyl monosubstituted with a group selected from —OH, —Cl, —F, —Br, —CF₃, —CN, —NH₂, —SO₂NH₂, —OSO₃H, —CO₂(C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or substituted heteroaryl.

b. $R^2$ Groups

In one aspect, $R^2$ is selected from hydrogen and a lower alkyl group. In a further aspect, $R^2$ is selected from hydrogen and C1-C4 alkyl. In a still further aspect, $R^2$ is hydrogen.

In a further aspect, $R^2$ is C1-C4 alkyl. In a still further aspect, $R^2$ is selected from n-propyl, i-propyl, ethyl, and methyl. In yet a further aspect, $R^2$ is selected from ethyl and methyl. In an even further aspect, $R^2$ is ethyl. In a still further aspect, $R^2$ is methyl.

In a further aspect, $R^2$ is selected from n-butyl, i-butyl, sec-butyl, t-butyl, n-propyl, propyl, ethyl, methyl, and hydrogen. In a still further aspect, $R^2$ is selected from n-propyl, propyl, ethyl, methyl, and hydrogen. In yet a further aspect, $R^2$ is selected from ethyl, methyl, and hydrogen. In an even further aspect, $R^2$ is selected from ethyl and hydrogen. In a still further aspect, $R^2$ is selected from methyl and hydrogen.

c. $R^3$ Groups

In one aspect, $R^3$ is selected from hydrogen, alkyl, cycloalkyl, heterocycloalkyl, aryl, aralkyl, heteroaryl, and heteroarylalkyl or $R^3$ and $R^4$ together form a carbocycle or heterocycle.

In a further aspect, $R^3$ is selected from hydrogen, C1-C8 alkyl, C3-C6 cycloalkyl, C2-C5 heterocycloalkyl, C5-C6 aryl, (C1-C4 alkyl)(C5-C6 aryl), C3-C5 heteroaryl, and (C1-C4)(C3-C5 heteroaryl). In a still further aspect, $R^3$ is selected from hydrogen, C1-C4 alkyl, C3-C6 cycloalkyl, C2-C5 heterocycloalkyl, C5-C6 aryl, (C1-C2 alkyl)(C5-C6 aryl), C3-C5 heteroaryl, and (C1-C2)(C3-C5 heteroaryl).

In a further aspect, $R^3$ is selected from hydrogen, alkyl, cycloalkyl, and heterocycloalkyl. In a still further aspect, $R^3$ is selected from hydrogen, C1-C8 alkyl, C3-C6 cycloalkyl, and C2-C5 heterocycloalkyl. In yet a further aspect, $R^3$ is selected from hydrogen, C1-C4 alkyl, C3-C6 cycloalkyl, and C2-C5 heterocycloalkyl. In an even further aspect, $R^3$ is selected from hydrogen, methyl, ethyl, n-propyl, i-propyl, cyclopropyl, cyclobutyl, cyclopentyl, oxiranyl, thiiranyl, aziridinyl, oxetanyl, thietanyl, azetidinyl, tetrahydrofuranyl, tetrahydrothiophenyl, pyrrolidinyl, tetrahydro-2H-pyranyl, tetrahydro-2H-thiopyranyl, piperidinyl, and morpholinyl. In a still further aspect, $R^3$ is selected from hydrogen, methyl, ethyl, cyclopropyl, cyclobutyl, oxiranyl, thiiranyl, aziridinyl, oxetanyl, thietanyl, azetidinyl, tetrahydrofuranyl, tetrahydrothiophenyl, pyrrolidinyl, and morpholinyl. In yet a further aspect, $R^3$ is selected from hydrogen, methyl, cyclopropyl, oxiranyl, thiiranyl, aziridinyl, oxetanyl, thietanyl, azetidinyl, and morpholinyl.

In a further aspect, $R^3$ is selected from hydrogen, alkyl, and cycloalkyl. In a still further aspect, $R^3$ is selected from hydrogen, C1-C8 alkyl, and C3-C6 cycloalkyl. In yet a further aspect, $R^3$ is selected from hydrogen, C1-C4 alkyl, and C3-C6 cycloalkyl. In an even further aspect, $R^3$ is selected from hydrogen, methyl, ethyl, n-propyl, i-propyl, cyclopropyl, cyclobutyl, and cyclopentyl. In a still further aspect, $R^3$ is selected from hydrogen, methyl, ethyl, cyclopropyl, and cyclobutyl. In yet a further aspect, $R^3$ is selected from hydrogen, methyl, and cyclopropyl.

In a further aspect, $R^3$ is selected from hydrogen and alkyl. In a still further aspect, $R^3$ is selected from hydrogen and C1-C8 alkyl. In yet a further aspect, $R^3$ is selected from hydrogen, methyl, ethyl, n-propyl, i-propyl, n-butyl, i-butyl, s-butyl, and t-butyl. In an even further aspect, $R^3$ is selected from hydrogen, methyl, ethyl, n-propyl, and i-propyl. In a still further aspect, $R^3$ is selected from hydrogen, methyl, and ethyl. In yet a further aspect, $R^3$ is selected from hydrogen and ethyl. In an even further aspect, $R^3$ is selected from hydrogen and methyl.

In a further aspect, $R^3$ is selected from cycloalkyl and heterocycloalkyl. In a still further aspect, $R^3$ is selected from C3-C6 cycloalkyl and C2-C5 heterocycloalkyl. In yet a further aspect, $R^3$ is selected from cyclopropyl, cyclobutyl, cyclopentyl, oxiranyl, thiiranyl, aziridinyl, oxetanyl, thietanyl, azetidinyl, tetrahydrofuranyl, tetrahydrothiophenyl, pyrrolidinyl, tetrahydro-2H-pyranyl, tetrahydro-2H-thiopyranyl, piperidinyl, and morpholinyl. In a still further aspect, $R^3$ is selected from cyclopropyl, cyclobutyl, oxiranyl, thiiranyl, aziridinyl, oxetanyl, thietanyl, azetidinyl, tetrahydrofuranyl, tetrahydrothiophenyl, pyrrolidinyl, and morpholinyl. In yet a further aspect, $R^3$ is selected from cyclopropyl, oxiranyl, thiiranyl, aziridinyl, and morpholinyl.

In a further aspect, $R^3$ is cycloalkyl. In a still further aspect, $R^3$ is C3-C6 cycloalkyl. In yet a further aspect, $R^3$ is selected from cyclopropyl, cyclobutyl, cyclopentyl, and cyclohexyl. In an even further aspect, $R^3$ is selected from cyclopropyl, cyclobutyl, and cyclohexyl. In a still further aspect, $R^3$ is selected from cyclopropyl and cyclohexyl. In yet a further aspect, $R^3$ is cyclohexyl.

In a further aspect, $R^3$ is heterocycloalkyl. In a still further aspect, $R^3$ is C2-C5 heterocycloalkyl. In yet a further aspect, $R^3$ is selected from oxiranyl, thiiranyl, aziridinyl, oxetanyl, thietanyl, azetidinyl, tetrahydrofuranyl, tetrahydrothiophenyl, pyrrolidinyl, tetrahydro-2H-pyranyl, tetrahydro-2H-thiopyranyl, piperidinyl, and morpholinyl. In a still further aspect, $R^3$ is selected from oxiranyl, thiiranyl, aziridinyl, oxetanyl, thietanyl, azetidinyl, tetrahydrofuranyl, tetrahydrothiophenyl, pyrrolidinyl, and morpholinyl. In yet a further aspect, $R^3$ is selected from oxiranyl, thiiranyl, aziridinyl, oxetanyl, thietanyl, azetidinyl, and morpholinyl. In an even further aspect, $R^3$ is selected from oxiranyl, thiiranyl, aziridinyl, and morpholinyl. In a still further aspect, $R^3$ is morpholinyl.

In a further aspect, $R^1$ is substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, $R^1$ is substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, $R^1$ is substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, $R^1$ is monosubstituted with a group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, $R^1$ is an unsubstituted.

In a further aspect, $R^3$ is selected from aryl, aralkyl, heteroaryl, and heteroarylalkyl. In a still further aspect, $R^3$ is selected from C5-C6 aryl, (C1-C4 alkyl)(C5-C6 aryl), C3-C5 heteroaryl, and (C1-C4)(C3-C5 heteroaryl). In yet a further aspect, $R^3$ is selected from C5-C6 aryl, (C1-C2 alkyl)(C5-C6 aryl), C3-C5 heteroaryl, and (C1-C2)(C3-C5 heteroaryl).

In a further aspect, $R^3$ is selected from aryl and aralkyl and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, $R^3$ is selected from C5-C6 aryl and (C1-C4 alkyl)(C5-C6 aryl) and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino.

In a further aspect, $R^3$ is aryl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, $R^3$ is aryl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, $R^3$ is aryl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, $R^3$ is unsubstituted aryl.

In a further aspect, $R^3$ is selected from phenyl and unsubstituted phenyl. In a still further aspect, $R^3$ is phenyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, $R^3$ is phenyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, $R^3$ is phenyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, $R^3$ is unsubstituted phenyl.

In a further aspect, $R^3$ is aralkyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, $R^3$ is aralkyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, $R^3$ is aralkyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, $R^3$ is unsubstituted aralkyl.

In a further aspect, $R^3$ is aralkyl selected from benzyl and phenethyl, each optionally substituted.

In a further aspect, $R^3$ is benzyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, $R^3$ is benzyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, $R^3$ is benzyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, R$^3$ is unsubstituted benzyl.

In a further aspect, R$^3$ is phenethyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, R$^3$ is phenethyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, R$^3$ is phenethyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, R$^3$ is unsubstituted phenethyl.

In a further aspect, R$^3$ is selected from heteroaryl and heteroarylalkyl and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, R$^3$ is selected from C3-C5 heteroaryl and (C1-C4)(C3-C5 heteroaryl) and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino.

In a further aspect, R$^3$ is heteroaryl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, R$^3$ is heteroaryl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, R$^3$ is heteroaryl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, R$^3$ is unsubstituted heteroaryl.

In a further aspect, R$^3$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and optionally substituted. In a still further aspect, R$^3$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, R$^3$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, R$^3$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, R$^3$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and unsubstituted.

In a further aspect, R$^3$ is pyridinyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, R$^3$ is pyridinyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, R$^3$ is pyridinyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, R$^3$ is unsubstituted pyridinyl.

In a further aspect, R$^3$ is pyrrolyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, R$^3$ is pyrrolyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, R$^3$ is pyrrolyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, R$^3$ is unsubstituted pyrrolyl.

In a further aspect, R$^3$ is heteroarylalkyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, R$^3$ is heteroarylalkyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, R$^3$ is heteroarylalkyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, R$^3$ is unsubstituted heteroarylalkyl.

In a further aspect, R$^3$ is a heteroarylalkyl, wherein the heteroaryl contains two or more heteroatoms and optionally substituted.

In a further aspect, R$^3$ is selected from 2-pyridylmethyl, 3-pyridylmethyl, 4-pyridylmethyl, 2-thienylmethyl, 3-thienylmethyl, 2-furanymethyl, 3-furanylmethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanyethyl, 3-furanyethyl, 2-pyrrolylethyl, 3-pyrrolylethyl and optionally substituted. In a still further aspect, R$^3$ is selected from 2-pyridylmethyl, 3-pyridylmethyl, 4-pyridylmethyl, 2-thienylmethyl, 3-thienylmethyl, 2-furanymethyl, 3-furanylmethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanyethyl, 3-furanyethyl, 2-pyrrolylethyl, 3-pyrrolylethyl and substituted with 0, 1, 2, or 3 groups independently selected from halogen, —OH, —SH, —CN, —NO$_2$, —NH₂, C1-C4 alkyl, C1-C4 alkoxy, C1-C4 alkylamino, and (C1-C4)(C1-C4)dialkylamino. In yet a further aspect, $R^3$ is selected from 2-pyridylmethyl, 3-pyridylmethyl, 4-pyridylmethyl, 2-thienylmethyl, 3-thienylmethyl, 2-furanymethyl, 3-furanylmethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanyethyl, 3-furanylethyl, 2-pyrrolylethyl, 3-pyrrolylethyl and substituted with 0, 1, or 2 groups independently selected from halogen, —OH, —SH, —CN, —NO₂, —NH₂, C1-C4 alkyl, C1-C4 alkoxy, C1-C4 alkylamino, and (C1-C4)(C1-C4)dialkylamino. In an even further aspect, $R^3$ is selected from 2-pyridylmethyl, 3-pyridylmethyl, 4-pyridylmethyl, 2-thienylmethyl, 3-thienylmethyl, 2-furanymethyl, 3-furanylmethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanyethyl, 3-furanylethyl, 2-pyrrolylethyl, 3-pyrrolylethyl and substituted with 0 or 1 group selected from halogen, —OH, —SH, —CN, —NO₂, —NH₂, C1-C4 alkyl, C1-C4 alkoxy, C1-C4 alkylamino, and (C1-C4)(C1-C4)dialkylamino. In a still further aspect, $R^3$ is selected from 2-pyridylmethyl, 3-pyridylmethyl, 4-pyridylmethyl, 2-thienylmethyl, 3-thienylmethyl, 2-furanymethyl, 3-furanylmethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanyethyl, 3-furanylethyl, 2-pyrrolylethyl, 3-pyrrolylethyl and unsubstituted.

In a further aspect, $R^3$ and $R^4$ together form a carbocycle or heterocycle. In a still further aspect, each of $R^3$ and $R^4$ together comprise a C3-C6 carbocycle or a C2-C5 heterocycle.

In a further aspect, each of $R^3$ and $R^4$ together comprise a C3-C6 carbocycle. In a still further aspect, each of $R^3$ and $R^4$ together comprise a C3-C6 carbocycle selected from cyclopropyl, cyclobutyl, and cyclopentyl. In yet a further aspect, each of $R^3$ and $R^4$ together comprise a C3-C6 carbocycle selected from cyclopropyl and cyclobutyl. In an even further aspect, each of $R^3$ and $R^4$ together comprise a cyclopropyl. In a still further aspect, each of $R^3$ and $R^4$ together comprise a cyclobutyl. In yet a further aspect, each of $R^3$ and $R^4$ together comprise a cyclopentyl. In an even further aspect, each of $R^3$ and $R^4$ together comprise a cyclohexyl.

In an even further aspect, each of $R^3$ and $R^4$ together comprise a C2-C5 carbocycle. In a still further aspect, each of $R^3$ and $R^4$ together comprise a C2-C5 carbocycle selected from oxiranyl, thiiranyl, aziridinyl, oxetanyl, thietanyl, azetidinyl, tetrahydrofuranyl, tetrahydrothiophenyl, pyrrolidinyl, tetrahydro-2H-pyranyl, tetrahydro-2H-thiopyranyl, and piperidinyl. In yet a further aspect, each of $R^3$ and $R^4$ together comprise a C2-C5 carbocycle selected from oxiranyl, thiiranyl, aziridinyl, oxetanyl, thietanyl, azetidinyl, tetrahydrofuranyl, tetrahydrothiophenyl, and pyrrolidinyl. In an even further aspect, each of $R^3$ and $R^4$ together comprise a C2-C5 carbocycle selected from oxiranyl, thiiranyl, aziridinyl, oxetanyl, thietanyl, and azetidinyl. In a still further aspect, each of $R^3$ and $R^4$ together comprise a C2-C5 carbocycle selected from oxiranyl, thiiranyl, and aziridinyl.

In a further aspect, $R^3$ and $R^4$ together form a carbocycle or heterocycle and are substituted with 0, 1, 2, or 3 groups independently selected from halogen, —OH, —SH, —CN, —NO₂, —NH₂, C1-C4 alkyl, C1-C4 alkoxy, C1-C4 alkylamino, and (C1-C4)(C1-C4)dialkylamino. In a still further aspect, $R^3$ and $R^4$ together form a carbocycle or heterocycle and are substituted with 0, 1, or 2 groups independently selected from halogen, —OH, —SH, —CN, —NO₂, —NH₂, C1-C4 alkyl, C1-C4 alkoxy, C1-C4 alkylamino, and (C1-C4)(C1-C4)dialkylamino. In yet a further aspect, $R^3$ and $R^4$ together form a carbocycle or heterocycle and are substituted with 0 or 1 group selected from halogen, —OH, —SH, —CN, —NO₂, —NH₂, C1-C4 alkyl, C1-C4 alkoxy, C1-C4 alkylamino, and (C1-C4)(C1-C4)dialkylamino. In an even further aspect, $R^3$ and $R^4$ together form a carbocycle or heterocycle and are unsubstituted.

In a further aspect, $R^3$ is substituted with a group selected from —OH, —Cl, —F, —Br, —CF₃, —CN, —NH₂, —SO₂NH₂, —OSO₃H, —CO₂(C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or substituted heteroaryl. In a still further aspect, $R^3$ is substituted with a group selected from —OH, —Cl, —F, —Br, —CF₃, —CN, —NH₂, —SO₂NH₂, —OSO₃H, —CO₂(C1-C4 alkyl), C1-C6 alkyl, C1-C6 thioalkyl, C2-C6 alkenyl, C2-C6 alkynyl, C1-C6 hydroxy, C1-C6 alkoxy, C5-C6 aryl, and C3-C5 heteroaryl. In yet a further aspect, $R^3$ is substituted with a group selected from —OH, —Cl, —F, —Br, —CF₃, —CN, —NH₂, —SO₂NH₂, —OSO₃H, —CO₂(C1-C4 alkyl), C1-C4 alkyl, C1-C4 thioalkyl, C2-C4 alkenyl, C2-C4 alkynyl, C1-C4 hydroxy, C1-C4 alkoxy, C5-C6 aryl, and C3-C5 heteroaryl.

In a further aspect, $R^3$ is substituted with 0, 1, 2, or 3 groups independently selected from —OH, —Cl, —F, —Br, —CF₃, —CN, —NH₂, —SO₂NH₂, —OSO₃H, —CO₂(C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or substituted heteroaryl. In a still further aspect, $R^3$ is substituted with 0, 1, 2, or 3 groups independently selected from —OH, —Cl, —F, —Br, —CF₃, —CN, —NH₂, —SO₂NH₂, —OSO₃H, —CO₂(C1-C4 alkyl), C1-C6 alkyl, C1-C6 thioalkyl, C2-C6 alkenyl, C2-C6 alkynyl, C1-C6 hydroxy, C1-C6 alkoxy, C5-C6 aryl, and C3-C5 heteroaryl. In yet a further aspect, $R^3$ is substituted with 0, 1, 2, or 3 groups independently selected from —OH, —Cl, —F, —Br, —CF₃, —CN, —NH₂, —SO₂NH₂, —OSO₃H, —CO₂(C1-C4 alkyl), C1-C4 alkyl, C1-C4 thioalkyl, C2-C4 alkenyl, C2-C4 alkynyl, C1-C4 hydroxy, C1-C4 alkoxy, C5-C6 aryl, and C3-C5 heteroaryl.

In a further aspect, $R^3$ is substituted with 0, 1, or 2 groups independently selected from —OH, —Cl, —F, —Br, —CF₃, —CN, —NH₂, —SO₂NH₂, —OSO₃H, —CO₂(C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or substituted heteroaryl. In a still further aspect, $R^3$ is substituted with 0 or 1 group selected from —OH, —Cl, —F, —Br, —CF₃, —CN, —NH₂, —SO₂NH₂, —OSO₃H, —CO₂(C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or substituted heteroaryl. In yet a further aspect, $R^3$ is monosubstituted with a group selected from —OH, —Cl, —F, —Br, —CF₃, —CN, —NH₂, —SO₂NH₂, —OSO₃H, —CO₂(C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or unsubstituted heteroaryl.

d. $R^4$ Groups

In one aspect, $R^4$ is selected from hydrogen, hydroxy, amino, alkyl, alkoxy, aryloxy, heteroaryloxy, alkylamino, and dialkylamino or $R^3$ and $R^4$ together form a carbocycle or heterocycle.

In a further aspect, $R^4$ is selected from hydrogen, hydroxy, amino, C1-C8 alkyl, C1-C8 alkoxy, C5-C6 aryloxy, C3-C5 heteroaryloxy, C1-C8 alkylamino, and (C1-C8)(C1-C8)dialkylamino. In a still further aspect, $R^4$ is selected from hydrogen, hydroxy, amino, C1-C4 alkyl, C1-C4 alkoxy, C5-C6 aryloxy, C3-C5 heteroaryloxy, C1-C4 alkylamino, and (C1-C4)(C1-C4)dialkylamino.

In a further aspect, $R^4$ is selected from hydrogen, hydroxy, amino, C1-C8 alkyl, C1-C8 alkoxy, C1-C8 alkylamino, and (C1-C8)(C1-C8)dialkylamino. In a still further aspect, $R^4$ is selected from hydrogen, hydroxy, amino, C1-C4 alkyl, C1-C4 alkoxy, C1-C4 alkylamino, and (C1-C4)(C1-C4) dialkylamino. In yet a further aspect, $R^4$ is selected from hydrogen, hydroxy, amino, methyl, ethyl, n-propyl, i-propyl, methoxy, ethoxy, n-propoxy, i-propoxy, —NHCH$_3$, —NHCH$_2$CH$_3$, —NHCH(CH$_3$)$_2$, —NH(CH$_2$)$_2$CH$_3$, —N(CH$_3$)$_2$, —N(CH$_2$CH$_3$)$_2$, —N(CH$_3$)(CH$_2$CH$_3$), —N(CH(CH$_3$)$_2$)$_2$, and —N((CH$_2$)$_2$CH$_3$)$_2$. In an even further aspect, $R^4$ is selected from hydrogen, hydroxy, amino, methyl, ethyl, methoxy, ethoxy, —NHCH$_3$, —NHCH$_2$CH$_3$, —N(CH$_3$)$_2$, —N(CH$_2$CH$_3$)$_2$, and —N(CH$_3$)(CH$_2$CH$_3$). In a still further aspect, $R^4$ is selected from hydrogen, hydroxy, amino, methyl, methoxy, —NHCH$_3$, and —N(CH$_3$)$_2$.

In a further aspect, $R^4$ is dialkylamino, wherein the dialkylamino is a nitrogen-containing heterocycle. In a still further aspect, the nitrogen-containing heterocycle further comprises one or more oxo, thioxo, imino, or methylene groups. In yet a further aspect, the nitrogen-containing heterocycle further comprises at least one atom selected from oxygen, nitrogen, sulphur, phosphorous, selenium, and tellurium. Examples of nitrogen-containing heterocycles include, but are not limited to, aziridine, azetidine, pyrrolidine, piperidine, morpholine, piperazine, azepane, diazepane and azocane. In an even further aspect, the nitrogen-containing heterocycle is optionally substituted with a group selected from alkyl, aryl, arylalkyl, heteroaryl, heteroarylalkyl, alkenyl, alkoxy, hydroxyl, protected hydroxyl, alkanoyl, carboxy, alkoxycarboyl, and carbamoyl.

In a further aspect, $R^4$ is selected from aryloxy and heteroaryloxy. In a still further aspect, $R^4$ is heteroaryloxy. In yet a further aspect, $R^4$ is aryloxy. In an even further aspect, $R^4$ is benzyloxy.

In a further aspect, $R^4$ is substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, $R^4$ is substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, $R^4$ is substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^4$ is unsubstituted.

e. $R^5$ Groups

In one aspect, $R^5$ is selected from hydrogen, halogen, hydroxy, amino, alkyl, aryl, alkoxy, dialkylaminoalkoxy, aryloxy, alkylamino, and dialkylamino. In a further aspect, $R^5$ is selected from hydrogen, halogen, hydroxy, amino, alkyl, aryl, alkoxy, aryloxy, alkylamino, and dialkylamino. In a still further aspect, $R^5$ is hydrogen.

In a further aspect, $R^5$ is selected from hydrogen, lower alkyl, and aryl. In a still further aspect, $R^5$ is selected from hydrogen, C1-C4 alkyl, and aryl. In yet a further aspect, $R^5$ is selected from hydrogen, methyl, ethyl, n-propyl, i-propyl, and phenyl. In an even further aspect, $R^5$ is selected from hydrogen, methyl, ethyl, and phenyl. In a still further aspect, $R^5$ is selected from hydrogen, methyl, and phenyl. In yet a further aspect, $R^5$ is selected from hydrogen and phenyl. In an even further aspect, $R^5$ is selected from hydrogen and methyl.

In a further aspect, $R^5$ is halogen. In a still further aspect, $R^5$ is selected from bromo, chloro, and fluoro. In yet a further aspect, $R^5$ is selected from chloro and fluoro. In an even further aspect, $R^5$ is iodo. In a still further aspect, $R^5$ is bromo. In yet a further aspect, $R^5$ is chloro. In an even further aspect, $R^5$ is fluoro.

In a further aspect, $R^5$ is selected from hydroxyl, amino, alkoxy, dialkylaminoalkoxy, aryloxy, alkylamino, and dialkylamino. In a still further aspect, $R^5$ is selected from hydroxyl, amino, C1-C4 alkoxy, (C1-C4)(C1-C4)dialkylamino-C1-C4 alkoxy, aryloxy, C1-C4 alkylamino, and (C1-C4)(C1-C4)dialkylamino. In yet a further aspect, $R^5$ is selected from hydroxyl, amino, methoxy, ethoxy, n-propoxy, i-propoxy, —OCH$_2$N(CH$_3$)$_2$, —O(CH$_2$)$_2$N(CH$_3$)$_2$, —OCH$_2$N(CH$_2$CH$_3$)$_2$, —O(CH$_2$)$_2$N(CH$_2$CH$_3$)$_2$, —NHCH$_3$, —NHCH$_2$CH$_3$, —NHCH(CH$_3$)$_2$, —NH(CH$_2$)$_2$CH$_3$, —N(CH$_3$)$_2$, —N(CH$_2$CH$_3$)$_2$, —N(CH$_3$)(CH$_2$CH$_3$), —N(CH(CH$_3$)$_2$)$_2$, and —N((CH$_2$)$_2$CH$_3$)$_2$. In an even further aspect, $R^5$ is selected from hydroxyl, amino, methoxy, ethoxy, —OCH$_2$N(CH$_3$)$_2$, —O(CH$_2$)$_2$N(CH$_3$)$_2$, —OCH$_2$N(CH$_2$CH$_3$)$_2$, —O(CH$_2$)$_2$N(CH$_2$CH$_3$)$_2$, —NHCH$_3$, —NHCH$_2$CH$_3$, —N(CH$_3$)$_2$, —N(CH$_2$CH$_3$)$_2$, and —N(CH$_3$)(CH$_2$CH$_3$). In a still further aspect, $R^5$ is selected from hydroxyl, amino, methoxy, —OCH$_2$N(CH$_3$)$_2$, —OCH$_2$N(CH$_2$CH$_3$)$_2$, —NHCH$_3$, —N(CH$_3$)$_2$, and —N(CH$_3$)(CH$_2$CH$_3$).

f. $R^6$ Groups

In one aspect, $R^6$ is selected from hydrogen, halogen, methyl, trifluoromethyl, lower alkyl, and alkoxy. In a still further aspect, $R^6$ is hydrogen.

In a further aspect, $R^6$ is selected from hydrogen, halogen, trifluoromethyl, C1-C4 alkyl, and C1-C4 alkoxy. In a still further aspect, $R^6$ is selected from hydrogen, —Cl, —F, —CF$_3$, methyl, ethyl, n-propyl, i-propyl, methoxy, ethoxy, n-propoxy, and i-propoxy. In yet a further aspect, $R^6$ is selected from hydrogen, —Cl, —F, —CF$_3$, methyl, ethyl, methoxy, and ethoxy. In an even further aspect, $R^6$ is selected from hydrogen, —Cl, —F, —CF$_3$, methyl, and methoxy.

In a further aspect, $R^6$ is selected from hydrogen and —CF$_3$. In a still further aspect, $R^6$ is —CF$_3$.

In a further aspect, $R^6$ is selected from hydrogen and C1-C4 alkoxy. In a still further aspect, $R^6$ is selected from hydrogen, methoxy, ethoxy, n-propoxy, and i-propoxy. In yet a further aspect, $R^6$ is selected from hydrogen, methoxy, and ethoxy. In an even further aspect, $R^6$ is selected from hydrogen and ethoxy. In a still further aspect, $R^6$ is selected from hydrogen and methoxy. In yet a further aspect, $R^6$ is methoxy.

In a further aspect, $R^6$ is selected from hydrogen and C1-C4 alkyl. In a still further aspect, $R^6$ is selected from hydrogen, methyl, ethyl, n-propyl, and i-propyl. In yet a further aspect, $R^6$ is selected from hydrogen, methyl, and ethyl. In an even further aspect, $R^6$ is selected from hydrogen and ethyl. In a still further aspect, $R^6$ is selected from hydrogen and methyl. In yet a further aspect, $R^6$ is methyl.

In a further aspect, $R^6$ is selected from hydrogen and halogen. In a still further aspect, $R^6$ is selected from hydrogen, —Br, —Cl, and —F. In yet a further aspect, $R^6$ is selected from hydrogen, —Cl, and —F. In a still further aspect, $R^6$ is selected from hydrogen and —Cl. In yet a further aspect, $R^6$ is selected from hydrogen and —F.

g. R Groups

In one aspect, R is selected from a lower alkyl, a dialkylamino, and a sulfonylamino. In a further aspect, R is selected from C1-C4 alkyl, (C1-C4)(C1-C4)dialkylamino, —NHSO$_2$(C1-C4 alkyl), and —N(CH$_3$)SO$_2$(C1-C4 alkyl).

In a further aspect, R is C1-C4 alkyl. In a still further aspect, R is selected from methyl, ethyl, n-propyl, and i-propyl. In yet a further aspect, R is selected from methyl and ethyl. In an even further aspect, R is ethyl. In a still further aspect, R is methyl.

In a further aspect, R is (C1-C4)(C1-C4)dialkylamino. In a still further aspect, R is selected from —N(CH$_3$)$_2$, —N(CH$_2$CH$_3$)$_2$, —N(CH$_3$)(CH$_2$CH$_3$), —N(CH(CH$_3$)$_2$)$_2$, and —N((CH$_2$)$_2$CH$_3$)$_2$. In yet a further aspect, R is selected from —N(CH$_3$)$_2$, —N(CH$_2$CH$_3$)$_2$, and —N(CH$_3$)(CH$_2$CH$_3$). In an even further aspect, R is selected from —N(CH$_3$)$_2$ and —N(CH$_2$CH$_3$)$_2$. In a still further aspect, R is —N(CH$_3$)$_2$.

In a further aspect, R is selected from —NHSO$_2$(C1-C4 alkyl) and —N(CH$_3$)SO$_2$(C1-C4 alkyl). In a still further aspect, R is selected from —NHSO$_2$CH$_3$, —NHSO$_2$CH$_2$CH$_3$, —NHSO$_2$CH(CH$_3$)$_2$, —NHSO$_2$(CH$_2$)$_2$CH$_3$, —N(CH$_3$)SO$_2$CH$_3$, —N(CH$_3$)SO$_2$CH$_2$CH$_3$, —N(CH$_3$)SO$_2$CH(CH$_3$)$_2$, and —N(CH$_3$)SO$_2$(CH$_2$)$_2$CH$_3$. In yet a further aspect, R is selected from —NHSO$_2$CH$_3$, —NHSO$_2$CH$_2$CH$_3$, —N(CH$_3$)SO$_2$CH$_3$, and —N(CH$_3$)SO$_2$CH$_2$CH$_3$. In an even further aspect, R is selected from —NHSO$_2$CH$_3$ and —N(CH$_3$)SO$_2$CH$_3$. In a still further aspect, R is —N(CH$_3$)SO$_2$CH$_3$. In yet a further aspect, R is —NHSO$_2$CH$_3$.

h. Ar Groups

In one aspect, Ar is selected from phenyl and heterocycle.

In a further aspect, Ar is phenyl or substituted phenyl. In a still further aspect, Ar is phenyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, Ar is phenyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, Ar is phenyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, Ar is unsubstituted phenyl.

In a further aspect, Ar is heterocycle and optionally substituted. In a still further aspect, Ar is heterocycle substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, Ar is heterocycle substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, Ar is heterocycle substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, Ar is unsubstituted heterocycle.

In a further aspect, Ar is heteroaryl and optionally substituted. In a still further aspect, Ar is heteroaryl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, Ar is heteroaryl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, Ar is heteroaryl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, Ar is unsubstituted heteroaryl.

In a further aspect, Ar is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and optionally substituted. In a still further aspect, Ar is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In yet a further aspect, Ar is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In an even further aspect, Ar is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4)dialkylamino. In a still further aspect, Ar is Ar is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and unsubstituted.

In a further aspect, Ar is substituted with a group selected from —OH, —Cl, —F, —Br, —CF$_3$, —CN, —NH$_2$, —SO$_2$NH$_2$, —OSO$_3$H, —CO$_2$(C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or substituted heteroaryl. In a still further aspect, Ar is substituted with a group selected from —OH, —Cl, —F, —Br, —CF$_3$, —CN, —NH$_2$, —SO$_2$NH$_2$, —OSO₃H, —CO₂(C1-C4 alkyl), C1-C6 alkyl, C1-C6 thioalkyl, C2-C6 alkenyl, C2-C6 alkynyl, C1-C6 hydroxy, C1-C6 alkoxy, C5-C6 aryl, and C3-C5 heteroaryl. In yet a further aspect, Ar is substituted with a group selected from —OH, —Cl, —F, —Br, —CF₃, —CN, —NH₂, —SO₂NH₂, —OSO₃H, —CO₂(C1-C4 alkyl), C1-C4 alkyl, C1-C4 thioalkyl, C2-C4 alkenyl, C2-C4 alkynyl, C1-C4 hydroxy, C1-C4 alkoxy, C5-C6 aryl, and C3-C5 heteroaryl.

In a further aspect, Ar is substituted with 0, 1, 2, or 3 groups independently selected from —OH, —Cl, —F, —Br, —CF₃, —CN, —NH₂, —SO₂NH₂, —OSO₃H, —CO₂(C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or substituted heteroaryl. In a still further aspect, Ar is substituted with 0, 1, 2, or 3 groups independently selected from —OH, —Cl, —F, —Br, —CF₃, —CN, —NH₂, —SO₂NH₂, —OSO₃H, —CO₂(C1-C4 alkyl), C1-C6 alkyl, C1-C6 thioalkyl, C2-C6 alkenyl, C2-C6 alkynyl, C1-C6 hydroxy, C1-C6 alkoxy, C5-C6 aryl, and C3-C5 heteroaryl. In yet a further aspect, Ar is substituted with 0, 1, 2, or 3 groups independently selected from —OH, —Cl, —F, —Br, —CF₃, —CN, —NH₂, —SO₂NH₂, —OSO₃H, —CO₂(C1-C4 alkyl), C1-C4 alkyl, C1-C4 thioalkyl, C2-C4 alkenyl, C2-C4 alkynyl, C1-C4 hydroxy, C1-C4 alkoxy, C5-C6 aryl, and C3-C5 heteroaryl.

In a further aspect, Ar is substituted with 0, 1, or 2 groups independently selected from —OH, —Cl, —F, —Br, —CF₃, —CN, —NH₂, —SO₂NH₂, —OSO₃H, —CO₂(C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or substituted heteroaryl. In a still further aspect, Ar is substituted with 0 or 1 group selected from —OH, —Cl, —F, —Br, —CF₃, —CN, —NH₂, —SO₂NH₂, —OSO₃H, —CO₂(C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or substituted heteroaryl. In yet a further aspect, Ar is monosubstituted with a group selected from —OH, —Cl, —F, —Br, —CF₃, —CN, —NH₂, —SO₂NH₂, —OSO₃H, —CO₂(C1-C4 alkyl), unsubstituted or hydroxy substituted C1-C6 alkyl, unsubstituted or hydroxy substituted C1-C6 thioalkyl, unsubstituted or substituted C2-C6 alkenyl, unsubstituted or unsubstituted C2-C6 alkynyl, alkoxy, unsubstituted or substituted aryl, and unsubstituted or substituted heteroaryl.

2. Example Compounds

Representative compounds according to the present disclosure are shown in Table 1.

TABLE 1

| No. | Structure | Name | M + H |
|---|---|---|---|
| 1 | 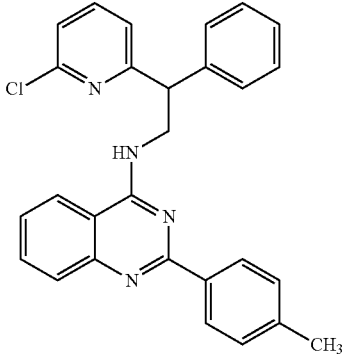 [SMILES: Cc1ccc(-c2nc(NCC(c3ccccc3)c3cccc(Cl)n3)c3ccccc3n2)cc1] | N-(2-(6-chloropyridin-2-yl)-2-phenylethyl)-2-(p-tolyl)quinazolin-4-amine | 451 |
| 2 | 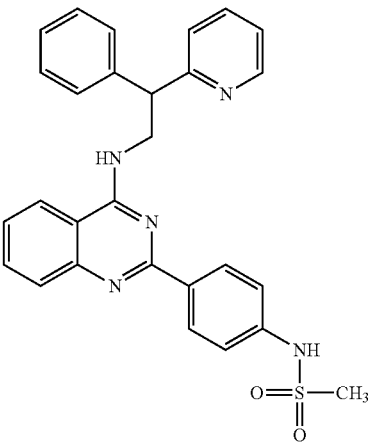 [SMILES: CS(=O)(=O)Nc1ccc(-c2nc(NCC(c3ccccc3)c3ccccn3)c3ccccc3n2)cc1] | N-(4-(4-((2-phenyl-2-(pyridin-2-yl)ethyl)amino)quinazolin-2-yl)phenyl)methanesulfonamide | 496 |

TABLE 1-continued

| No. | Structure | Name | M + H |
|---|---|---|---|
| 3 | 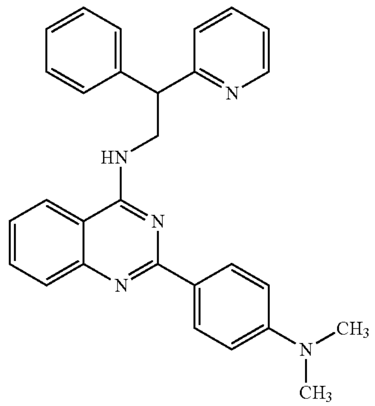 [SMILES: CN(C)c1ccc(-c2nc(NCC(c3ccccc3)c3ccccn3)c3ccccc3n2)cc1] | 2-(4-(dimethylamino)phenyl)-N-(2-phenyl-2-(pyridin-2-yl)ethyl)quinazolin-4-amine | 446 |
| 4 | 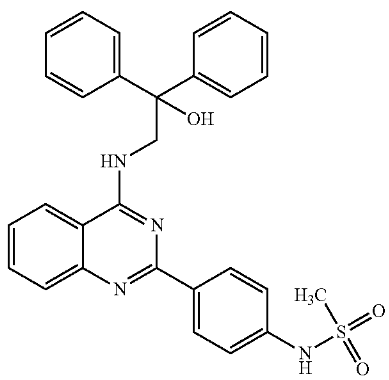 [SMILES: CS(=O)(=O)Nc1ccc(-c2nc(NCC(O)(c3ccccc3)c3ccccc3)c3ccccc3n2)cc1] | N-(4-(4-((2-hydroxy-2,2-diphenylethyl)amino)quinazolin-2-yl)phenyl)methanesulfonamide | 511 |
| 5 | 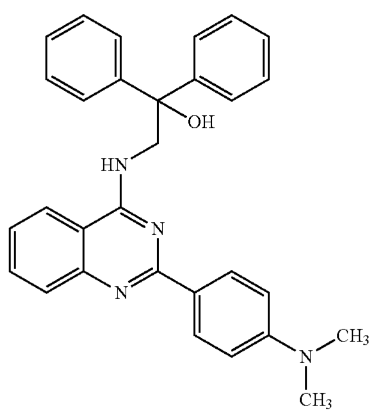 [SMILES: CN(C)c1ccc(-c2nc(NCC(O)(c3ccccc3)c3ccccc3)c3ccccc3n2)cc1] | 2-((2-(4-(dimethylamino)phenyl)quinazolin-4-yl)amino)-1,1-diphenylethanol | 461 |
| 6 | 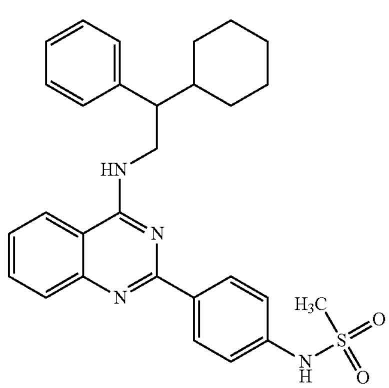 [SMILES: CS(=O)(=O)Nc1ccc(-c2nc(NCC(c3ccccc3)C3CCCCC3)c3ccccc3n2)cc1] | N-(4-(4-((2-cyclohexyl-2-phenylethyl)amino)quinazolin-2-yl)phenyl)methanesulfonamide | 501 |

TABLE 1-continued

| No. | Structure | Name | M + H |
|---|---|---|---|
| 7 | 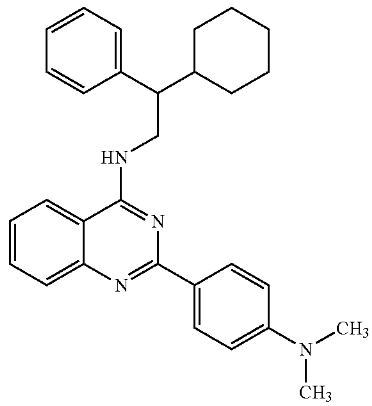 [SMILES: CN(C)c1ccc(-c2nc(NCC(c3ccccc3)C3CCCCC3)c3ccccc3n2)cc1] | N-(2-cyclohexyl-2-phenylethyl)-2-(4-(dimethylamino)phenyl)quinazolin-4-amine | 451 |
| 8 | 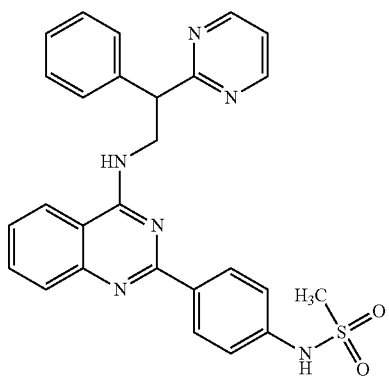 [SMILES: CS(=O)(=O)Nc1ccc(-c2nc(NCC(c3ccccc3)c3ncccn3)c3ccccc3n2)cc1] | N-(4-(4-((2-phenyl-2-(pyrimidin-2-yl)ethyl)amino)quinazolin-2-yl)phenyl)methanesulfonamide | 497 |
| 9 | 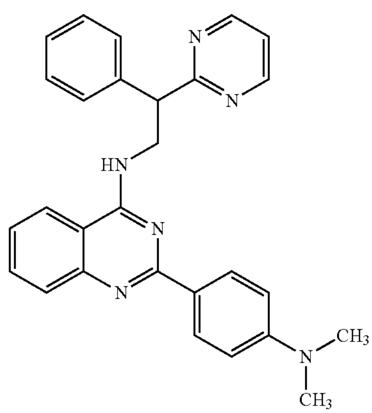 [SMILES: CN(C)c1ccc(-c2nc(NCC(c3ccccc3)c3ncccn3)c3ccccc3n2)cc1] | 2-(4-(dimethylamino)phenyl)-N-(2-phenyl-2-(pyrimidin-2-yl)ethyl)quinazolin-4-amine | 447 |
| 10 | 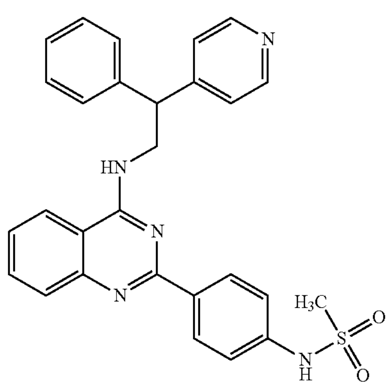 [SMILES: CS(=O)(=O)Nc1ccc(-c2nc(NCC(c3ccccc3)c3ccncc3)c3ccccc3n2)cc1] | N-(4-(4-((2-phenyl-2-(pyridin-4-yl)ethyl)amino)quinazolin-2-yl)phenyl)methanesulfonamide | 496 |

TABLE 1-continued

| No. | Structure | Name | M + H |
|---|---|---|---|
| 11 | 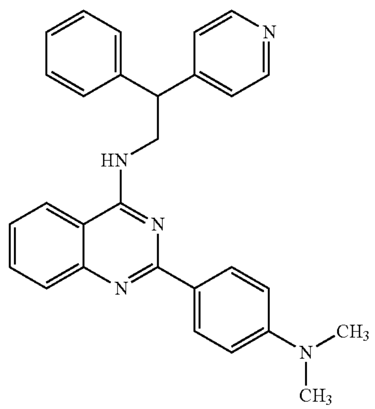 [SMILES: CN(C)c1ccc(-c2nc(NCC(c3ccccc3)c3ccncc3)c3ccccc3n2)cc1] | 2-(4-dimethylamino)phenyl)-N-(2-phenyl-2-(pyridin-4-yl)ethyl)quinazolin-4-amine | 446 |
| 12 | 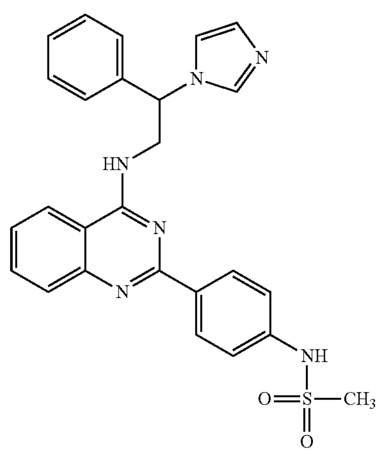 [SMILES: CS(=O)(=O)Nc1ccc(-c2nc(NCC(c3ccccc3)n3ccnc3)c3ccccc3n2)cc1] | N-(4-(4-((2-(1H-imidazol-1-yl)-2-phenylethyl)amino)quinazolin-2-yl)phenyl)methanesulfonamide | 485 |
| 13 | 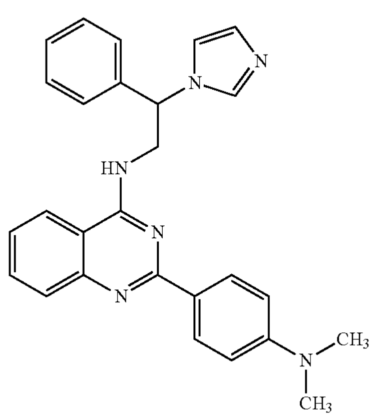 [SMILES: CN(C)c1ccc(-c2nc(NCC(c3ccccc3)n3ccnc3)c3ccccc3n2)cc1] | N-(2-(1H-imidazol-1-yl)-2-phenylethyl)-2-(4-(dimethylamino)phenyl)quinazolin-4-amine | 435 |

TABLE 1-continued

| No. | Structure | Name | M + H |
|---|---|---|---|
| 14 | 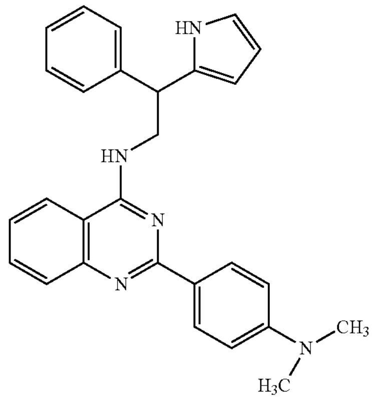 [SMILES: CN(C)c1ccc(-c2nc(NCC(c3ccccc3)c3ccc[nH]3)c3ccccc3n2)cc1] | 2-(4-(dimethylamino)phenyl)-N-(2-phenyl-2-(1H-pyrrol-2-yl)ethyl)quinazolin-4-amine | 434 |
| 15 | 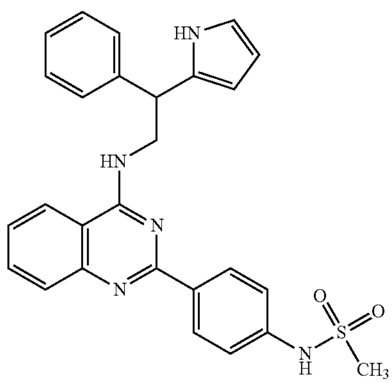 [SMILES: CS(=O)(=O)Nc1ccc(-c2nc(NCC(c3ccccc3)c3ccc[nH]3)c3ccccc3n2)cc1] | N-(4-(4-((2-phenyl-2-(1H-pyrrol-2-yl)ethyl)amino)quinazolin-2-yl)phenyl)methanesulfonamide | 484 |
| 16 | 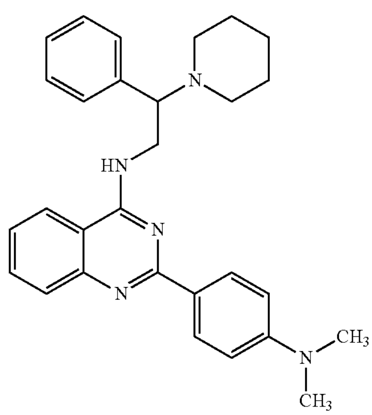 [SMILES: CN(C)c1ccc(-c2nc(NCC(c3ccccc3)N3CCCCC3)c3ccccc3n2)cc1] | 2-(4-(dimethylamino)phenyl)-N-(2-phenyl-2-(piperidin-1-yl)ethyl)quinazolin-4-amine | 452 |

TABLE 1-continued

| No. | Structure | Name | M + H |
|---|---|---|---|
| 17 | 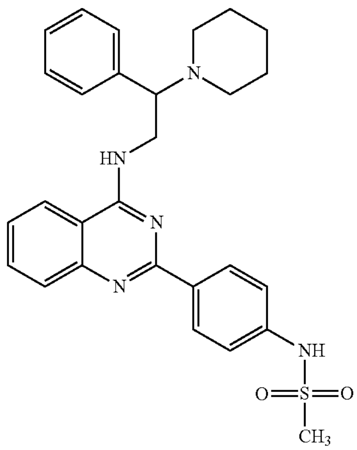 [SMILES: CS(=O)(=O)Nc1ccc(-c2nc(NCC(c3ccccc3)N3CCCCC3)c3ccccc3n2)cc1] | N-(4-(4-((2-phenyl-2-(piperidin-1-yl)ethyl)amino)quinazolin-2-yl)phenyl)methanesulfonamide | 502 |
| 18 | 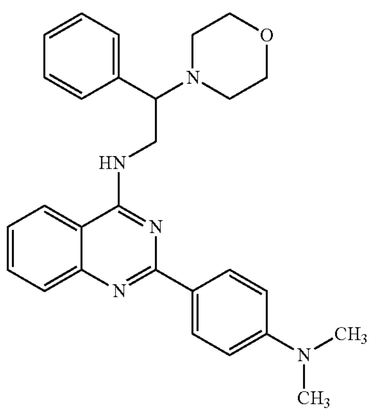 [SMILES: CN(C)c1ccc(-c2nc(NCC(c3ccccc3)N3CCOCC3)c3ccccc3n2)cc1] | 2-(4-(dimethylamino)phenyl)-N-(2-morpholino-2-phenylethyl)quinazolin-4-amine | 454 |
| 19 | 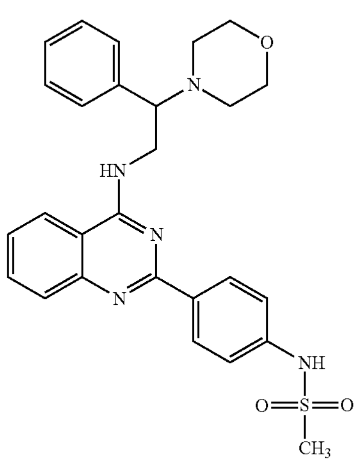 [SMILES: CS(=O)(=O)Nc1ccc(-c2nc(NCC(c3ccccc3)N3CCOCC3)c3ccccc3n2)cc1] | N-(4-(4-((2-morpholino-2-phenylethyl)amino)quinazolin-2-yl)phenyl)methanesulfonamide | 504 |

TABLE 1-continued

| No. | Structure | Name | M + H |
|---|---|---|---|
| 20 | 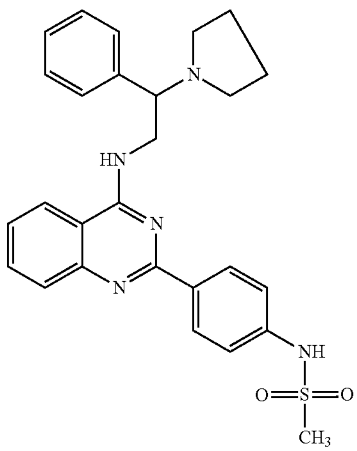 [SMILES: CS(=O)(=O)Nc1ccc(-c2nc(NCC(c3ccccc3)N3CCCC3)c3ccccc3n2)cc1] | N-(4-(4-((2-phenyl-2-(pyrrolidin-1-yl)ethyl)amino)quinazolin-2-yl)phenyl)methanesulfonamide | 488 |
| 21 | 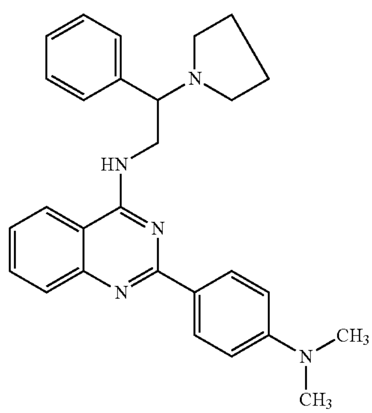 [SMILES: CN(C)c1ccc(-c2nc(NCC(c3ccccc3)N3CCCC3)c3ccccc3n2)cc1] | 2-(4-(dimethylamino)phenyl)-N-(2-phenyl-2-(pyrrolidin-1-yl)ethyl)quinazolin-4-amine | 438 |
| 22 | 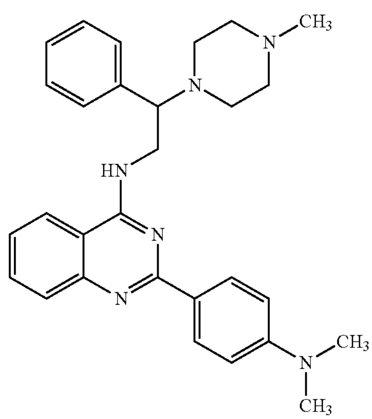 [SMILES: CN1CCN(C(CNc2nc(-c3ccc(N(C)C)cc3)nc3ccccc23)c2ccccc2)CC1] | 2-(4-(dimethylamino)phenyl)-N-(2-(4-methylpiperazin-1-yl)-2-phenylethyl)quinazolin-4-amine | 467 |

TABLE 1-continued

| No. | Structure | Name | M + H |
|---|---|---|---|
| 23 | 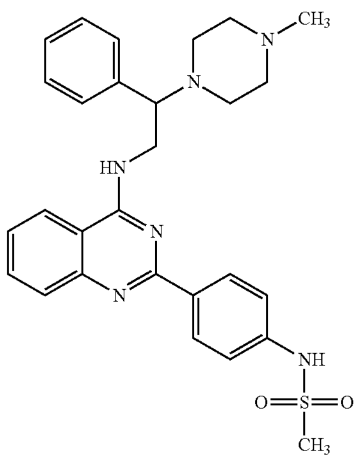 [SMILES: CN1CCN(C(CNc2nc(-c3ccc(NS(C)(=O)=O)cc3)nc3ccccc23)c2ccccc2)CC1] | N-(4-(4-((2-(4-methylpiperazin-1-yl)-2-phenylethyl)amino)quinazolin-2-yl)phenyl)methanesulfonamide | 517 |
| 24 | 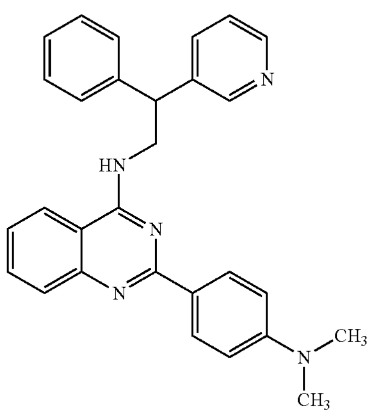 [SMILES: CN(C)c1ccc(-c2nc(NCC(c3ccccc3)c3cccnc3)c3ccccc3n2)cc1] | 2-(4-(dimethylamino)phenyl)-N-(2-phenyl-2-(pyridin-3-yl)ethyl)quinazolin-4-amine | 446 |
| 25 | 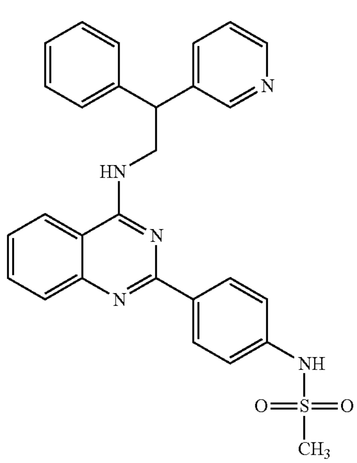 [SMILES: CS(=O)(=O)Nc1ccc(-c2nc(NCC(c3ccccc3)c3cccnc3)c3ccccc3n2)cc1] | N-(4-(4-((2-phenyl-2-(pyridin-3-yl)ethyl)amino)quinazolin-2-yl)phenyl)methanesulfonamide | 496 |

TABLE 1-continued

| No. | Structure | Name | M + H |
|---|---|---|---|
| 26 | 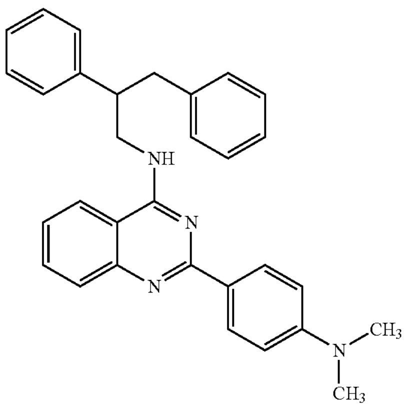 [SMILES: CN(C)c1ccc(-c2nc(NCC(Cc3ccccc3)c3ccccc3)c3ccccc3n2)cc1] | 2-(4-(dimethylamino)phenyl)-N-(2,3-diphenylpropyl)quinazolin-4-amine | 459 |
| 27 | 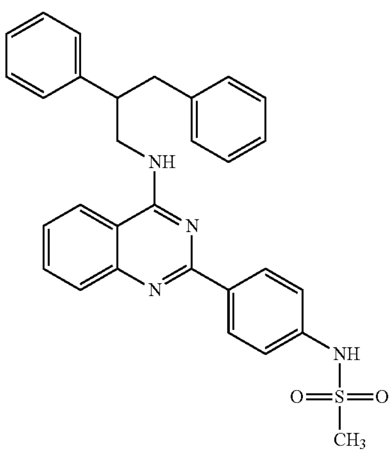 [SMILES: CS(=O)(=O)Nc1ccc(-c2nc(NCC(Cc3ccccc3)c3ccccc3)c3ccccc3n2)cc1] | N-(4-(4-((2,3-diphenylpropyl)amino)quinazolin-2-yl)phenyl)methanesulfonamide | 509 |
| 28 | 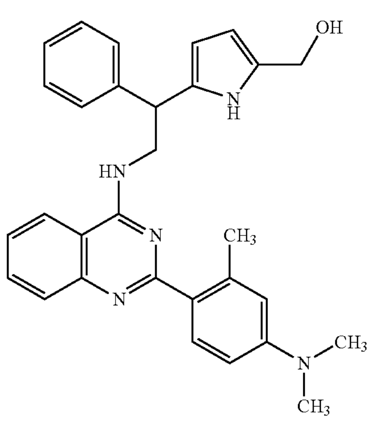 [SMILES: Cc1cc(N(C)C)ccc1-c1nc(NCC(c2ccccc2)c2ccc(CO)[nH]2)c2ccccc2n1] | (5-(2-((2-(4-(dimethylamino)-2-methylphenyl)quinazolin-4-yl)amino)-1-phenylethyl)-1H-pyrrol-2-yl)methanol | 478 |

TABLE 1-continued

| No. | Structure | Name | M + H |
|---|---|---|---|
| 29 | 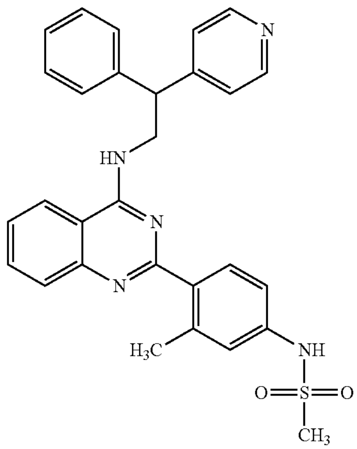 [SMILES: Cc1cc(NS(C)(=O)=O)ccc1-c1nc(NCC(c2ccccc2)c2ccncc2)c2ccccc2n1] | N-(3-methyl-4-(4-((2-phenyl-2-(pyridin-4-yl)ethyl)amino)quinazolin-2-yl)phenyl)methanesulfonamide | 510 |
| 30 | 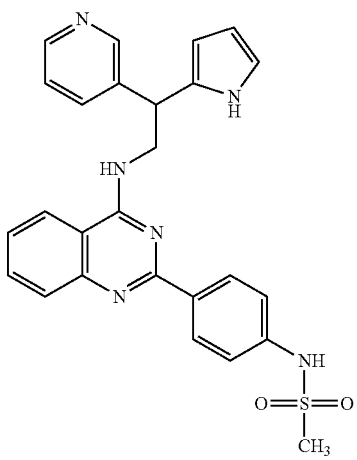 [SMILES: CS(=O)(=O)Nc1ccc(-c2nc(NCC(c3cccnc3)c3ccc[nH]3)c3ccccc3n2)cc1] | N-(4-(4-((2-(pyridin-3-yl)-2-(1H-pyrrol-2-yl)ethyl)amino)quinazolin-2-yl)phenyl)methanesulfonamide | 485 |
| 31 | 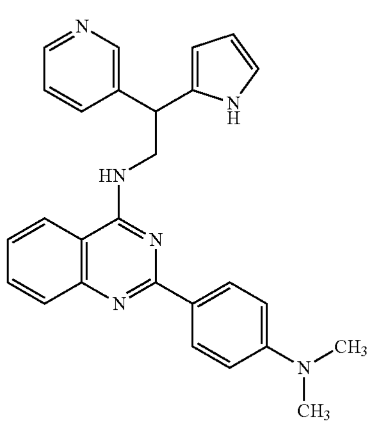 [SMILES: CN(C)c1ccc(-c2nc(NCC(c3cccnc3)c3ccc[nH]3)c3ccccc3n2)cc1] | 2-(4-(dimethylamino)phenyl)-N-(2-(pyridin-3-yl)-2-(1H-pyrrol-2-yl)ethyl)quinazolin-4-amine | 435 |

TABLE 1-continued

| No. | Structure | Name | M + H |
|---|---|---|---|
| 32 | 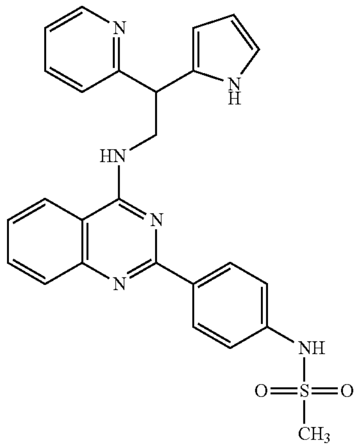 [SMILES: CS(=O)(=O)Nc1ccc(-c2nc(NCC(c3ccccn3)c3ccc[nH]3)c3ccccc3n2)cc1] | N-(4-(4-((2-(pyridin-2-yl)-2-(1H-pyrrol-2-yl)ethyl)amino)quinazolin-2-yl)phenyl)methanesulfonamide | 485 |
| 33 | 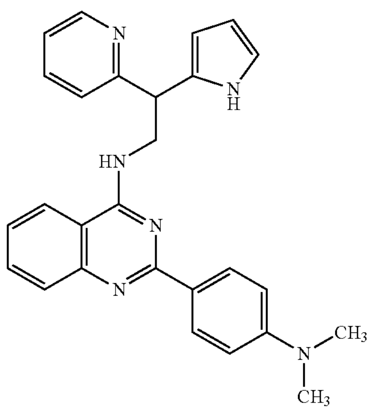 [SMILES: CN(C)c1ccc(-c2nc(NCC(c3ccccn3)c3ccc[nH]3)c3ccccc3n2)cc1] | 2-(4-(dimethylamino)phenyl)-N-(2-(pyridin-2-yl)-2-(1H-pyrrol-2-yl)ethyl)quinazolin-4-amine | 435 |
| 34 | 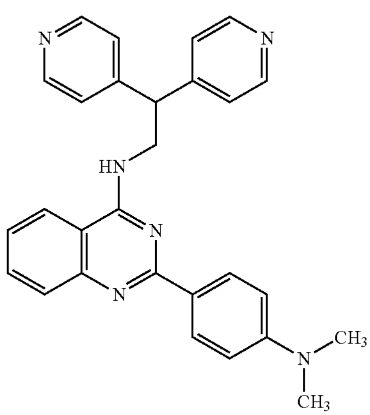 [SMILES: CN(C)c1ccc(-c2nc(NCC(c3ccncc3)c3ccncc3)c3ccccc3n2)cc1] | N-(2,2-di(pyridin-4-yl)ethyl)-2-(4-(dimethylamino)phenyl)quinazolin-4-amine | 447 |

TABLE 1-continued

| No. | Structure | Name | M + H |
|---|---|---|---|
| 35 | 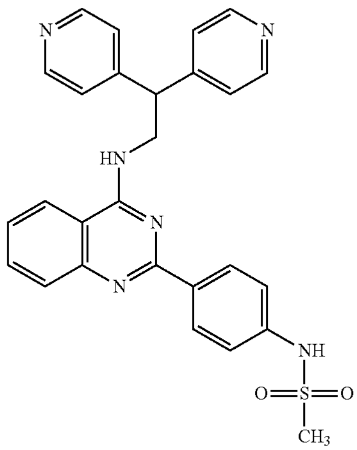 [SMILES: CS(=O)(=O)Nc1ccc(-c2nc(NCC(c3ccncc3)c3ccncc3)c3ccccc3n2)cc1] | N-(4-(4-((2,2-di(pyridin-4-yl)ethyl)amino)quinazolin-2-yl)phenyl)methanesulfonamide | 497 |
| 36 | 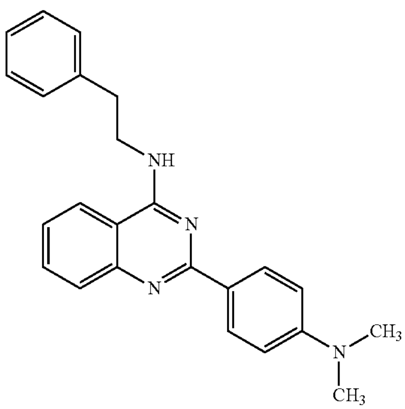 [SMILES: CN(C)c1ccc(-c2nc(NCCc3ccccc3)c3ccccc3n2)cc1] | 2-(4-(dimethylamino)phenyl)-N-phenethylquinazolin-4-amine | 369 |
| 37 | 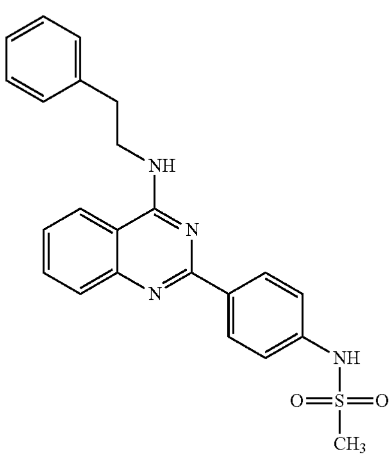 [SMILES: CS(=O)(=O)Nc1ccc(-c2nc(NCCc3ccccc3)c3ccccc3n2)cc1] | N-(4-(4-(phenethylamino)quinazolin-2-yl)phenyl)methanesulfonamide | 419 |

TABLE 1-continued

| No. | Structure | Name | M + H |
|---|---|---|---|
| 38 | 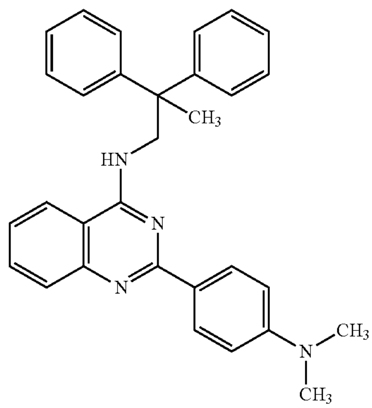 [SMILES: CN(C)c1ccc(-c2nc(NCC(C)(c3ccccc3)c3ccccc3)c3ccccc3n2)cc1] | 2-(4-(dimethylamino)phenyl)-N-(2,2-diphenylpropyl)quinazolin-4-amine | 459 |
| 39 | 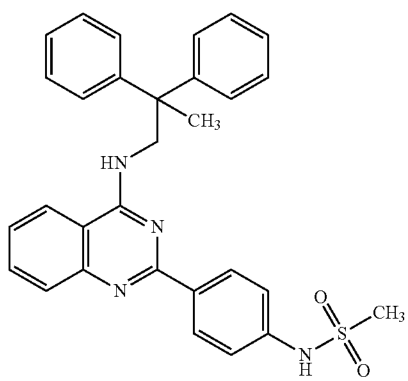 [SMILES: CC(CNc1nc(-c2ccc(NS(C)(=O)=O)cc2)nc2ccccc12)(c1ccccc1)c1ccccc1] | N-(4-(4-((2,2-diphenylpropyl)amino)quinazolin-2-yl)phenyl)methanesulfonamide | 509 |
| 40 | 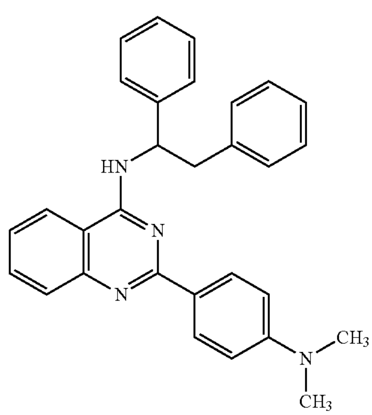 [SMILES: CN(C)c1ccc(-c2nc(NC(Cc3ccccc3)c3ccccc3)c3ccccc3n2)cc1] | 2-(4-(dimethylamino)phenyl)-N-(1,2-diphenylethyl)quinazolin-4-amine | 445 |

TABLE 1-continued

| No. | Structure | Name | M + H |
|---|---|---|---|
| 41 | 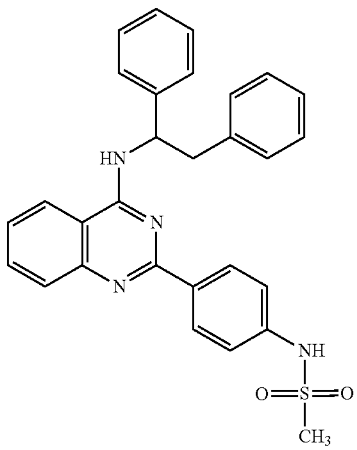 [SMILES: CS(=O)(=O)Nc1ccc(-c2nc(NC(Cc3ccccc3)c3ccccc3)c3ccccc3n2)cc1] | N-(4-(4-((1,2-diphenylethyl)amino)quinazolin-2-yl)phenyl)methanesulfonamide | 495 |
| 42 | 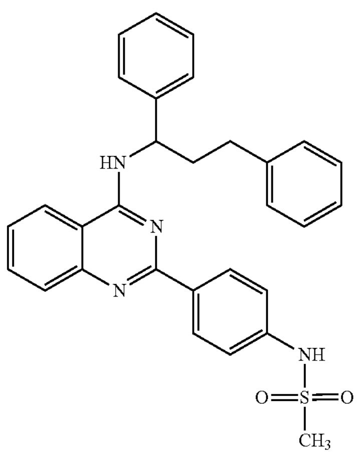 [SMILES: CS(=O)(=O)Nc1ccc(-c2nc(NC(CCc3ccccc3)c3ccccc3)c3ccccc3n2)cc1] | N-(4-(4-((1,3-diphenylpropyl)amino)quinazolin-2-yl)phenyl)methanesulfonamide | 509 |
| 43 | 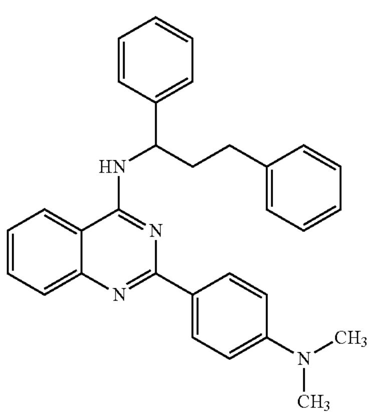 [SMILES: CN(C)c1ccc(-c2nc(NC(CCc3ccccc3)c3ccccc3)c3ccccc3n2)cc1] | 2-(4-(dimethylamino)phenyl)-N-(1,3-diphenylpropyl)quinazolin-4-amine | 459 |

TABLE 1-continued

| No. | Structure | Name | M + H |
|---|---|---|---|
| 44 | 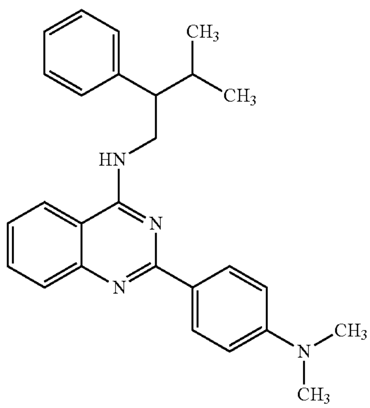 [SMILES: CC(C)C(CNc1nc(-c2ccc(N(C)C)cc2)nc2ccccc12)c1ccccc1] | 2-(4-(dimethylamino)phenyl)-N-(3-methyl-2-phenylbutyl)quinazolin-4-amine | 411 |
| 45 | 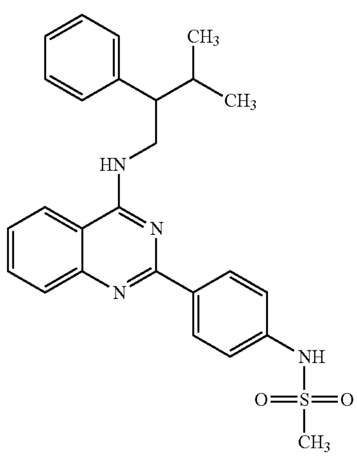 [SMILES: CC(C)C(CNc1nc(-c2ccc(NS(C)(=O)=O)cc2)nc2ccccc12)c1ccccc1] | N-(4-(4-((3-methyl-2-phenylbutyl)amino)quinazolin-2-yl)phenyl)methanesulfonamide | 461 |
| 46 | 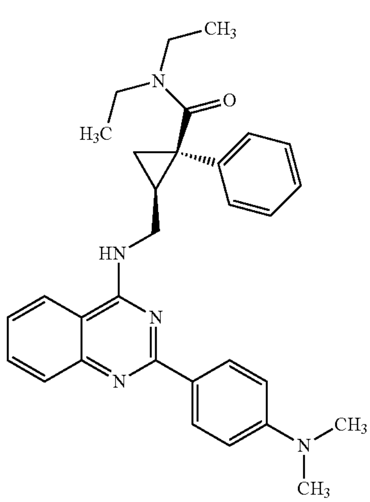 [SMILES: CCN(CC)C(=O)[C@]1(c2ccccc2)C[C@@H]1CNc1nc(-c2ccc(N(C)C)cc2)nc2ccccc12] | (1R,2S)-2-(((2-(4-(dimethylamino)phenyl)quinazolin-4-yl)amino)methyl)-N,N-diethyl-1-phenylcyclopropanecarboxamide | 494 |

TABLE 1-continued

| No. | Structure | Name | M + H |
|---|---|---|---|
| 47 | 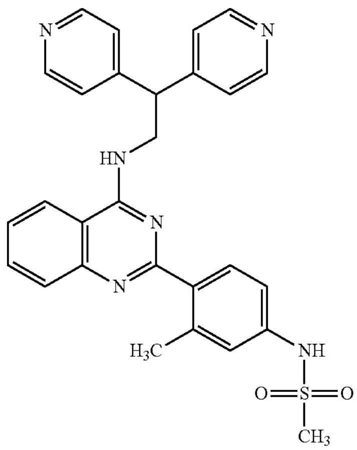 [SMILES: Cc1cc(NS(C)(=O)=O)ccc1-c1nc(NCC(c2ccncc2)c2ccncc2)c2ccccc2n1] | N-(4-(4-((2,2-di(pyridin-4-yl)ethyl)amino)quinazolin-2-yl)-3-methylphenyl)methanesulfonamide | 511 |
| 48 | 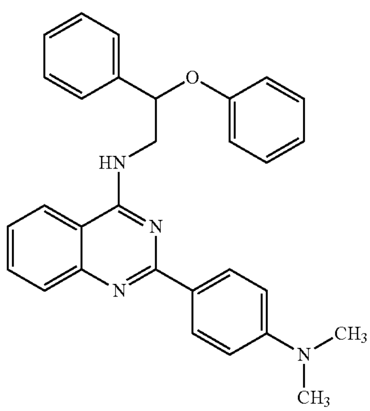 [SMILES: CN(C)c1ccc(-c2nc(NCC(Oc3ccccc3)c3ccccc3)c3ccccc3n2)cc1] | 2-(4-(dimethylamino)phenyl)-N-(2-phenoxy-2-phenylethyl)quinazolin-4-amine | 461 |
| 49 | 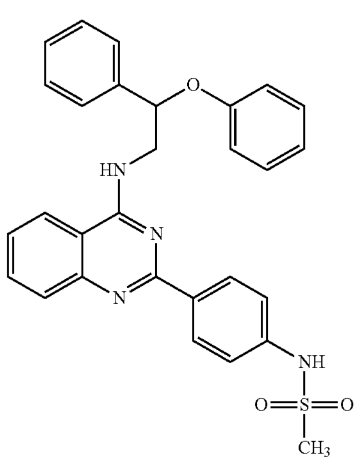 [SMILES: CS(=O)(=O)Nc1ccc(-c2nc(NCC(Oc3ccccc3)c3ccccc3)c3ccccc3n2)cc1] | N-(4-(4-((2-phenoxy-2-phenylethyl)amino)quinazolin-2-yl)phenyl)methanesulfonamide | 511 |

TABLE 1-continued

| No. | Structure | Name | M + H |
|---|---|---|---|
| 50 | 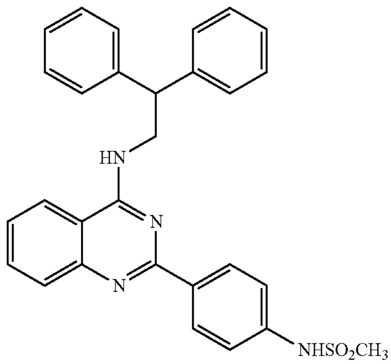 | N-(4-(4-((2,2-diphenylethyl)amino)quinazolin-2-yl)phenyl)methanesulfonamide | 494 |
| 51 | 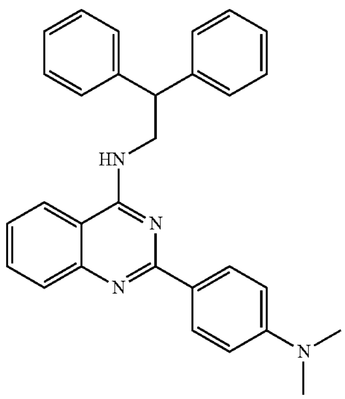 [SMILES: CN(C)c1ccc(-c2nc(NCC(c3ccccc3)c3ccccc3)c3ccccc3n2)cc1] | 2-(4-(dimethylamino)phenyl)-N-(2,2-diphenylethyl)quinazolin-4-amine | 444 |
| 52 | 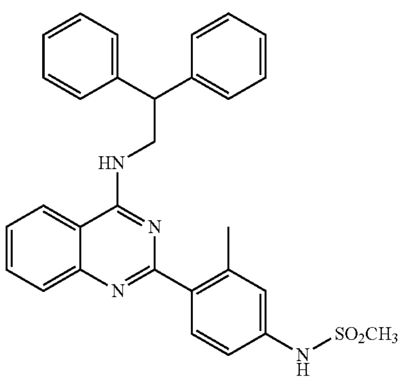 [SMILES: Cc1cc(NS(C)(=O)=O)ccc1-c1nc(NCC(c2ccccc2)c2ccccc2)c2ccccc2n1] | N-(4-(4-((2,2-diphenylethyl)amino)quinazolin-2-yl)-3-methylphenyl)methanesulfonamide | 508 |
| 53 | 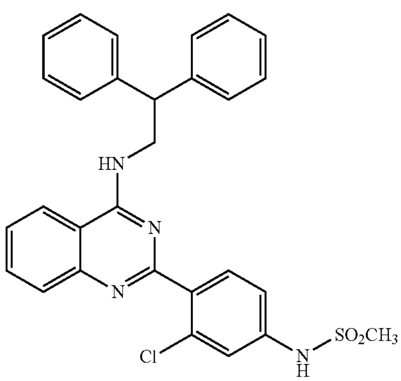 [SMILES: CS(=O)(=O)Nc1ccc(-c2nc(NCC(c3ccccc3)c3ccccc3)c3ccccc3n2)c(Cl)c1] | N-(3-chloro-4-(4-((2,2-diphenylethyl)amino)quinazolin-2-yl)phenyl)methanesulfonamide | 528 |

C. METHODS OF MAKING THE COMPOUNDS

Compounds of the present disclosure can be prepared by a variety of methods using readily available starting materials or known intermediates. The synthetic schemes shown below provide exemplary synthetic pathways for the preparation of compounds of the invention. The synthetic schemes are merely illustrative of some of the methods by which compounds of the present invention can be synthesized, and various modifications to these synthetic reaction schemes would be apparent to one skilled in the art within the scope of the present invention. Schemes 1 illustrates the general synthetic approach for compounds described herein. In Scheme 1, X and Y are leaving groups, such as Cl, Br, I, mercapto, sulfoxo, sulfonyl, alkoxy, aryloxy, sulfonyloxy group; and R$^1$Q is an organoborane, organozinc or organometallic compound, wherein Q can be B(OH)$_2$, B(OR')$_2$, ZnX or other suitable agents. Other substituents are as defined in Formula (I).

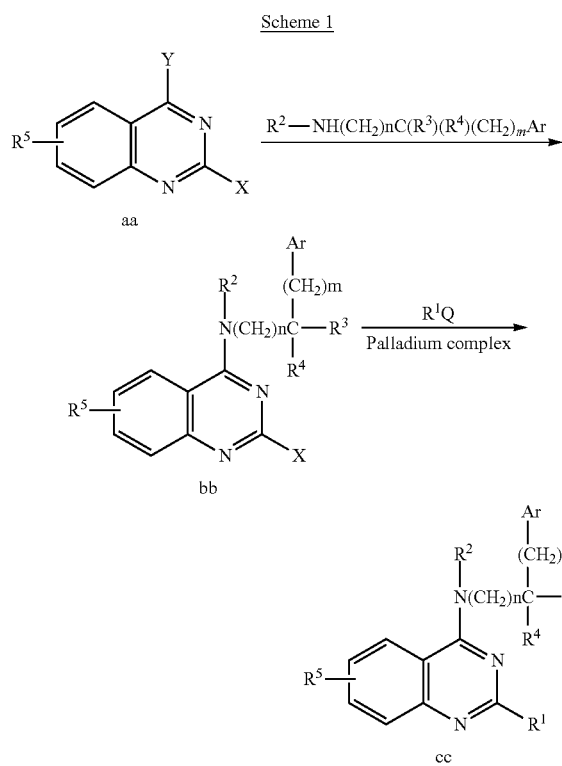

Scheme 1

The quinazolines (aa) used as starting material are either commercially available or can be readily prepared using literature methods. These starting materials are reacted with appropriate amines under mild reaction conditions to selectively displace the leaving group at the 4-position to obtain the 4-aminoquinazoline intermediates (bb). These intermediates (bb) are further reacted with an organoborane, organozinc or organometallic reagent typically in the presences of suitable palladium complex catalyst to yield compounds (cc).

Specific details for producing compounds of the invention are described in the Examples section.

D. METHODS OF TREATING DISEASES ASSOCIATED WITH DYSFUNCTION OF DOPAMINE NEUROTRANSMISSION, SEROTONIN NEUROTRANSMISSION, AND/OR NOREPINEPHRINE NEUROTRANSMISSION

The compounds of the present disclosure are useful for the treatment of diseases or conditions associated with dysfunction of dopamine neurotransmission, serotonin neurotransmission and/or norepinephrine neurotransmission such as depression.

The compounds of the present disclosure are also useful for the treatment of pain conditions from a wide variety of causes, including, but not limited to, neuropathic pain, inflammatory pain, pain due to burns, migraine or cluster headaches, nerve injury, neuritis, neuralgia, ischemic injury, intestinal cystitis, cancer pain, viral, parasitic or bacterial infections, post-traumatic injuries including fracture and sports injuries, and pain associated with bowel disorders such as irritable bowel syndrome.

The compounds of the present disclosure are also useful for the treatment of addiction to substances such as cocaine, methamphetamine, nicotine and alcohol.

Exemplary embodiments according to the present disclosure are as follows:

Embodiment 1

A compound formula (I):

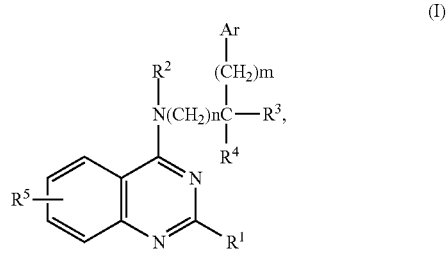

(I)

wherein n is 0, 1 or 2; m is 0, 1 or 2; R$^1$ is a substituted phenyl; R$^2$ is H or lower alkyl group; Ar is a phenyl or heterocyclic group; R$^3$ is H, alkyl, aryl, aralkyl, heteroaryl or heteroarylalkyl; R$^4$ is H, alkyl, hydroxy, alkoxy, aryloxy, heteroaryloxy, amino, alkylamino or dialkylamino; R$^3$ and R$^4$ together form a carbocycle or heterocycle; R$^5$ is H, halogen, alkyl, aryl, hydroxy, alkoxy, aryloxy, amino, alkylamino or dialkylamino, pharmaceutically acceptable salts thereof, deuterated forms thereof, isomers thereof, solvates thereof, and mixtures thereof.

Embodiment 2

The compound according to Embodiment 1 being of the formula (I):

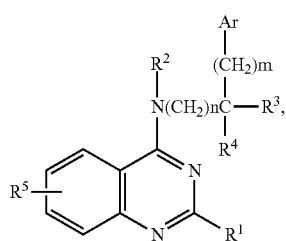

(I)

n is: 0, 1 or 2; m is: 0, 1 or 2; $R^1$ is a phenyl group containing one or more substituents; $R^2$ is H or lower alkyl group; Ar is: (a) a phenyl or substituted phenyl; or (b) a heteroaryl selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, each optionally substituted; $R^3$ is: (a) H, alkyl or cycloalkyl; (b) phenyl or substituted phenyl; or (c) heteroaryl selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, each optionally substituted; (d) aralkyl selected from benzyl, phenethyl, each optionally substituted; (e) heteroarylalkyl such as 2-pyridylmethyl, 3-pyridylmethyl, 4-pyridylmethyl, 2-thienylmethyl, 3-thienylmethyl, 2-furanymethyl, 3-furanylmethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanyethyl, 3-furanylethyl, 2-pyrrolylethyl, 3-pyrrolylethyl, and heteroarylalkyls wherein heteroaryl contains two or more heteroatoms, each optionally substituted; $R^4$ is H, alkyl, hydroxy, alkoxy, aryloxy, heteroaryloxy, amino, alkylamino, or dialkylamino including a dialkylamine that is a nitrogen heterocycle such as aziridine, azetidine, pyrrolidine, piperidine, morpholine, piperazine, azepane, diazepane and azocane. These rings may contain additional substituents or groups such as alkyl, aryl, arylalkyl, heteroaryl, heteroarylalkyl, alkenyl, alkoxy, hydroxyl, protected hydroxyl, alkanoyl, carboxy, alkoxycarbonyl and carbamoyl. They also may have one or more oxo, thioxo, imino, methylene or additional atoms such as O, N, S, P, Se and Te, and be part of a fused bicyclic or polycyclic saturated or unsaturated system. $R^3$ and $R^4$ together form a carbocycle or heterocycle consisting of 3-9 atoms; $R^5$ is: (a) H, lower alkyl or aryl group; (b) halogen such as fluoro, chloro, bromo and iodo; or (c) hydroxyl, alkoxy, dialkylaminoalkoxy, aryloxy, amino, alkylamino and dialkylamino; pharmaceutically acceptable salts thereof, deuterated forms thereof, isomers thereof, solvates thereof, and mixtures thereof.

Embodiment 3

The compound according to Embodiment 2, wherein the substituents in the phenyl, aryl and heteroaryl rings are individually selected from the group consisting of H, hydroxyl, chlorine, fluorine, bromine, trifluoromethyl, cyano, amino, carboxy, sulfo, sulfamoyl, unsubstituted or hydroxyl substituted C1-C6 alkyl, unsubstituted or hydroxyl substituted C1-C6 alkylthio, unsubstituted or substituted C2-C6 alkenyl, unsubstituted or substituted C2-C6 alkynyl, alkoxy, unsubstituted or substituted aryl or unsubstituted or substituted heteroaryl.

Embodiment 4

The compound according to Embodiment 1 having the formula (II):

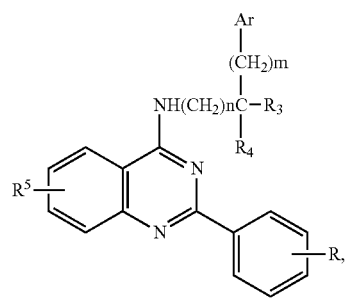

(II)

wherein R represents a lower alkyl, dialkylamino, or sulfonylamino group; pharmaceutically acceptable salts thereof, deuterated forms thereof, isomers thereof, solvates thereof, and mixtures thereof.

Embodiment 5

The compound according to Embodiment 1 having the formula (III):

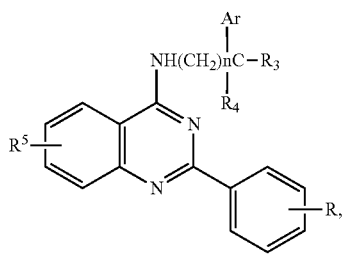

(III)

wherein R represents a lower alkyl, dialkylamino, or sulfonylamino group; pharmaceutically acceptable salts thereof, deuterated forms thereof, isomers thereof, solvates thereof, and mixtures thereof.

Embodiment 6

The compound according to Embodiment 1 having the formula (IV):

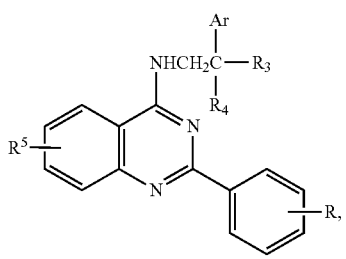

(IV)

wherein R represents a lower alkyl, dialkylamino, or sulfonylamino group pharmaceutically acceptable salts thereof, deuterated forms thereof, isomers thereof, solvates thereof, and mixtures thereof.

Embodiment 7

The compound according to Embodiment 1 having the formula (V):

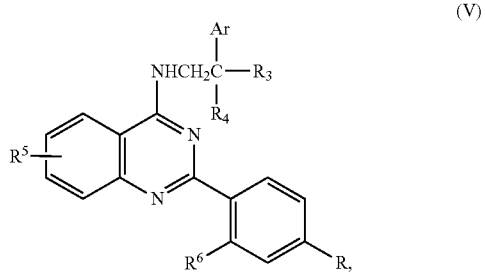

R represents a lower alkyl, dialkylamino, or sulfonylamino group and $R^6$ is H, halogen, methyl, trifluoromethyl, lower alkyl or alkoxy group, pharmaceutically acceptable salts thereof, deuterated forms thereof, isomers thereof, solvates thereof, and mixtures thereof.

Embodiment 8

The compound according to Embodiment 1 being selected from the group consisting of: 2-(4-(Dimethylamino)phenyl)-N-(2-phenyl-2-(pyridin-2-yl)ethyl)quinazolin-4-amine (3); N-(4-(4-((2-Hydroxy-2,2-diphenylethyl)amino)quinazolin-2-yl)phenyl)methanesulfonamide (4); 2-((2-(4-(Dimethylamino)phenyl)quinazolin-4-yl)amino)-1,1-diphenylethanol (5); N-(4-(4-((2-Cyclohexyl-2-phenylethyl)amino)quinazolin-2-yl)phenyl)methanesulfonamide (6); N-(2-Cyclohexyl-2-phenylethyl)-2-(4-(dimethylamino)phenyl)quinazolin-4-amine (7); N-(4-(4-((2-Phenyl-2-(pyridin-4-yl)ethyl)amino)quinazolin-2-yl)phenyl)methanesulfonamide (10); 2-(4-(Dimethylamino)phenyl)-N-(2-phenyl-2-(pyridin-4-yl)ethyl)quinazolin-4-amine (11); 2-(4-(Dimethylamino)phenyl)-N-(2-phenyl-2-(1H-pyrrol-2-yl)ethyl)quinazolin-4-amine (14); N-(4-(4-((2-Phenyl-2-(1H-pyrrol-2-yl)ethyl)amino)quinazolin-2-yl)phenyl)methanesulfonamide (15); 2-(4-(Dimethylamino)phenyl)-N-(2-phenyl-2-(piperidin-1-yl)ethyl)quinazolin-4-amine (16); 2-(4-(Dimethylamino)phenyl)-N-(2-morpholino-2-phenylethyl)quinazolin-4-amine (18); N-(4-(4-((2-Morpholino-2-phenylethyl)amino)quinazolin-2-yl)phenyl)methanesulfonamide (19); 2-(4-(Dimethylamino)phenyl)-N-(2-(4-methylpiperazin-1-yl)-2-phenylethyl)quinazolin-4-amine (22); 2-(4-(Dimethylamino)phenyl)-N-(2-phenyl-2-(pyridin-3-yl)ethyl)quinazolin-4-amine (24); N-(4-(4-((2-Phenyl-2-(pyridin-3-yl)ethyl)amino)quinazolin-2-yl)phenyl)methanesulfonamide (25); 2-(4-(Dimethylamino)phenyl)-N-(2,3-diphenylpropyl)quinazolin-4-amine (26); (5-(2-((2-(4-(Dimethylamino)-2-methylphenyl)quinazolin-4-yl)amino)-1-phenylethyl)-1H-pyrrol-2-yl)methanol (28); N-(3-Methyl-4-(4-((2-phenyl-2-(pyridin-4-yl)ethyl)amino)quinazolin-2-yl)phenyl)methanesulfonamide (29); 2-(4-(Dimethylamino)phenyl)-N-(2-(pyridin-3-yl)-2-(1H-pyrrol-2-yl)ethyl)quinazolin-4-amine (31); N-(2,2-Di(pyridin-4-yl)ethyl)-2-(4-(dimethylamino)phenyl)quinazolin-4-amine (34); N-(4-(4-((2,2-Di(pyridin-4-yl)ethyl)amino)quinazolin-2-yl)phenyl)methanesulfonamide (35); 2-(4-(Dimethylamino)phenyl)-N-(2,2-diphenylpropyl)quinazolin-4-amine (38); N-(4-(4-((2,2-Diphenylpropyl)amino)quinazolin-2-yl)phenyl)methanesulfonamide (39); 2-(4-(Dimethylamino)phenyl)-N-(1,2-diphenylethyl)quinazolin-4-amine (40); 2-(4-(Dimethylamino)phenyl)-N-(3-methyl-2-phenylbutyl)quinazolin-4-amine (44); N-(4-(4-((3-Methyl-2-phenylbutyl)amino)quinazolin-2-yl)phenyl)methanesulfonamide (45); 2-(4-(Dimethylamino)phenyl)-N-(2-phenoxy-2-phenylethyl)quinazolin-4-amine (48); N-(4-(4-((2-Phenoxy-2-phenylethyl)amino)quinazolin-2-yl)phenyl)methanesulfonamide (49); pharmaceutically acceptable salts thereof, deuterated forms thereof, isomers thereof, solvates thereof, and mixtures thereof.

Embodiment 9

A pharmaceutical composition comprising a compound according to any one of Embodiments 1-8, pharmaceutically acceptable salts thereof, deuterated forms thereof, isomers thereof, solvates thereof and mixtures thereof and a pharmaceutically acceptable carrier.

Embodiment 10

A method for treating a patient suffering from depression, pain, or addiction to substances, which comprises administering to the patient an effective amount of at least one compound or composition according to any one of Embodiments 1-8, pharmaceutically acceptable salts thereof, deuterium forms thereof, isomers thereof, solvates thereof and mixtures thereof and/or a pharmaceutical composition according to Embodiment 9.

Embodiment 11

The method according to Embodiment 10, wherein said substance is selected from the group consisting of cocaine, methamphetamine, nicotine and alcohol.

Embodiment 12

A process for the preparation of a compound according to any one of Embodiments 1-8.

E. ADMINISTRATION AND PHARMACEUTICAL COMPOSITIONS

In keeping with the present disclosure, the compounds of the present disclosure can be used alone or in appropriate association, and also may be used in combination with pharmaceutically acceptable carriers and other pharmaceutically active compounds. The active agent may be present in the pharmaceutical composition in any suitable quantity.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, and gels containing, in addition to the active ingredient, such carriers as are known in the art.

The compounds alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-doses or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, 4$^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

As regards these applications, the present method includes the administration to an animal, particularly a mammal, and more particularly a human, of a therapeutically effective amount of the compound effective in the treatment of a condition that is capable of treatment with an inhibitor of biogenic amine reuptake. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity.

The total amount of the compound of the present disclosure administered in a typical treatment is preferably between about 10 mg/kg and about 1000 mg/kg of body weight for mice, and between about 10 mg/kg and about 500 mg/kg of body weight, and more preferably between 20 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

F. EXAMPLES

The following preparations and examples are given to enable those skilled in the art to more clearly understand and to practice the present disclosure. They should not be considered as limiting the scope of the disclosure, but merely as being illustrative and representative.

1. General Experimental Methods

In the examples for the preparation, purification and characterization of compounds described below, melting points were determined in open capillary tubes with a Mel-Temp melting point apparatus or with an MPA100 OptiMelt automatic melting point apparatus. $^1$H NMR spectra were recorded at 300 MHz or 400 MHz on a Nicolet 300NB spectrometer. Chemical shifts are expressed in parts per million downfield from tetramethylsilane. Mass spectra were recorded in electrospray ionization (ESI) mode using the Agilent Time of Flight 6210 spectrometer. Thin layer chromatography (TLC) was performed on Analtech silica gel GF 0.25 mm plates. Column chromatographic purifications were performed using Isco-Teledyne purification system. Purified samples were dried overnight in vacuum over $P_2O_5$ at 78° C. HPLC was done using Agilent 1100 LC equipped with a diode array UV detector and monitored at multiple wavelengths on Bondclone 10µ C18 column using Solvent A: $H_2O$, solvent B: MeOH, 1.0 mL/min; 30 min linear gradient from 10-90% solvent B. LC-MS was done using the Agilent Time of Flight 6210 spectrometer equipped with the Agilent 1100 HPLC series.

2. Chemistry Experimentals i. Synthesis of N-(2-(6-Chloropyridin-2-yl)-2-phenylethyl)-2-(p-tolyl)quinazolin-4-amine (1)

To a stirred solution of 4-chloro-2-p-tolylquinazoline (100 mg, 0.39 mmol) in THF (5 mL) was added dropwise N,N-diisopropylethylamine (0.10 mL, 0.59 mmol) and 2-(6-chloropyridin-2-yl)-2-phenylethanamine (100 mg, 0.43 mmol). After stirring for 4 hours at room temperature, the reaction mixture was diluted with water (5 mL) and extracted with EtOAc (3×5 mL). The combined organic layers were washed with water (3×5 mL), dried over $Na_2SO_4$, and filtered. The filtrate was concentrated under reduced pressure. The residue obtained was purified by column chromatography using hexanes:EtOAc (10-80%) as eluent to obtain 74 mg (42%) of the desired product. Mp 77° C. TLC $R_f$ 0.30 (cyclohexane-EtOAc, 1:1). $^1$H NMR (400 MHz, DMSO-$d_6$) δ 8.46-8.37 (m, 2H), 8.10 (dt, J=8.4, 1.0 Hz, 1H), 7.76 (t, J=7.7 Hz, 1H), 7.74-7.71 (m, 2H), 7.49-7.28 (m, 10H), 7.27-7.21 (m, 1H), 4.86 (t, J=7.2 Hz, 1H), 4.41 (ddd, J=13.2, 7.9, 5.5 Hz, 1H), 4.27 (dt, J=12.8, 6.3 Hz, 1H), 2.40 (s, 3H). HRMS m/z calcd for $C_{28}H_{23}ClN_4+H^+$ [M+H$^+$]: 451.1684. found: 451.1680. HPLC: 99% ($t_R$=14.0 min).

j. Synthesis of N-(4-(4-((2-Phenyl-2-(pyridin-2-yl)ethyl)amino)quinazolin-2-yl)phenyl)methanesulfonamide (2)

To the stirred solution of 2-chloro-N-(2-phenyl-2-(pyridin-2-yl)ethyl)quinazolin-4-amine (97.4 mg, 0.27 mmol) in dioxane:water (6 mL:1 mL) was added (4-(methylsulfonamido)phenyl)boronic acid (118 mg, 0.55 mmol) and $K_2CO_3$ (76.02 mg, 0.55 mmol). The reaction mixture was purged with argon and stirred for 15 minutes at room temperature. Tetrakis triphenylphosphine palladium (0.335 mg, 0.029 mmol) was added and the reaction mixture was heated under reflux for 15 hours. The reaction mixture was then cooled to room temperature, diluted with water and extracted with EtOAc (2×10 mL). The organic layer was separated, dried over anhydrous sodium sulfate and concentrated under reduced pressure. The residue obtained was purified by column chromatography using hexanes:EtOAc (0-70%) as eluent to obtain 98 mg (73%) of the desired product. Mp 114° C. TLC $R_f$ 0.45 (cyclohexane-EtOAc, 1:1). $^1$H NMR (400 MHz, DMSO-$d_6$) δ 10.02 (s, 1H), 8.60 (ddd, J=4.8, 1.8, 0.8 Hz, 1H), 8.49-8.41 (m, 2H), 8.37 (t, J=5.5 Hz, 1H), 8.09 (dt, J=8.4, 1.0 Hz, 1H), 7.76-7.64 (m, 3H), 7.49-7.41 (m, 2H), 7.41-7.34 (m, 2H), 7.34-7.26 (m, 4H), 7.26-7.16 (m, 2H), 4.87 (t, J=7.3 Hz, 1H), 4.43 (ddd, J=12.9, 7.6, 5.2 Hz, 1H), 4.33 (dt, J=13.0, 6.4 Hz, 1H), 3.07 (s, 3H). HRMS m/z calcd for $C_{28}H_{25}N_5O_2S+H^+$ [M+H$^+$]: 496.1802. found: 496.1812. HPLC: 100% ($t_R$=6.08 min).

k. Synthesis of 2-(4-(Dimethylamino)phenyl)-N-(2-phenyl-2-(pyridin-2-yl)ethyl)quinazolin-4-amine (3)

This compound was prepared from 2-chloro-N-(2-phenyl-2-(pyridin-2-yl)ethyl)quinazolin-5-amine and N,N-dimethyl-4-(4,4,5,5-tetramethyl-1,3,2-dioxaborolan-2-yl)aniline according to the procedure described for the preparation of compound 2. Yield 56%. Mp 177° C. TLC $R_f$ 0.25 (cyclohexane-EtOAc, 1:1). $^1$H NMR (400 MHz, DMSO-d$_6$) δ 8.60 (ddd, J=4.8, 1.9, 0.9 Hz, 1H), 8.41-8.32 (m, 2H), 8.21 (t, J=5.5 Hz, 1H), 8.03 (dd, J=8.2, 1.1 Hz, 1H), 7.74-7.57 (m, 3H), 7.48-7.41 (m, 2H), 7.39-7.15 (m, 6H), 6.84-6.75 (m, 2H), 4.89 (t, J=7.4 Hz, 1H), 4.45-4.26 (m, 2H), 3.01 (s, 6H). HRMS m/z calcd for $C_{29}H_{27}N_5$+H$^+$ [M+H$^+$]: 446.2339. found: 446.2356. HPLC: 100% ($t_R$=6.57 min).

l. Synthesis of N-(4-(4-((2-hydroxy-2,2-diphenylethyl)amino)quinazolin-2-yl)phenyl)methanesulfonamide (4)

This compound was prepared from 2-((2-chloroquinazolin-5-yl)amino)-1,1-diphenylethanol and (4-(methylsulfonamido)phenyl)boronic acid according to the procedure described for the preparation of compound 2. Yield 51%. Mp 244° C. TLC $R_f$ 0.40 (cyclohexane-EtOAc, 1:1). $^1$H NMR (400 MHz, DMSO-d$_6$) δ 10.07 (s, 1H), 8.47-8.39 (m, 2H), 8.14-8.07 (m, 1H), 7.81 (t, J=5.4 Hz, 1H), 7.78-7.69 (m, 2H), 7.60-7.52 (m, 4H), 7.44 (ddd, J=8.3, 6.1, 2.1 Hz, 1H), 7.34 (d, J=8.5 Hz, 2H), 7.31-7.25 (m, 4H), 7.22-7.13 (m, 2H), 6.75 (s, 1H), 4.51 (d, J=5.2 Hz, 2H), 3.08 (s, 3H). HRMS m/z calcd for $C_{29}H_{26}N_5O_3S$+H$^+$ [M+H$^+$]: 511.1798. found: 511.1801. HPLC: 100% ($t_R$=6.30 min).

m. Synthesis of 2-((2-(4-(Dimethylamino)phenyl)quinazolin-4-yl)amino)-1,1-diphenylethanol (5)

This compound was prepared from 2-((2-chloroquinazolin-5-yl)amino)-1,1-diphenylethanol and (4-(dimethylamino)phenyl)boronic acid according to the procedure described for the preparation of compound 2. Yield 78%. Mp 238° C. TLC $R_f$ 0.35 (cyclohexane-EtOAc, 1:1). $^1$H NMR (400 MHz, DMSO-d$_6$) δ 8.39-8.30 (m, 2H), 8.06 (dd, J=8.1, 1.2 Hz, 1H), 7.83 (s, 1H), 7.75-7.62 (m, 2H), 7.60-7.52 (m, 4H), 7.37 (ddd, J=8.2, 6.6, 1.6 Hz, 1H), 7.32-7.26 (m, 4H), 7.23-7.14 (m, 2H), 7.02 (s, 1H), 6.88-6.79 (m, 2H), 4.47 (d, J=5.1 Hz, 2H), 3.02 (s, 6H). HRMS m/z calcd for $C_{30}H_{28}N_4O$+H$^+$ [M+H$^+$]: 461.2336. found: 461.2348. HPLC: 100% ($t_R$=6.78 min).

n. Synthesis of N-(4-(4-((2-Cyclohexyl-2-phenylethyl)amino)quinazolin-2-yl)phenyl)methanesulfonamide (6)

This compound was prepared from 2-chloro-N-(2-cyclohexyl-2-phenylethyl)quinazolin-4-amine and (4-(methylsulfonamido)phenyl)boronic acid according to the procedure described for the preparation of compound 2. Yield 73%. Mp 106° C. TLC $R_f$ 0.30 (cyclohexane-EtOAc, 1:1). $^1$H NMR (400 MHz, DMSO-d$_6$) δ 9.99 (s, 1H), 8.48-8.39 (m, 2H), 8.11 (t, J=5.5 Hz, 1H), 8.07 (d, J=8.3 Hz, 1H), 7.75-7.65 (m, 2H), 7.38 (ddd, J=8.2, 5.5, 2.7 Hz, 1H), 7.33-7.27 (m, 2H), 7.26-7.17 (m, 4H), 7.17-7.11 (m, 1H), 4.17 (dt, J=13.3, 5.6 Hz, 1H), 3.95-3.82 (m, 1H), 3.11 (q, J=7.1 Hz, 1H), 3.07 (s, 3H), 2.02-1.94 (m, 1H), 1.73 (d, J=13.2 Hz, 2H), 1.59 (s, 3H), 1.23 (t, J=12.4 Hz, 1H), 1.14-0.99 (m, 3H), 0.81 (q, J=12.2, 11.7 Hz, 1H). HRMS m/z calcd for $C_{29}H_{32}N_4O_2S$+H$^+$ [M+H$^+$]: 501.2319. found: 501.2303. HPLC: 100% ($t_R$=5.91 min).

o. Synthesis of N-(2-Cyclohexyl-2-phenylethyl)-2-(4-(dimethylamino)phenyl)quinazolin-4-amine (7)

This compound was prepared from 2-chloro-N-(2-cyclohexyl-2-phenylethyl)quinazolin-4-amine and N,N-dimethyl-4-(4,4,5,5-tetramethyl-1,3,2-dioxaborolan-2-yl)aniline according to the procedure described for the preparation of compound 2. Yield 26%. Mp 207° C. TLC $R_f$ 0.30 (cyclohexane-EtOAc, 1:1). $^1$H NMR (400 MHz, DMSO-d$_6$) δ 8.39-8.30 (m, 2H), 8.01 (dd, J=8.2, 1.1 Hz, 1H), 7.94 (t, J=5.6 Hz, 1H), 7.69-7.57 (m, 2H), 7.30 (ddd, J=8.2, 6.3, 1.8 Hz, 1H), 7.27-7.18 (m, 4H), 7.18-7.12 (m, 1H), 6.83-6.74 (m, 2H), 4.17 (dt, J=12.2, 5.7 Hz, 1H), 3.85 (dt, J=13.8, 6.2 Hz, 1H), 3.13 (q, J=7.2 Hz, 1H), 3.01 (s, 6H), 1.97 (d, J=16.2 Hz, 1H), 1.73 (d, J=14.5 Hz, 2H), 1.60 (d, J=11.1 Hz, 3H), 1.25 (d, J=12.8 Hz, 1H), 1.13-1.00 (m, 3H), 0.82 (t, J=11.2 Hz, 1H). HRMS m/z calcd for $C_{30}H_{34}N_4$+H$^+$ [M+H$^+$]: 451.2856. found: 451.2845. HPLC: 100% ($t_R$=6.22 min).

p. Synthesis of N-(4-(4-((2-Phenyl-2-(pyrimidin-2-yl)ethyl)amino)quinazolin-2-yl)phenyl)methanesulfonamide (8)

This compound was prepared from 2-chloro-N-(2-phenyl-2-(pyrimidin-2-yl)ethyl)quinazolin-4-amine and (4-(methylsulfonamido)phenyl)boronic acid according to the procedure described for the preparation of compound 2. Yield 51%. Mp 221° C. TLC $R_f$ 0.45 (CHCl$_3$-MeOH, 9:1). $^1$H NMR (400 MHz, DMSO-d$_6$) δ 10.02 (s, 1H), 8.79 (dt, J=4.9, 0.6 Hz, 2H), 8.48-8.41 (m, 2H), 8.39 (t, J=5.5 Hz, 1H), 8.13-8.05 (m, 1H), 7.71 (dt, J=4.3, 0.9 Hz, 2H), 7.47-7.42 (m, 2H), 7.42-7.34 (m, 2H), 7.34-7.27 (m, 4H), 7.24-7.18 (m, 1H), 5.02 (t, J=7.3 Hz, 1H), 4.44 (ddd, J=13.0, 7.8, 5.1 Hz, 1H), 4.35 (dt, J=12.9, 6.3 Hz, 1H), 3.07 (s, 3H). HRMS m/z calcd for $C_{27}H_{24}N_6O_2S$+H$^+$ [M+H$^+$]: 497.1754. found: 497.1747. HPLC: 100% ($t_R$=6.03 min).

q. Synthesis of 2-(4-(Dimethylamino)phenyl)-N-(2-phenyl-2-(pyrimidin-2-yl)ethyl)quinazolin-4-amine (9)

This compound was prepared from 2-chloro-N-(2-phenyl-2-(pyrimidin-2-yl)ethyl)quinazolin-4-amine and N,N-dimethyl-4-(4,4,5,5-tetramethyl-1,3,2-dioxaborolan-2-yl)aniline according to the procedure described for the preparation of compound 2. Yield 32%. Mp 215° C. TLC $R_f$ 0.45 (CHCl$_3$-MeOH, 9:1). $^1$H NMR (400 MHz, DMSO-d$_6$) δ 8.79 (dt, J=4.9, 0.5 Hz, 2H), 8.40-8.31 (m, 2H), 8.23 (t, J=5.5 Hz, 1H), 8.07-8.00 (m, 1H), 7.65 (dd, J=6.0, 1.4 Hz, 2H), 7.48-7.40 (m, 2H), 7.36 (td, J=4.9, 0.5 Hz, 1H), 7.31 (dtd, J=8.0, 6.1, 5.6, 2.2 Hz, 3H), 7.25-7.18 (m, 1H), 6.84-6.75 (m, 2H), 5.03 (t, J=7.4 Hz, 1H), 4.37 (dddd, J=30.6, 12.9, 7.4, 5.5 Hz, 2H), 3.01 (s, 6H). HRMS m/z calcd for $C_{28}H_{26}N_6$+H$^+$ [M+H$^+$]: 447.2292. found: 447.2291. HPLC: 100% ($t_R$=6.53 min).

r. Synthesis of N-(4-(4-((2-Phenyl-2-(pyridin-4-yl)ethyl)amino)quinazolin-2-yl)phenyl)methanesulfonamide (10)

This compound was prepared from 2-chloro-N-(2-phenyl-2-(pyridin-4-yl)ethyl)quinazolin-4-amine and (4-(methylsulfonamido)phenyl)boronic acid according to the procedure described for the preparation of compound 2. Yield 73%. Mp 130° C. TLC $R_f$ 0.40 (CHCl$_3$-MeOH, 9:1). $^1$H NMR (400 MHz, DMSO-d$_6$) δ 10.01 (s, 1H), 8.49-8.37 (m, 5H), 8.10 (d, J=8.3 Hz, 1H), 7.76-7.68 (m, 2H), 7.46-7.38 (m, 5H), 7.37-7.29 (m, 4H), 7.26-7.21 (m, 1H), 4.74 (t, J=7.6 Hz, 1H), 4.42-4.26 (m, 2H), 3.07 (s, 3H). HRMS m/z calcd for $C_{28}H_{25}N_5O_2S$+H$^+$ [M+H$^+$]: 496.1802. found: 496.1798. HPLC: 100% ($t_R$=5.57 min).

s. Synthesis of 2-(4-(Dimethylamino)phenyl)-N-(2-phenyl-2-(pyridin-4-yl)ethyl)quinazolin-4-amine (11)

This compound was prepared from 2-chloro-N-(2-phenyl-2-(pyridin-4-yl)ethyl)quinazolin-4-amine and N,N-dimethyl-4-(4,4,5,5-tetramethyl-1,3,2-dioxaborolan-2-yl)aniline according to the procedure described for the preparation of compound 2. Yield 57%. Mp 103° C. TLC $R_f$ 0.40 (CHCl$_3$-MeOH, 9:1). $^1$H NMR (400 MHz, DMSO-d$_6$) δ 8.50-8.44 (m, 2H), 8.40-8.31 (m, 2H), 8.33-8.23 (m, 1H), 8.04 (d, J=8.2 Hz, 1H), 7.72-7.61 (m, 2H), 7.44-7.39 (m, 4H), 7.38-7.30 (m, 3H), 7.27-7.22 (m, 1H), 6.84-6.76 (m, 2H), 4.77 (t, J=7.6 Hz, 1H), 4.28 (ddt, J=20.1, 13.1, 6.1 Hz, 2H), 3.01 (s, 6H). HRMS m/z calcd for $C_{29}H_{27}N_5+H^+$ [M+H$^+$]: 446.2339. found: 446.2337. HPLC: 100% ($t_R$=6.15 min).

t. Synthesis of N-(4-(4-((2-(1H-Imidazol-1-yl)-2-phenylethyl)amino)quinazolin-2-yl)phenyl)methanesulfonamide (12)

This compound was prepared from N-(2-(1H-imidazol-1-yl)-2-phenylethyl)-2-chloroquinazolin-4-amine and (4-(methylsulfonamido)phenyl)boronic acid according to the procedure described for the preparation of compound 2. Yield 58%. Mp 136° C. TLC $R_f$ 0.35 (CHCl$_3$-MeOH, 9:1). $^1$H NMR (400 MHz, DMSO-d$_6$) δ 10.05 (s, 1H), 8.54 (t, J=5.5 Hz, 1H), 8.46 (dd, J=8.7, 1.4 Hz, 1H), 8.17-8.10 (m, 1H), 7.89 (q, J=0.9 Hz, 1H), 7.81-7.71 (m, 2H), 7.51-7.27 (m, 9H), 6.89 (q, J=0.9 Hz, 1H), 5.96 (dd, J=8.7, 5.8 Hz, 1H), 4.49-4.34 (m, 2H), 3.07 (d, J=1.5 Hz, 3H). HRMS m/z calcd for $C_{26}H_{24}N_6O_2S+H^+$ [M+H$^+$]: 485.1754. found: 485.1750. HPLC: 100% ($t_R$=5.14 min).

u. Synthesis of N-(2-(1H-Imidazol-1-yl)-2-phenylethyl)-2-(4-(dimethylamino)phenyl)quinazolin-4-amine (13)

This compound was prepared from N-(2-(1H-imidazol-1-yl)-2-phenylethyl)-2-chloroquinazolin-4-amine and (4-(dimethylamino)phenyl)boronic acid according to the procedure described for the preparation of compound 2. Yield 58%. Mp 222° C. TLC $R_f$ 0.35 (CHCl$_3$-MeOH, 9:1). $^1$H NMR (400 MHz, DMSO-d$_6$) δ 8.47-8.40 (m, 1H), 8.40-8.33 (m, 2H), 8.09 (d, J=8.2 Hz, 1H), 7.88 (t, J=1.1 Hz, 1H), 7.75-7.64 (m, 2H), 7.50-7.31 (m, 7H), 6.90 (t, J=1.0 Hz, 1H), 6.84-6.76 (m, 2H), 5.97 (dd, J=8.3, 6.1 Hz, 1H), 4.46-4.33 (m, 2H), 3.01 (s, 6H). HRMS m/z calcd for $C_{27}H_{26}N_6+H^+$ [M+H$^+$]: 435.2292. found: 435.2280. HPLC: 100% ($t_R$=5.60 min).

v. Synthesis of 2-(4-(Dimethylamino)phenyl)-N-(2-phenyl-2-(1H-pyrrol-2-yl)ethyl)quinazolin-4-amine (14)

To a stirred solution of 2-chloro-N-(2-phenyl-2-(1H-pyrrol-2-yl)ethyl)quinazolin-4-amine (0.094 g, 0.27 mmol) in dioxane:water (2 mL:2 mL) was added (4-(dimethylamino)phenyl)boronic acid (0.091 g, 0.55 mmol) and K$_2$CO$_3$ (76.02 mg, 0.55 mmol). The reaction mixture was purged with argon and stirred for 15 min. at room temperature. Tetrakis triphenylphosphine palladium (0.335 mg, 0.029 mmol) was added to the reaction mixture and the mixture was refluxed under microwave heating at 120° C. for 3-5 h. The reaction mixture was then cooled to room temperature, diluted with water and extracted with EtOAc (2×10 mL). The organic layer was separated, dried over anhydrous Na$_2$SO$_4$ and concentrated under reduced pressure. The residue obtained was purified by column chromatography using hexanes: EtOAc (0-100%) as eluent to obtain the desired product. Yield 89%. Mp 183-185° C. TLC $R_f$ 0.18 (hexane-EtOAc, 7:3). $^1$H NMR (400 MHz, DMSO-d$_6$) δ 8.47 (d, J=8.6 Hz, 2H), 8.44 (br s, 1H), 7.84 (d, J=7.8 Hz, 1H), 7.65 (m, 1H), 7.25-7.4 (m, 7H), 6.8 (d, J=8.6 Hz, 2H), 6.56 (m, 1H), 6.18-6.22 (m, 2H), 5.71 (t, J=5.6 Hz, 1H), 5.56 (t, J=7.5 Hz, 1H), 4.3-4.43 (m, 2H), 3.05 (s, 6H). HRMS m/z calcd for $C_{28}H_{27}N_5+H^+$ [M+H$^+$]: 434.2339. found: 434.2355. HPLC: 100% ($t_R$=6.72 min).

w. Synthesis of N-(4-(4-((2-Phenyl-2-(1H-pyrrol-2-yl)ethyl)amino)quinazolin-2-yl)phenyl)methanesulfonamide (15)

This compound was prepared from 2-chloro-N-(2-phenyl-2-(1H-pyrrol-2-yl)ethyl)quinazolin-4-amine and (4-(methylsulfonamido)phenyl)boronic acid according to the procedure described for the preparation of compound 14. Yield 69%. Mp 82-84° C. TLC $R_f$ 0.16 (hexane-EtOAc, 6:4). $^1$H NMR (400 MHz, DMSO-d$_6$) δ 8.57 (d, J=8.6 Hz, 2H), 8.14 (br s, 1H), 7.89 (d, J=7.8 Hz, 1H), 7.71 (m, 1H), 7.29-7.45 (m, 9H), 6.7 (m, 1H), 6.23-6.25 (m, 2H), 5.82 (t, J=5.6 Hz, 1H), 4.35 (t, J=7.4 Hz, 1H), 4.29-4.43 (m, 2H), 3.06 (s, 3H). HRMS m/z calcd for $C_{27}H_{25}N_5O_2S+H^+$ [M+H$^+$]: 484.1801. found: 484.1784. HPLC: 100% ($t_R$=6.21 min).

x. Synthesis of 2-(4-(Dimethylamino)phenyl)-N-(2-phenyl-2-(piperidin-1-yl)ethyl)quinazolin-4-amine (16)

This compound was prepared from 2-chloro-N-(2-phenyl-2-(piperidin-1-yl)ethyl)quinazolin-4-amine and (4-(dimethylamino)phenyl)boronic acid according to the procedure described for the preparation of compound 14. Yield 53%. Mp 191-193° C. TLC $R_f$ 0.33 (cyclohexane-EtOAc, 1:2). $^1$H NMR (400 MHz, DMSO-d$_6$) δ 8.33 (d, J=9 Hz, 2H), 8.04 (d, J=8.3 Hz, 1H), 7.92 (d, J=5.5 Hz, 1H), 7.69-7.62 (m, 2H), 7.36-7.22 (m, 6H), 6.98 (d, J=9 Hz, 2H), 4.21 (m, 1H), 7.04 (t, J=5.5 Hz, 1H), 3.96 (m, 1H), 3 (s, 6H), 2.5-2.45 (m, 2H), 2.36-2.32 (m, 2H), 1.45 (br s, 4H), 1.28 (m, 2H). HRMS m/z calcd for $C_{29}H_{33}N_5+H^+$ [M+H$^+$]: 452.2808. found: 452.2809. HPLC: 100% ($t_R$=5.55 min).

y. Synthesis of N-(4-(4-((2-Phenyl-2-(piperidin-1-yl)ethyl)amino)quinazolin-2-yl)phenyl)methanesulfonamide (17)

This compound was prepared from 2-chloro-N-(2-phenyl-2-(piperidin-1-yl)ethyl)quinazolin-4-amine and (4-(methylsulfonamido)phenyl)boronic acid according to the procedure described for the preparation of compound 14. Yield 50%. Mp 189-191° C. TLC $R_f$ 0.33 (cyclohexane-EtOAc, 2:3). $^1$H NMR (400 MHz, DMSO-d$_6$) δ 10.01 (br s, 1H), 8.43 (d, J=9 Hz, 2H), 8.15-8.06 (m, 3H), 7.78-7.67 (m, 2H), 7.43 (ddd, J=8.2, 5.7, 2.5 Hz, 2H), 7.37-7.19 (m, 7H), 4.24 (m, 1H), 4.08-3.91 (m, 2H), 3.07 (s, 3H), 2.57-2.49 (m, 2H), 2.36-2.32 (m, 2H), 1.44 (m, 4H), 1.31-1.24 (m, 2H). HRMS m/z calcd for $C_{28}H_{31}N_5O_2S+H^+$ [M+H$^+$]: 502.2271. found: 502.2270. HPLC: 100% ($t_R$=5.15 min).

z. Synthesis of 2-(4-(Dimethylamino)phenyl)-N-(2-morpholino-2-phenylethyl)quinazolin-4-amine (18)

This compound was prepared from 2-chloro-N-(2-morpholino-2-phenylethyl)quinazolin-4-amine and (4-(dimethylamino)phenyl)boronic acid according to the procedure described for the preparation of compound 14. Yield 53%. Mp 96-98° C. TLC R$_f$ 0.5 (CH$_2$Cl$_2$-MeOH, 9.6:0.4). $^1$H NMR (400 MHz, DMSO-d$_6$) δ 8.32 (d, J=9 Hz, 2H), 8.04 (m, 1H), 7.94 (t, J=5.5 Hz, 1H), 7.69-7.62 (m, 2H), 7.36-7.24 (m, 6H), 7.78 (d, J=9 Hz, 2H), 4.26 (m, 1H), 4.03-3.87 (m, 2H), 3.54 (t, J=4.5 Hz, 4H), 3.00 (s, 6H), 2.47 (m, 4H). HRMS m/z calcd for C$_{28}$H$_{31}$N$_5$O+H$^+$ [M+H$^+$]: 454.2601. found: 454.2593. HPLC: 100% (t$_R$=5.8 min).

aa. Synthesis of N-(4-(4-((2-Morpholino-2-phenylethyl)amino)quinazolin-2-yl)phenyl)methanesulfonamide (19)

This compound was prepared from 2-chloro-N-(2-morpholino-2-phenylethyl)quinazolin-4-amine and (4-(methylsulfonamido)phenyl)boronic acid according to the procedure described for the preparation of compound 14. Yield 45%. Mp 127-129° C. TLC R$_f$ 0.5 (CH$_2$Cl$_2$-MeOH, 9.6:0.4). $^1$H NMR (400 MHz, DMSO-d$_6$) δ 9.99 (s, 1H), 8.46-8.38 (m, 2H), 8.14-8.07 (m, 2H), 7.78-7.67 (m, 2H), 7.42 (m, 1H), 7.38-7.21 (m, 7H), 4.27 (m, 2H), 4.08-3.87 (m, 2H), 3.54 (t, J=4.6 Hz, 4H), 3.06 (s, 3H), 2.50-2.46 (m, 4H). HRMS m/z calcd for C$_{27}$H$_{29}$N$_5$O$_3$S+H$^+$ [M+H$^+$]: 504.2063. found: 504.2064. HPLC: 96% (t$_R$=5.32 min).

bb. Synthesis of N-(4-(4-((2-Phenyl-2-(pyrrolidin-1-yl)ethyl)amino)quinazolin-2-yl)phenyl)methanesulfonamide (20)

This compound was prepared from 2-chloro-N-(2-phenyl-2-(pyrrolidin-1-yl)ethyl)quinazolin-4-amine and (4-(methylsulfonamido)phenyl)boronic acid according to the procedure described for the preparation of compound 14. Yield 63%. Mp 104-106° C. TLC R$_f$ 0.16 (CH$_2$Cl$_2$-MeOH, 9.6:0.4). $^1$H NMR (400 MHz, DMSO-d$_6$) δ 9.99 (s, 1H), 8.47-8.38 (m, 2H), 8.11-8.02 (m, 2H), 7.73-7.65 (m, 2H), 7.44-7.14 (m, 8H), 4.23 (m, 1H), 3.89-3.71 (m, 2H), 3.07 (s, 3H), 2.64-2.52 (m, 2H), 2.48-2.41 (m, 2H), 1.68 (br s, 4H). HRMS m/z calcd for C$_{27}$H$_{29}$N$_5$O$_2$S+H$^+$ [M+H$^+$]: 488.2114. found: 488.2111. HPLC: 97% (t$_R$=5.16 min).

cc. Synthesis of 2-(4-(Dimethylamino)phenyl)-N-(2-phenyl-2-(pyrrolidin-1-yl)ethyl)quinazolin-4-amine (21)

This compound was prepared from 2-chloro-N-(2-phenyl-2-(pyrrolidin-1-yl)ethyl)quinazolin-4-amine and (4-(dimethylamino)phenyl)boronic acid according to the procedure described for the preparation of compound 14. Yield 66%. Mp 75-77° C. TLC R$_f$ 0.46 (CH$_2$Cl$_2$-MeOH, 9.6:0.4). $^1$H NMR (400 MHz, DMSO-d$_6$) δ 8.38-8.30 (m, 2H), 8.04-7.96 (m, 1H), 7.91 (m, 1H), 7.64-7.51 (m, 2H), 7.36-7.15 (m, 1H), 6.83-6.75 (m, 2H), 4.28-4.16 (m, 1H), 3.86-3.73 (m, 2H), 3.01 (s, 6H), 2.66-2.59 (m, 2H), 2.49-2.41 (m, 2H), 1.69 (m, 4H). HRMS m/z calcd for C$_{28}$H$_{31}$N$_5$O+H$^+$ [M+H$^+$]: 438.2652. found: 438.2647. HPLC: 97% (t$_R$=5.58 min).

dd. Synthesis of 2-(4-(Dimethylamino)phenyl)-N-(2-(4-methylpiperazin-1-yl)-2-phenylethyl)quinazolin-4-amine (22)

This compound was prepared from 2-chloro-N-(2-(4-methylpiperazin-1-yl)-2-phenylethyl)quinazolin-4-amine and (4-(dimethylamino)phenyl)boronic acid according to the procedure described for the preparation of compound 14. Yield 76%. Mp 150-152° C. TLC R$_f$ 0.18 (CH$_2$Cl$_2$-MeOH, 9:1). $^1$H NMR (400 MHz, DMSO-d$_6$) δ 8.37-8.29 (m, 2H), 8.03 (dd, J=8.1, 1.3 Hz, 1H), 7.93 (t, J=5.5 Hz, 1H), 7.72-7.59 (m, 2H), 7.36-7.20 (m, 6H), 6.83-6.74 (m, 2H), 4.24 (ddd, J=13.0, 7.0, 5.3 Hz, 1H), 4.01 (t, J=6.9 Hz, 1H), 3.90 (dt, J=12.4, 6.1 Hz, 1H), 3.00 (s, 6H), 2.34 (br s, 4H), 2.12 (br s, 3H). HRMS m/z calcd for C$_{29}$H$_{34}$N$_6$+H$^+$ [M+H$^+$]: 467.2917. found: 467.2904. HPLC: 100% (t$_R$=5.78 min).

ee. Synthesis of N-(4-(4-((2-(4-Methylpiperazin-1-yl)-2-phenylethyl)amino)quinazolin-2-yl)phenyl)methanesulfonamide (23)

This compound was prepared from 2-chloro-N-(2-(4-methylpiperazin-1-yl)-2-phenylethyl)quinazolin-4-amine and (4-(methylsulfonamido)phenyl)boronic acid according to the procedure described for the preparation of compound 14. Yield 74%. Mp 142-144° C. TLC R$_f$ 0.14 (CH$_2$Cl$_2$-MeOH, 9:1). $^1$H NMR (400 MHz, DMSO-d$_6$) δ 10.00 (s, 1H), 8.43 (dd, J=8.7, 1.2 Hz, 2H), 8.10 (d, J=7.8 Hz, 2H), 7.78-7.66 (m, 2H), 7.48-7.25 (m, 8H), 4.27-3.87 (m, 3H), 3.08 (s, 3H), 2.53-2.29 (m, 8H), 2.19 (s, 3H). HRMS m/z calcd for C$_{28}$H$_{32}$N$_6$O$_2$S+H$^+$ [M+H$^+$]: 517.2380. found: 517.2388. HPLC: 100% (t$_R$=5.29 min).

ff. Synthesis of 2-(4-(Dimethylamino)phenyl)-N-(2-phenyl-2-(pyridin-3-yl)ethyl)quinazolin-4-amine (24)

This compound was prepared from 2-chloro-N-(2 phenyl-2-(pyridin-3-yl)ethyl)quinazolin-4-amine and (4-(dimethylamino)phenyl)boronic acid according to the procedure described for the preparation of compound 14. Yield 58%. Mp 83-85° C. TLC R$_f$ 0.2 (CH$_2$Cl$_2$-MeOH, 9.5:0.5). $^1$H NMR (400 MHz, DMSO-d$_6$) δ 8.64-8.58 (m, 1H), 8.43-8.25 (m, 4H), 8.04 (d, J=8.1 Hz, 1H), 7.85-7.78 (m, 1H), 7.72-7.60 (m, 2H), 7.47-7.40 (m, 2H), 7.39-7.19 (m, 6H), 6.84-6.76 (m, 2H), 4.80 (t, J=7.7 Hz, 1H), 4.31 (m, 2H), 3.01 (s, 6H). HRMS m/z calcd for C$_{29}$H$_{27}$N$_5$+H$^+$ [M+H]$^+$: 446.2339. found: 446.2344. HPLC: 98% (t$_R$=6.36 min).

gg. Synthesis of N-(4-(4-((2-Phenyl-2-(pyridin-3-yl)ethyl)amino)quinazolin-2-yl)phenyl)methanesulfonamide (25)

This compound was prepared from 2-chloro-N-(2 phenyl-2-(pyridin-3-yl)ethyl)quinazolin-4-amine and (4-(methylsulfonamido)phenyl)boronic acid according to the procedure described for the preparation of compound 14. Yield 60%. Mp 105-107° C. TLC R$_f$ 0.14 (CH$_2$Cl$_2$-MeOH, 9.5:0.5). $^1$H NMR (400 MHz, DMSO-d$_6$) δ 10.04 (s, 1H), 8.65-8.59 (m, 1H), 8.49-8.36 (m, 4H), 8.10 (d, J=8.3 Hz, 1H), 7.83 (dt, J=8.0, 2.0 Hz, 1H), 7.77-7.68 (m, 2H), 7.49-7.18 (m, 10H), 4.78 (t, J=7.7 Hz, 1H), 4.33 (m, 2H), 3.07 (s, 3H). HRMS m/z calcd for C$_{28}$H$_{25}$N$_5$O$_2$S+H$^+$ [M+H]$^+$: 496.1801. found: 496.1805. HPLC: 93% (t$_R$=5.75 min).

hh. Synthesis of 2-(4-(Dimethylamino)phenyl)-N-(2,3-diphenylpropyl)quinazolin-4-amine (26)

This compound was prepared from 2-chloro-2,3-diphenylpropyl)quinazolin-4-amine and (4-(dimethylamino)phenyl)boronic acid according to the procedure described for the preparation of compound 14. Yield 68%. Mp 209-211° C. TLC R$_f$ 0.17 (CH$_2$Cl$_2$-EtOAc, 4:1). $^1$H NMR (400 MHz, DMSO-d$_6$) δ 8.33-8.24 (m, 2H), 8.18-8.03 (m, 2H), 7.71-7.57 (m, 2H), 7.37-7.07 (m, 11H), 6.83-6.74 (m, 2H), 3.99-3.79 (m, 2H), 3.62 (p, J=7.4 Hz, 1H), 3.16 (dd, J=13.7, 6.0 Hz, 1H), 3.02 (s, 6H), 2.99-2.95 (m, 1H). FIRMS m/z calcd for C$_{31}$H$_{30}$N$_4$+[M+H$^+$]: 459.2543 found: 459.2544. HPLC: 100% (t$_R$=7.07 min).

ii. Synthesis of N-(4-(4-((2,3-Diphenylpropyl)amino)quinazolin-2-yl)phenyl)methanesulfonamide (27)

This compound was prepared from 2-chloro-2,3-diphenylpropyl)quinazolin-4-amine and 4-(methylsulfonamido)phenylboronic acid according to the procedure described for the preparation of compound 14. Yield 63%. Mp 115-117° C. TLC R$_f$ 0.22 (CH$_2$Cl$_2$-EtOAc, 4:1). $^1$H NMR (400 MHz, DMSO-d$_6$) δ 10.01 (br s, 1H), 8.34-8.32 (m, 2H), 8.25 (t, J=5.4 Hz, 1H), 8.10-8.06 (m, 1H), 7.731-7.70 (m, 2H), 7.41-7.02 (m, 13H), 4.02-3.79 (m, 2H), 3.6 (p, J=7.4 Hz, 1H), 3.15 (dd, J=13.7, 6.0 Hz, 1H), 2.95 (s, 3H), 3.01-2.96 (m, 1H). HRMS m/z calcd for C$_{30}$H$_{28}$N$_4$O$_2$S+H$^+$ [M+H$^+$]: 509.2005 found: 509.2008. HPLC: 100% (t$_R$=6.63 min).

jj. Synthesis of (5-(2-((2-(4-(Dimethylamino)-2-methylphenyl)quinazolin-4-yl)amino)-1-phenylethyl)-1H-pyrrol-2-yl)methanol (28)

i. Step 1
2-Chloro-N-(2-phenyl-2-(1H-pyrrol-2-yl)ethyl)quinazolin-4-amine was reacted with (4-amino-2-methylphenyl)boronic acid using Method B to obtain 2-(4-amino-2-methylphenyl)-N-(2-phenyl-2-(1H-pyrrol-2-yl)ethyl)quinazolin-4-amine.
ii. Step 2
To a solution of the above intermediate (40 mg, 0.095 mmol) and formaldehyde (30.2 mg, 0.372 mmol) in THF (5 mL) was added sodium cyanoborohydride (11.7 mg, 0.186 mmol). The reaction mixture was stirred overnight at room temperature. The solvent was removed under reduced pressure and the crude product was chromatographed (hexanes-EtOAc, 10-50%) to afford 22 mg (48%) of the title compound. Yield 32%. Mp 121-123° C. TLC R$_f$ 0.16 (CH$_2$Cl$_2$-EtOAc, 4:1). $^1$H NMR (400 MHz, DMSO-d$_6$) δ 10.50 (s, 1H), 8.05 (m, 3H), 7.72-7.57 (m, 2H), 7.40-7.13 (m, 6H), 6.70-6.57 (m, 2H), 5.95 (t, J=2.9 Hz, 1H), 5.81 (t, J=2.8 Hz, 1H), 4.71-4.59 (m, 2H), 4.27 (d, J=5.4 Hz, 2H), 4.14-4.00 (m, 2H), 2.97 (s, 6H), 2.67 (s, 3H).

kk. Synthesis of N-(3-Methyl-4-(4-((2-phenyl-2-(pyridin-4-yl)ethyl)amino)quinazolin-2-yl)phenyl)methanesulfonamide (29)

i. Step 1
2-chloro-N-(2-phenyl-2-(pyridin-4-yl)ethyl))quinazolin-4-amine was reacted with (2-methyl-4-amino)phenylboronic acid according to the procedure described for the preparation of compound 14 to obtain 2-(4-amino-2-methylphenyl)-N-(2-phenyl-2-(pyridin-4-yl)ethyl)quinazolin-4-amine.
ii. Step 2
To a cold solution of the above intermediate (0.108 g, 0.25 mmol) in pyridine (4 mL) was added methanesulfonyl chloride (0.03 mL, 0.375 mmol). The reaction mixture was stirred at room temperature for 4 hours. The mixture was partitioned between EtOAc and water and the EtOAc extracts were dried over anhydrous Na$_2$SO$_4$, filtered and the filtrate was concentrated under reduced pressure. The crude product thus obtain was purified by short column chromatography (hexane/EtOAc as eluent) to give the title compound. Yield 50%. Mp 118-120° C. TLC R$_f$ 0.3 (EtOAc). $^1$H NMR (400 MHz, DMSO-d$_6$) δ 9.85 (br s, 1H), 8.48-8.42 (m, 2H), 8.35 (t, J=5.5 Hz, 1H), 8.11 (dd, J=8.2, 1.2 Hz, 1H), 7.94 (d, J=8.4 Hz, 1H), 7.78-7.65 (m, 2H), 7.48-7.27 (m, 7H), 7.27-7.07 (m, 3H), 4.68 (t, J=7.6 Hz, 1H), 4.33-4.15 (m, 2H), 3.04 (s, 3H), 2.51 (s, 3H). HRMS m/z calcd for C$_{29}$H$_{27}$N$_5$O$_2$S+H$^+$ [M+H$^+$]$^+$: 510.1958 found: 510.1959. HPLC: 100% (t$_R$=5.53 min).

ll. Synthesis of N-(4-(4-((2-(Pyridin-3-yl)-2-(1H-pyrrol-2-yl)ethyl)amino)quinazolin-2-yl)phenyl)methanesulfonamide (30)

This compound was prepared from 2-chloro-N-(2-(pyridin-3-yl)-2-(1H-pyrrol-2-yl)ethyl)quinazolin-4-amine and (4-(methylsulfonamido)phenyl)boronic acid according to the procedure described for the preparation of compound 2. Yield 43%. Mp 164-166° C. TLC R$_f$ 0.28 (CHCl$_3$-MeOH, 92.5:7.5). H NMR (400 MHz, DMSO-d$_6$) δ 10.74 (s, 1H), 10.02 (s, 1H), 8.77-7.99 (m, 6H), 7.92-7.54 (m, 3H), 7.60-7.07 (m, 4H), 6.79-6.45 (m, 1H), 6.37-5.83 (m, 2H), 4.77 (dd, J=8.4, 7.1 Hz, 1H), 4.49-4.00 (m, 2H), 3.08 (d, J=0.6 Hz, 3H). HRMS m/z calcd for C$_{26}$H$_{24}$N$_6$O$_2$S+H$^+$ [M+H]$^+$: 485.1754. found: 485.1758. HPLC: 99% (t$_R$=5.7 min).

mm. Synthesis of 2-(4-(Dimethylamino)phenyl)-N-(2-(pyridin-3-yl)-2-(1H-pyrrol-2-yl)ethyl)quinazolin-4-amine (31)

This compound was prepared from 2-chloro-N-(2-(pyridin-3-yl)-2-(1H-pyrrol-2-yl)ethyl)quinazolin-4-amine and (4 (4-(dimethylamino)phenyl)boronic acid according to the procedure described for the preparation of compound 2. Yield 27%. Mp 188-90° C. TLC R$_f$ 0.27 (CHCl$_3$-MeOH, 92.5:7.5). $^1$H NMR (400 MHz, DMSO-d$_6$) δ 10.72 (s, 1H), 8.48 (dd, J=2.2, 1.1 Hz, 1H), 8.40-8.32 (m, 3H), 8.21 (t, J=5.6 Hz, 1H), 8.05 (dd, J=8.1, 1.0 Hz, 1H), 7.65 (ddt, J=8.6, 7.7, 1.2 Hz, 3H), 7.38-7.24 (m, 2H), 6.84-6.76 (m, 2H), 6.65 (dq, J=2.5, 1.3 Hz, 1H), 6.13 (dt, J=3.2, 1.8 Hz, 1H), 5.99 (q, J=2.8 Hz, 1H), 4.77 (t, J=7.8 Hz, 1H), 4.27-4.13 (m, 2H), 3.01 (d, J=0.9 Hz, 6H). HRMS m/z calcd for C$_{27}$H$_{26}$N$_6$+H$^+$ [M+H$^+$]: 435.2292. found: 435.2294. HPLC: 98% (t$_R$=6.0 min).

nn. Synthesis of N-(4-(4-((2-(Pyridin-2-yl)-2-(1H-pyrrol-2-yl)ethyl)amino)quinazolin-2-yl)phenyl)methanesulfonamide (32)

This compound was prepared from 2-chloro-N-(2-(pyridin-2-yl)-2-(1H-pyrrol-2-yl)ethyl)quinazolin-4-amine and (4-(methylsulfonamido)phenyl)boronic acid according to the procedure described for the preparation of compound 2. Yield 43%. Mp 180-4° C. TLC R$_f$ 0.39 (CHCl$_3$-MeOH, 92.5:7.5). $^1$H NMR (400 MHz, DMSO-d$_6$) δ 10.68 (s, 1H), 10.00 (s, 1H), 8.59-8.52 (m, 1H), 8.51-8.46 (m, 2H), 8.37-8.32 (m, 1H), 8.31 (d, J=0.9 Hz, 1H), 8.11 (dt, J=8.4, 1.0 Hz, 1H), 7.74-7.70 (m, 2H), 7.67 (td, J=7.7, 1.9 Hz, 1H), 7.40 (ddd, J=8.2, 4.7, 3.5 Hz, 1H), 7.34-7.29 (m, 2H), 7.26 (dt, J=7.9, 1.1 Hz, 1H), 7.20 (ddd, J=7.6, 4.8, 1.1 Hz, 1H), 6.62 (td, J=2.6, 1.5 Hz, 1H), 6.08-5.68 (m, 2H), 4.89 (t, J=7.4 Hz, 1H), 4.37 (ddd, J=13.1, 8.0, 5.5 Hz, 1H), 3.07 (s, 3H). HRMS m/z calcd for C$_{26}$H$_{24}$N$_6$O$_2$S+H$^+$ [M+H$^+$]: 485.1754. found: 485.1758. HPLC: 100% (t$_R$=5.7 min).

oo. Synthesis of 2-(4-(Dimethylamino)phenyl)-N-(2-(pyridin-2-yl)-2-(1H-pyrrol-2-yl)ethyl)quinazolin-4-amine (33)

This compound was prepared from 2-chloro-N-(2-(pyridin-2-yl)-2-(1H-pyrrol-2-yl)ethyl)quinazolin-4-amine and ((4-(dimethylamino)phenyl)boronic acid according to the procedure described for the preparation of compound 2. Yield 47%. Mp 125-127° C. TLC $R_f$ 0.44 (CHCl$_3$-MeOH, 92.5:7.5), $^1$H NMR (400 MHz, DMSO-d$_6$) δ 10.66 (d, J=3.4 Hz, 1H), 8.55 (ddt, J=4.9, 1.9, 0.8 Hz, 1H), 8.43-8.34 (m, 2H), 8.31 (d, J=0.6 Hz, 1H), 8.17 (t, J=5.5 Hz, 1H), 7.73-7.57 (m, 3H), 7.31 (ddd, J=8.2, 6.0, 2.1 Hz, 1H), 7.26-7.15 (m, 2H), 6.83-6.70 (m, 2H), 6.61 (ddd, J=4.2, 2.1, 1.3 Hz, 1H), 6.03 (td, J=3.1, 1.9 Hz, 1H), 5.98-5.89 (m, 1H), 4.89 (t, J=7.5 Hz, 1H), 4.40-4.28 (m, 1H), 4.24-4.05 (m, 1H), 3.11-2.88 (m, 6H). HRMS m/z calcd for C$_{27}$H$_{26}$N$_6$+H$^+$ [M+H$^+$]: 435.2288. found: 435.2289. HPLC: 100% ($t_R$=6.3 min).

pp. Synthesis of N-(2,2-Di(pyridin-4-yl)ethyl)-2-(4-(dimethylamino)phenyl)quinazolin-4-amine (34)

This compound was prepared from 2-chloro-N-(2,2-di(pyridin-4-yl)ethyl)quinazolin-4-amine and (4-(dimethylamino)phenyl)boronic acid according to the procedure described for the preparation of compound 2. Yield 54%. Mp 200-203° C. TLC $R_f$ 0.37 (CHCl$_3$-MeOH, 92.5:7.5), $^1$H NMR (400 MHz, DMSO-d$_6$) δ 8.55-8.45 (m, 4H), 8.36-8.27 (m, 3H), 8.06-8.00 (m, 1H), 7.71-7.62 (m, 2H), 7.47-7.40 (m, 4H), 7.34 (ddd, J=8.2, 6.1, 2.1 Hz, 1H), 6.79 (d, J=9.0 Hz, 2H), 4.77 (t, J=7.4 Hz, 1H), 4.44-4.06 (m, 2H), 3.01 (s, 6H). HRMS m/z calcd for C$_{28}$H$_{26}$N$_6$+H$^+$ [M+H$^+$]: 447.2292. found: 447.2295. HPLC: 100% ($t_R$=5.8 min).

qq. Synthesis of N-(4-(4-((2,2-Di(pyridin-4-yl)ethyl)amino)quinazolin-2-yl)phenyl)methanesulfonamide (35)

This compound was prepared from 2-chloro-N-(2,2-di(pyridin-4-yl)ethyl)quinazolin-4-amine and (4-(methylsulfonamido)phenyl)boronic acid according to the procedure described for the preparation of compound 2. Yield 47%. Mp 218-220° C. TLC $R_f$ 0.27 (CHCl$_3$-MeOH, 92.5:7.5), $^1$H NMR (400 MHz, DMSO-d$_6$) δ 10.01-10.22 (s, 1H), 8.54-8.46 (m, 4H), 8.47-8.39 (m, 2H), 8.09 (d, J=8.2 Hz, 1H), 7.78-7.64 (m, 2H), 7.51-7.45 (m, 3H), 7.44-7.37 (m, 3H), 7.29 (d, J=8.5 Hz, 2H), 5.00-4.64 (m, 1H), 4.34 (t, J=6.4 Hz, 2H), 3.05 (s, 3H). HRMS m/z calcd for C$_{27}$H$_{24}$N$_6$O$_2$S+H$^+$ [M+H$^+$]: 497.1454. found: 49.1753. HPLC: 99% ($t_R$=5.5 min).

rr. Synthesis of 2-(4-(Dimethylamino)phenyl)-N-phenethylquinazolin-4-amine (36)

This compound was prepared from 2-chloro-N-phenethylquinazolin-4-amine and (4-(dimethylamino)phenyl)boronic acid according to the procedure described for the preparation of compound 2. Yield 42%. Mp 150-152° C. TLC $R_f$ 0.27 (CHCl$_3$-MeOH, 92.5:7.5), $^1$H NMR (400 MHz, DMSO-d$_6$) δ 8.40-8.33 (m, 2H), 8.27 (s, 1H), 8.15 (dt, J=8.4, 0.9 Hz, 1H), 7.74-7.62 (m, 2H), 7.38 (s, 1H), 7.34-7.30 (m, 4H), 7.25-7.18 (m, 1H), 6.84-6.76 (m, 2H), 3.90-3.80 (m, 2H), 3.11-3.03 (m, 2H), 3.00 (d, J=1.0 Hz, 6H). HRMS m/z calcd for C$_{24}$H$_{24}$N$_4$+H$^+$ [M+H+]: 369.2073. found: 369.2071. HPLC: 99% ($t_R$=6.7 min).

ss. Synthesis of N-(4-(4-(Phenethylamino)quinazolin-2-yl)phenyl)methanesulfonamide (37)

This compound was prepared from 2-chloro-N-phenethylquinazolin-4-amine and (4-(methylsulfonamido)phenyl)boronic acid according to the procedure described for the preparation of compound 2. Yield 32%. Mp 232-236° C. TLC $R_f$ 0.37 (CHCl$_3$-MeOH, 92.5:7.5). $^1$H NMR (400 MHz, DMSO-d$_6$) δ 10.00 (s, 1H), 8.48-8.44 (m, 2H), 8.41 (s, 1H), 8.21 (dt, J=8.3, 1.0 Hz, 1H), 7.76-7.72 (m, 4H), 7.46 (ddd, J=8.2, 5.3, 2.8 Hz, 1H), 7.36-7.28 (m, 5H), 4.35-3.70 (m, 2H), 3.07 (s, 5H). HRMS m/z calcd for C$_{23}$H$_{22}$N$_4$O$_2$S+H$^+$ [M+H$^+$]: 419.1536. found: 419.1540. HPLC: 100% ($t_R$=6.2 min).

tt. Synthesis of 2-(4-(Dimethylamino)phenyl)-N-(2,2-diphenylpropyl)quinazolin-4-amine (38)

This compound was prepared 2-chloro-N-(2,2-diphenylpropyl)quinazolin-4-amine and (4-(dimethylamino)phenyl)boronic acid according to the procedure described for the preparation of compound 2. Yield 21%. Mp 160-162° C. TLC $R_f$ 0.81 (CHCl$_3$-MeOH, 90:10). $^1$H NMR (400 MHz, DMSO-d$_6$) δ 8.35-8.26 (m, 2H), 8.10-7.99 (m, 1H), 7.63 (d, J=1.6 Hz, 1H), 7.39-7.22 (m, 8H), 7.21-7.08 (m, 4H), 6.79 (d, J=9.0 Hz, 2H), 4.52 (d, J=6.0 Hz, 2H), 3.57 (s, 1H), 2.99 (s, 6H), 1.82 (s, 3H). HRMS m/z calcd for C$_{31}$H$_{30}$N$_4$+H$^+$ [M+H$^+$]: 459.2543. found: 459.2546. HPLC: 99% ($t_R$=7.3 min).

uu. Synthesis of N-(4-(4-((2,2-Diphenylpropyl)amino)quinazolin-2-yl)phenyl)methanesulfonamide (39)

This compound was prepared 2-chloro-N-(2,2-diphenylpropyl)quinazolin-4-amine and (4-(methylsulfonamido)phenyl)boronic acid according to the procedure described for the preparation of compound 2. Yield 17%. Mp 160-163° C. TLC $R_f$ 0.62 (CHCl$_3$-MeOH, 90:10). $^1$H NMR (400 MHz, DMSO-d$_6$) δ 9.97 (s, 1H), 8.44-8.35 (m, 2H), 8.31 (d, J=0.5 Hz, 1H), 8.16-8.04 (m, 1H), 7.79-7.55 (m, 2H), 7.48-7.20 (m, 11H), 7.19-7.08 (m, 2H), 4.54 (d, J=5.9 Hz, 2H), 3.07 (d, J=0.8 Hz, 3H), 1.82 (s, 3H). HRMS m/z calcd for C$_{30}$H$_{28}$N$_4$O$_2$S+H$^+$ [M+H$^+$]: 509.2003. found: 509.2004. HPLC: 99% ($t_R$=7.1 min).

vv. Synthesis of 2-(4-(Dimethylamino)phenyl)-N-(1,2-diphenylethyl)quinazolin-4-amine (40)

This compound was prepared from 2-chloro-N-(1,2-diphenylethyl)quinazolin-4-amine and (4-(dimethylamino)phenyl)boronic acid according to the procedure described for the preparation of compound 2. Yield 16%. Mp 213-214° C. TLC $R_f$ 0.63 (CHCl$_3$-MeOH, 90:10). $^1$H NMR (400 MHz, DMSO-d$_6$) δ 8.43 (d, J=7.9 Hz, 1H), 8.39-8.34 (m, 1H), 8.23 (d, J=8.9 Hz, 1H), 7.65-7.55 (m, 6H), 7.45-7.27 (m, 6H), 7.21 (d, J=7.7 Hz, 1H), 7.12 (d, J=7.3 Hz, 1H), 6.76 (d, J=9.0 Hz, 2H), 5.81 (td, J=9.1, 5.6 Hz, 1H), 3.41 (dd, J=13.8, 9.8 Hz, 1H), 3.19 (dd, J=13.8, 5.6 Hz, 1H), 2.98 (s, 6H). HRMS m/z calcd for C$_{30}$H$_{28}$N$_4$+H$^+$ [M+H$^+$]: 445.2026. found: 445.2028. HPLC: 99% ($t_R$=6.9 min).

ww. Synthesis of N-(4-(4-((1,2-Diphenylethyl)amino)quinazolin-2-yl)phenyl)methanesulfonamide (41)

This compound was prepared from 2-chloro-N-(1,2-diphenylethyl)quinazolin-4-amine and (4-(methylsulfonamido)phenyl)boronic acid according to the procedure described for the preparation of compound 2. Yield 44%. Mp 179-182° C. TLC $R_f$ 0.57 (CHCl$_3$-MeOH, 90:10), $^1$H NMR (400 MHz, DMSO-d$_6$) δ 8.56 (d, J=8.1 Hz, 1H), 8.46-8.38 (m, 1H), 8.37-8.27 (m, 3H), 7.78-7.65 (m, 2H), 7.64-7.57 (m, 2H), 7.49 (ddd, J=8.3, 6.7, 1.4 Hz, 1H), 7.42-7.04 (m, 10H), 5.84 (ddd, J=9.9, 7.9, 5.4 Hz, 1H), 3.41 (dd, J=13.8, 9.9 Hz, 1H), 3.20 (dd, J=13.8, 5.5 Hz, 1H), 3.05 (s, 3H). HRMS m/z calcd for C$_{29}$H$_{26}$N$_4$O$_2$S+H$^+$ [M+H$^+$]: 495.1849. found: 495.1844. HPLC: 99% (t$_R$=6.5 min).

xx. Synthesis of N-(4-(4-((1,3-Diphenylpropyl) amino)quinazolin-2-yl)phenyl)methanesulfonamide (42)

This compound was prepared from 2-chloro-N-(1,3-diphenylpropyl)quinazolin-4-amine and (4-(methylsulfonamido)phenyl)boronic acid according to the procedure described for the preparation of compound 2. Yield 65%. Mp 100-102° C. TLC $R_f$ 0.56 (CHCl$_3$-MeOH, 90:10). $^1$H NMR (400 MHz, DMSO-d$_6$) δ 9.98 (s, 1H), 8.60-8.42 (m, 2H), 8.38-8.24 (m, 2H), 7.83-7.67 (m, 2H), 7.59-7.43 (m, 3H), 7.41-7.08 (m, 11H), 5.91-5.35 (m, 1H), 3.06 (s, 3H), 2.79 (dd, J=9.1, 5.2 Hz, 1H), 2.66 (ddd, J=13.7, 9.2, 6.4 Hz, 1H), 2.41 (dd, J=9.0, 4.9 Hz, 1H). HRMS m/z calcd for C$_{30}$H$_{28}$N$_4$O$_2$S+H$^+$ [M+H$^+$]: 509.2005. found: 509.2006. HPLC: 98% (t$_R$=6.6 min).

yy. Synthesis of 2-(4-(Dimethylamino)phenyl)-N-(1,3-diphenylpropyl)quinazolin-4-amine (43)

This compound was prepared from 2-chloro-N-(1,3-diphenylpropyl)quinazolin-4-amine and N,N-dimethyl-4-(4,4,5,5-tetramethyl-1,3,2-dioxaborolan-2-yl)aniline according to the procedure described for the preparation of compound 2. Yield 41%. Mp 192-194° C. TLC $R_f$ 0.65 (CHCl$_3$-MeOH, 90:10). $^1$H NMR (400 MHz, DMSO-d$_6$) δ 8.46-8.35 (m, 2H), 8.28-8.19 (m, 2H), 7.76-7.49 (m, 5H), 7.42 (ddd, J=8.2, 6.7, 1.5 Hz, 1H), 7.37-7.13 (m, 7H), 6.80-6.71 (m, 2H), 5.61 (td, J=8.5, 5.8 Hz, 1H), 2.99 (s, 6H), 2.80 (ddd, J=14.6, 9.5, 5.7 Hz, 1H), 2.66 (ddd, J=13.7, 9.2, 6.4 Hz, 1H), 2.41 (dtd, J=13.3, 9.3, 5.6 Hz, 1H), 2.18 (ddt, J=13.2, 9.6, 6.2 Hz, 1H). HRMS m/z calcd for C$_{31}$H$_{30}$N$_4$+H$^+$ [M+H$^+$]: 459.2543. found: 459.2539. HPLC: 99% (t$_R$=7.7 min).

zz. Synthesis of 2-(4-(Dimethylamino)phenyl)-N-(3-methyl-2-phenylbutyl)quinazolin-4-amine (44)

This compound was prepared from 2-chloro-N-(3-methyl-2-phenylbutyl)quinazolin-4-amine and N,N-dimethyl-4-(4,4,5,5-tetramethyl-1,3,2-dioxaborolan-2-yl)aniline according to the procedure described for the preparation of compound 2. Yield 50%. Mp 186-188° C. TLC $R_f$ 0.76 (CHCl$_3$-MeOH, 90:10). $^1$H NMR (400 MHz, DMSO-d$_6$) δ 8.39-8.31 (m, 2H), 8.05-7.91 (m, 2H), 7.69-7.57 (m, 2H), 7.34-7.12 (m, 6H), 6.83-6.74 (m, 2H), 4.18 (dt, J=12.2, 5.8 Hz, 1H), 3.83 (ddd, J=13.8, 8.3, 5.8 Hz, 1H), 3.11 (dt, J=8.4, 6.4 Hz, 1H), 3.01 (s, 6H), 2.04 (h, J=6.7 Hz, 1H), 1.05 (d, J=6.7 Hz, 3H), 0.79 (d, J=6.7 Hz, 3H). HRMS m/z calcd for C$_{27}$H$_{30}$N$_4$+H$^+$ [M+H$^+$]: 411.2543. found: 411.2539. HPLC: 100% (t$_R$=7.0 min).

aaa. Synthesis of N-(4-(4-((3-Methyl-2-phenylbutyl) amino)quinazolin-2-yl)phenyl)methanesulfonamide (45)

This compound was prepared from 2-chloro-N-(3-methyl-2-phenylbutyl)quinazolin-4-amine and (4-(methyl-sulfonamido)phenyl)boronic acid according to the procedure described for the preparation of compound 2. Yield 44%. Mp 107-108° C. TLC $R_f$ 0.62 (CHCl$_3$-MeOH, 90:10), $^1$H NMR (400 MHz, DMSO-d$_6$) δ 10.01 (s, 1H), 8.49-8.40 (m, 2H), 8.15-8.03 (m, 2H), 7.75-7.65 (m, 2H), 7.44-7.11 (m, 8H), 4.18 (dt, J=13.2, 5.7 Hz, 1H), 3.86 (ddd, J=13.2, 8.7, 5.9 Hz, 1H), 3.07 (d, J=0.8 Hz, 4H), 2.11-1.96 (m, 1H), 1.08 (dd, J=19.3, 6.8 Hz, 3H), 0.78 (d, J=6.7 Hz, 3H). HRMS m/z calcd for C$_{26}$H$_{28}$N$_4$O$_2$S+H$^+$ [M+H$^+$]: 461.2005. found: 461.2002. HPLC: 99.% (t$_R$=6.5 min).

bbb. Synthesis of (1R,2S)-2-(((2-(4-(Dimethyl-amino)phenyl)quinazolin-4-yl)amino)methyl)-N,N-diethyl-1-phenylcyclopropanecarboxamide (46)

This compound was prepared from (1R)-2-(((2-chloro-quinazolin-4-yl)amino)methyl)-N,N-diethyl-1-phenylcyclopropanecarboxamide and (4-(dimethylamino)phenyl)boronic acid according to the procedure described for the preparation of compound 2. Yield 16%. Mp 88-89° C. TLC $R_f$ 0.58 (CHCl$_3$-MeOH, 90:10). $^1$H NMR (400 MHz, DMSO-d$_6$) δ 8.40-8.26 (m, 4H), 8.17 (d, J=8.2 Hz, 1H), 7.78-7.62 (m, 2H), 7.40 (t, J=1.7 Hz, 1H), 7.37-7.28 (m, 2H), 7.28-7.16 (m, 4H), 6.82-6.70 (m, 2H), 3.90 (s, 1H), 3.12 (ddd, J=14.2, 12.0, 6.9 Hz, 2H), 3.00 (s, 6H), 2.41-2.25 (m, 1H), 1.59 (dd, J=6.3, 4.6 Hz, 1H), 1.24 (s, 1H), 1.12-0.91 (m, 4H), 0.57 (t, J=7.0 Hz, 3H). HRMS m/z calcd for C$_{31}$H$_{35}$N$_5$O+H$^+$ [M+H$^+$]: 494.2914. found: 494.2919. HPLC: 100% (t$_R$=6.9 min).

ccc. Synthesis of N-(4-(4-((2,2-Di(pyridin-4-yl) ethyl)amino)quinazolin-2-yl)-3-methylphenyl)methanesulfonamide (47)

This compound was prepared from 2-chloro-N-(2,2-di (pyridin-4-yl)ethyl)quinazolin-4-amine and (2-methyl-4-(methylsulfonamido)phenyl)boronic acid according to the procedure described for the preparation of compound 2. Yield 32%. Mp 212-214° C. TLC $R_f$ 0.72 (CHCl$_3$-MeOH, 90:10). $^1$H NMR (400 MHz, DMSO-d$_6$) δ 9.85 (s, 1H), 8.56-8.46 (m, 4H), 8.38 (t, J=5.5 Hz, 1H), 8.11 (d, J=8.3 Hz, 1H), 7.94 (d, J=8.4 Hz, 1H), 7.79-7.63 (m, 2H), 7.51-7.34 (m, 6H), 4.68 (t, J=7.5 Hz, 1H), 4.26 (dd, J=7.5, 5.3 Hz, 2H), 3.57 (d, J=0.6 Hz, 3H), 3.03 (s, 3H), 1.24 (s, 1H). HRMS m/z calcd for C$_{28}$H$_{26}$N$_6$O$_2$S+H$^+$ [M+H]$^+$ 511.1910. found: 511.1905. HPLC: 98% (t$_R$=4.5 min).

ddd. Synthesis of 2-(4-(Dimethylamino)phenyl)-N-(2-phenoxy-2-phenylethyl)quinazolin-4-amine (48)

This compound was prepared from 2-chloro-N-(2-phenoxy-2-phenylethyl)quinazolin-4-amine and (4-(dimethylamino)phenyl)boronic acid according to the procedure described for the preparation of compound 2. Yield 53%. Mp 190-192° C. TLC $R_f$ 0.82 (CHCl$_3$-MeOH, 90:10). $^1$H NMR (400 MHz, DMSO-d$_6$) δ 8.52 (t, J=5.6 Hz, 1H), 8.40-8.26 (m, 2H), 8.25-8.14 (m, 1H), 7.79-7.62 (m, 2H), 7.58-7.47 (m, 2H), 7.46-7.26 (m, 3H), 7.22-7.06 (m, 4H), 6.94-6.67 (m, 3H), 5.79 (dd, J=8.1, 4.3 Hz, 1H), 4.20-4.05 (m, 1H), 4.04-3.90 (m, 1H), 3.01 (s, 6H). HRMS m/z calcd for C$_{30}$H$_{28}$N$_4$O+H$^+$ [M+H$^+$]: 461.2335. found: 461.2346. HPLC: 100% (t$_R$=6.9 min).

eee. Synthesis of N-(4-(4-((2-Phenoxy-2-phenyl-ethyl)amino)quinazolin-2-yl)phenyl)methanesulfonamide (49)

This compound was prepared from 2-chloro-N-(2-phenoxy-2-phenylethyl)quinazolin-4-amine and (4-(methylsulfonamido)phenyl)boronic acid using Method B. Yield 33%. Mp 114-116° C. TLC $R_f$ 0.66 (CHCl$_3$-MeOH, 90:10). $^1$H NMR (400 MHz, DMSO-d$_6$) δ 10.02 (s, 1H), 8.64 (t, J=5.6 Hz, 1H), 8.48-8.40 (m, 2H), 8.33-8.22 (m, 1H), 7.80-7.71 (m, 2H), 7.56-7.26 (m, 8H), 7.21-7.10 (m, 2H), 6.94-6.79 (m, 3H), 5.78 (dd, J=7.8, 4.6 Hz, 1H), 4.17-3.95 (m, 2H), 3.07 (s, 3H). HRMS m/z calcd for C$_{29}$H$_{26}$N$_4$O$_3$S+H$^+$ [M+H$^+$]: 511.1798. found: 511.1795. HPLC: 100% (t$_R$=6.4 min).

3. Assay for Dopamine Reuptake Inhibition

Uptake inhibition assay for the dopamine transporter was conducted in rat brain synaptosomes as described elsewhere with minor modifications (Rothman et al., *Synapse* 39, 32-41 (2001)). Freshly removed caudate was homogenized in 10% ice-cold sucrose with 12 strokes of a hand-held Potter-Elvehjem homogenizer followed by centrifugation at 1000×g for 10 min. The supernatants were saved on ice and used immediately. Transporter activity was assessed using 5 nM [$^3$H]dopamine. The assay buffer was Krebs-phosphate buffer containing 154.4 mM NaCl, 2.9 mM KCl, 1.1 mM CaCl$_2$, 0.83 mM MgCl$_2$, 5 mM glucose, 1 mg/mL ascorbic acid, and 50 µM pargyline. The selectivity of the uptake assay for DAT was optimized by including 100 nM citalopram and 100 nM desipramine as blockers of SERT and NET in the sucrose solution and assay buffer. Uptake inhibition assays were conducted at 25° C. and were initiated by adding 100 µl of tissue to 900 µL assay buffer containing test drug and [$^3$H]dopamine. Test drugs were diluted in assay buffer containing 1 mg/mL bovine serum albumin. Nonspecific uptake was measured by incubating in the presence of 10 µM indatraline. The reactions were stopped after 15 minutes by rapid vacuum filtration with a cell harvester (BRANDEL) over GF/B filters (Whatman) presoaked in wash buffer maintained at 25° C. (10 mM Tris-HCl, pH 7.4/150 mM NaCl). Filters were rinsed with 6 mL wash buffer and retained tritium was quantified by a MicroBeta liquid scintillation counter (PerkinElmer) after overnight extraction in 0.6 mL of liquid scintillation cocktail (Cytoscint, ICN). The data from three experiments were pooled and fit to a dose-response curve equation (using Kaleidagraph), to yield an $E_{max}$ and EC$_{50}$ value. The dopamine uptake inhibition potency and efficacy of the compounds are shown in Table 2. The compound numbers in Table 2 correspond to the respective compound numbers given in Table 1 and in the Examples.

TABLE 2

| No. | DA Uptake EC$_{50}$ (nM ± SD) | DA Uptake E$_{max}$ (% I ± SD) |
| --- | --- | --- |
| 1 | 380 | 100 |
| 2 | 50 ± 10 | 90 ± 3 |
| 3 | 22 ± 6 | 91 ± 4 |
| 4 | 11 ± 2 | 70 ± 2 |
| 5 | 6.7 ± 1.4 | 74 ± 2 |
| 6 | 16 ± 2 | 75 ± 2 |
| 7 | 46 ± 10 | 71 ± 3 |
| 8 | 477 ± 75 | 88 ± 3 |
| 9 | 117 ± 22 | 91 ± 3 |
| 10 | 4.8 ± 0.6 | 71 ± 1 |
| 11 | 13 ± 3 | 77 ± 2 |
| 12 | 100 ± 22 | 70 ± 3 |
| 13 | 138 ± 21 | 86 ± 3 |
| 14 | 5.6 ± 2.1 | 77 ± 4 |
| 15 | 43 ± 8 | 63 ± 2 |
| 16 | 34 ± 9 | 88 ± 4 |
| 17 | 62 ± 20 | 83 ± 5 |

TABLE 2-continued

| No. | DA Uptake EC$_{50}$ (nM ± SD) | DA Uptake E$_{max}$ (% I ± SD) |
| --- | --- | --- |
| 18 | 15 ± 7 | 75 ± 5 |
| 19 | 43 ± 13 | 71 ± 4 |
| 20 | 160 ± 51 | 79 ± 5 |
| 21 | 112 ± 26 | 92 ± 4 |
| 22 | 30 ± 8 | 91 ± 4 |
| 23 | 62 ± 15 | 77 ± 3 |
| 24 | 24 ± 5 | 79 ± 3 |
| 25 | 25 ± 4 | 73 ± 2 |
| 26 | 39 ± 9 | 78 ± 3 |
| 27 | 58 ± 9 | 76 ± 2 |
| 28 | 18 ± 7 | 84 ± 5 |
| 29 | 7.4 ± 2 | 74 ± 4 |
| 30 | 202 ± 42 | 79 ± 3 |
| 31 | 47 ± 12 | 85 ± 4 |
| 32 | 379 ± 80 | 73 ± 3 |
| 33 | 65 ± 18 | 89 ± 4 |
| 34 | 21 ± 5 | 78 ± 3 |
| 35 | 47 ± 10 | 70 ± 2 |
| 36 | 156 ± 12 | 100 ± 1 |
| 37 | 159 ± 54 | 86 ± 6 |
| 38 | 15 ± 4 | 68 ± 3 |
| 39 | 16 ± 3 | 67 ± 2 |
| 40 | 40 ± 8 | 72 ± 2 |
| 41 | 50 ± 14 | 69 ± 3 |
| 42 | 71 ± 11 | 72 ± 2 |
| 43 | 75 ± 22 | 70 ± 4 |
| 44 | 30 ± 10 | 84 ± 5 |
| 45 | 20 ± 6 | 78 ± 4 |
| 46 | 243 ± 18 | 93 ± 1 |
| 47 | 84 ± 25 | 67 ± 4 |
| 48 | 42 ± 10 | 72 ± 3 |
| 49 | 30 ± 5 | 67 ± 2 |

4. Assay for Serotonin Reuptake Inhibition

Uptake inhibition assay for the serotonin transporter was conducted in rat brain synaptosomes as described elsewhere with minor modifications (Rothman et al., *Synapse* 39, 32-41 (2001)). Freshly removed whole brain minus cerebellum and caudate was homogenized in 10% ice-cold sucrose with 12 strokes of a hand-held Potter-Elvehjem homogenizer followed by centrifugation at 1000×g for 10 min. The supernatants were saved on ice and used immediately. Transporter activity at SERT was assessed using 5 nM [$^3$H]serotonin. The assay buffer was Krebs-phosphate buffer containing 154.4 mM NaCl, 2.9 mM KCl, 1.1 mM CaCl$_2$, 0.83 mM MgCl$_2$, 5 mM glucose, 1 mg/mL ascorbic acid, and 50 µM pargyline. The sucrose solution and assay buffer contained 50 nM GBR12935 and 100 nM nomifensine to prevent uptake of [$^3$H]serotonin by DAT and NET, respectively. Uptake inhibition assays were conducted at 25° C. and were initiated by adding 100 µL of tissue to 900 µL assay buffer containing test drug and [$^3$H]serotonin. Test drugs were diluted in assay buffer containing 1 mg/mL bovine serum albumin. Nonspecific uptake was measured by incubating in the presence of 10 µM indatraline. The reactions were stopped after 30 min by rapid vacuum filtration with a cell harvester (BRANDEL) over GF/B filters (Whatman) presoaked in wash buffer maintained at 25° C. (10 mM Tris-HCl, pH 7.4/150 mM NaCl). Filters were rinsed with 6 mL wash buffer and retained tritium was quantified by a MicroBeta liquid scintillation counter (PerkinElmer) after overnight extraction in 0.6 mL of liquid scintillation cocktail (Cytoscint, ICN). The data from three experiments were pooled and fit to a dose-response curve equation (using Kaleidagraph), to yield an $E_{max}$ and EC$_{50}$ value. The serotonin uptake inhibition potency and efficacy of the compounds are shown in Table 3. The compound numbers in Table 3 correspond to the respective compound numbers given in Table 1 and in the Examples.

TABLE 3

| Compd # | 5HT Uptake $EC_{50}$ (nM ± SD) | 5HT Uptake $E_{max}$ (% I ± SD) |
|---|---|---|
| 4 | 50 ± 14 | 55 ± 3 |
| 10 | 8.7 ± 0.9 | 56 ± 1 |
| 29 | 8.0 ± 2.8 | 58 ± 3 |

5. Assay for Norepinephrine Reuptake Inhibition

Uptake inhibition assay for the norepinephrine transporter was conducted in rat brain synaptosomes as described elsewhere with minor modifications (Rothman et al., *Synapse* 39, 32-41 (2001)). Freshly removed whole brain minus cerebellum and caudate was homogenized in 10% ice-cold sucrose with 12 strokes of a hand-held Potter-Elvehjem homogenizer followed by centrifugation at 1000×g for 10 minutes. The supernatants were saved on ice and used immediately. Transporter activity at NET was assessed using 10 nM [$^3$H]norepinephrine. The assay buffer was Krebs-phosphate buffer containing 154.4 mM NaCl, 2.9 mM KCl, 1.1 mM $CaCl_2$, 0.83 mM $MgCl_2$, 5 mM glucose, 1 mg/mL ascorbic acid, and 50 µM pargyline. The sucrose solution and assay buffer contained 50 nM GBR12935 to prevent uptake of [$^3$H]norepinephrine by DAT. Uptake inhibition assays were conducted at 37° C. and were initiated by adding 100 µL of tissue to 900 µL assay buffer containing test drug and [$^3$H]norepinephrine. Test drugs were diluted in assay buffer containing 1 mg/mL bovine serum albumin. Nonspecific uptake was measured by incubating in the presence of 10 µM indatraline. The reactions were stopped after 10 minutes by rapid vacuum filtration with a cell harvester (BRANDEL) over GF/B filters (Whatman) pre-soaked in wash buffer maintained at 25° C. (10 mM Tris-HCl, pH 7.4/150 mM NaCl). Filters were rinsed with 6 mL wash buffer and retained tritium was quantified by a Micro-Beta liquid scintillation counter (PerkinElmer) after overnight extraction in 0.6 mL of liquid scintillation cocktail (Cytoscint, ICN). The data from three experiments were pooled and fit to a dose-response curve equation (using Kaleidagraph), to yield an $E_{max}$ and $EC_{50}$ value. The norepinephrine uptake inhibition potency and efficacy of the compounds are shown in Table 4. The compound numbers in Table 4 correspond to the respective compound numbers given in Table 1 and in the Examples.

TABLE 4

| Compd # | NE Uptake $EC_{50}$ (nM ± SD) | NE Uptake $E_{max}$ (% I ± SD) |
|---|---|---|
| 4 | 426 ± 49 | 70 ± 2 |
| 10 | 44 ± 6 | 76 ± 2 |
| 29 | 31 ± 7 | 71 ± 3 |

6. Assay for Dopamine Transporter-Mediated Release

Dopamine transporter-mediated release assays were carried out as previously described with minor modifications (Rothman et al., *J. Pharmacol. Exp. Ther.* 307, 138-145 (2003)). Synaptosomes were prepared from rat caudate tissue as described for uptake inhibition assays, except that the sucrose solution contained 1 µM reserpine to block vesicular uptake of substrates. Synaptosomal preparations were incubated to steady state with 9 nM [$^3$H]1-methyl-4-phenylpyridinium ([$^3$H]$MPP^+$) (60 min, 25° C.) in Krebs-phosphate uptake assay buffer containing 1 µM reserpine to block vesicular uptake of substrates and 100 nM citalopram and 100 nM desipramine to block uptake of [$^3$H]$MPP^+$ by SERT and NET. Subsequently, 850 µL of synaptosomes preloaded with [$^3$H]$MPP^+$ were added to polystyrene test tubes that contained 150 µL of test compound in assay buffer containing 1 mg/mL BSA. After 30 minutes at 25° C., the release reaction was terminated by rapid vacuum filtration as described for uptake inhibition assays. Nonspecific values were measured by incubations in the presence of 10 µM tyramine. The retained tritium was quantified as described for uptake inhibition assays. The effect of compounds on DAT-mediated [$^3$H]$MPP^+$ release was determined in the absence and presence of 100 nM D-amphetamine. The ability of the compounds to shift D-amphetamine-induced DAT-mediated [$^3$H]$MPP^+$ release, using blocking concentrations about 25-times greater than the corresponding $EC_{50}$ for DAT uptake inhibition, were then determined. Dose-response curves were generated using eight concentrations of test drug. Following are the definitions of the parameters used in calculating the release dose-response curves: Total Binding (TB)=cpm in the absence of any drug; Nonspecific Binding (NS)=cpm in the presence of 10 µM tyramine; Maximal Release (MR)=TB-NS; Specific Release (SR)= (cpm in the presence of drug)-NS; % MAX Release=100-SR/MR*100.

The data from three experiments, expressed as % MAX Release, were then fit to a dose-response curve equation: $Y=E_{max}\times([D]/([D]+EC_{50})$ for the best fit estimates of the $E_{max}$ and $EC_{50}$ using either KaleidaGraph version 3.6.4 or MLAB-PC (Nightingale et al., *J. Pharmacol. Exp. Ther.* 314, 906-915 (2005)). In some cases, dose response curves were fit to a two-component equation: $Y=E_{max1}\times([D]/([D]+EC_{50}-1)+E_{max2}\times([D]/([D]+EC_{50}-2)$. Statistical significance of the one-site versus two-site fits was based on F-test results. In "shift" experiments, a substrate dose-response curve was generated in the absence and presence of a test drug. Apparent $K_e$ values were calculated according to the equation: [Test Drug]/($EC_{50-2}/EC_{50-1}-1$), where $EC_{50-2}$ is the $EC_{50}$ value in the presence of the test drug and $EC_{50-1}$ is the value in the absence of the uptake inhibitor. The effect of selected compounds on D-amphetamine-induced dopamine transporter-mediated [$^3$H]$MPP^+$ release is given in Table 5. The compound number in Table 5 corresponds to the respective compound number given in Table 1 and in the Examples.

TABLE 5

| Compd # | Compd Concentration (nM) | D-Amphetamine $EC_{50}$ (nM ± SD) | D-Amphetamine Emax (% ± SD) | Ke App (nM) |
|---|---|---|---|---|
| NA | none | 6.4 ± 1.2 | 104 ± 4 | — |
| 10 | 125 | 7.1 ± 0.9 | 103 ± 3 | 1140 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

7. Screening Methods

All of the test compounds were synthesized as described herein. Next, 8-point dose-response curves were generated for each compound (1-20,000 nM) in the [$^3$H]DA uptake assay. The data from three experiments were pooled and fit to a dose-response curve equation (using KaleidaGraph; Synergy Software, Reading, Pa.) to yield an $E_{max}$ and $IC_{50}$ value. Compounds were then selected for further evaluation only if they had an $IC_{50} \leq 20$ nM (high potency) and an $E_{max} \leq 70\%$ (partial efficacy). Compounds that displayed properties of full-efficacy inhibitors of [$^3$H]DA uptake were not tested further. A subset of potent partial inhibitors was then tested for dose-response effects in the [$^3$H]NE and [$^3$H]5-HT uptake inhibition assays. In addition, these same compounds were tested for their ability to alter DAT-mediated release of [$^3$H]MPP$^+$ in the absence and presence of 100 nM d-amphetamine. Selected compounds were also tested for their ability to inhibit [$^3$H]WIN35428 binding to rat caudate DAT.

8. Testing of Compounds in Animal Models

The antidepressant efficacy of compounds of the present invention can be evaluated using the forced swimming test (FST) (Porsolt et al., Nature 266, 730-732 (1997)) and by the mouse tail suspension model (TST) (Stern et al., Psychopharmacology 85, 367-370 (1985)).

9. Initial Screen of Compounds

Figure 1B:
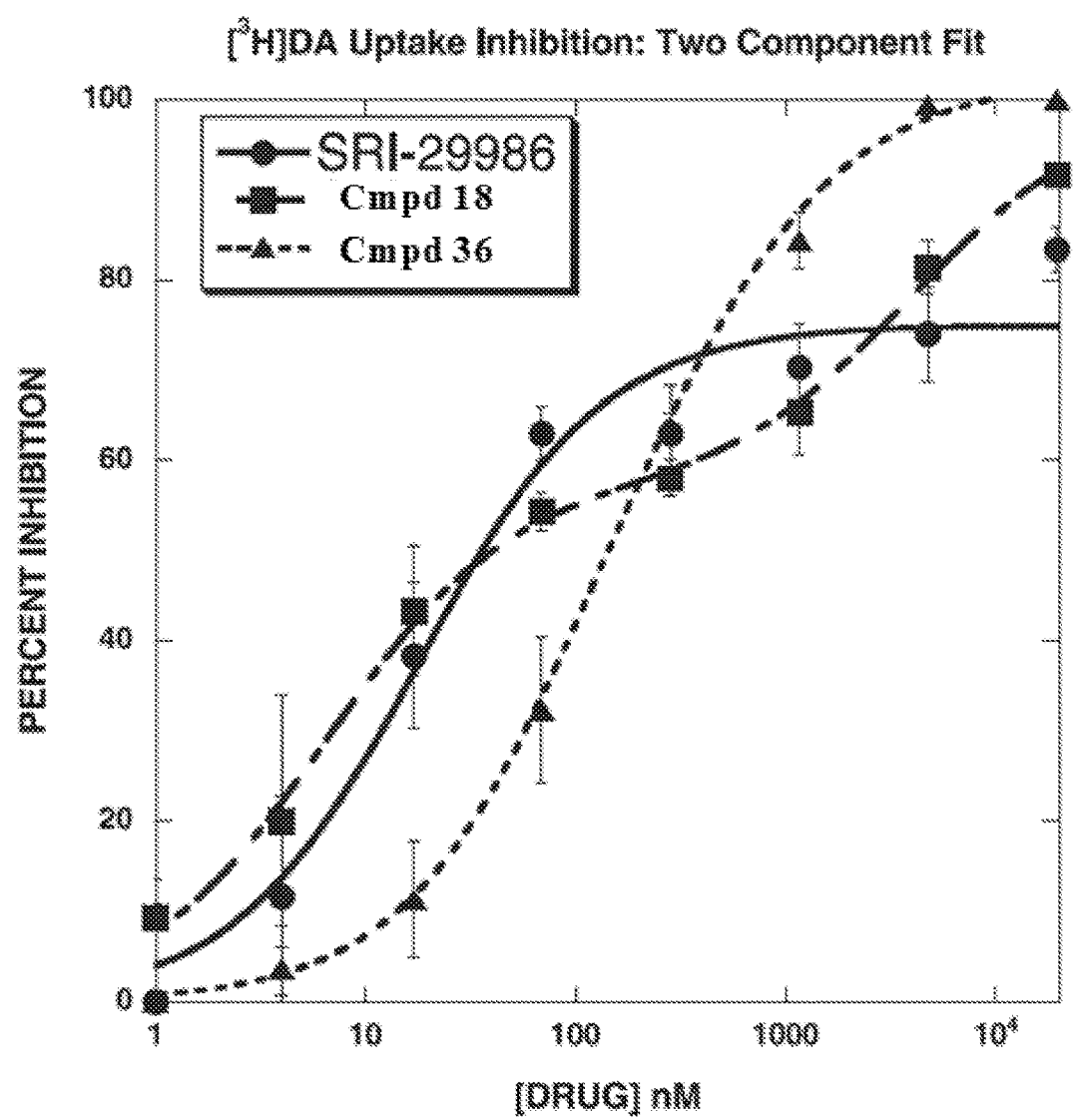

Compounds were first evaluated in the [$^3$H]DA uptake inhibition assay. Some agents acted as full-efficacy [$^3$H]DA uptake inhibitors (for example, see compound 36, Table 6 and FIG. 1A). A large set of agents also acted as partial inhibitors when the dose-response curves were fit to the one-component equation (for example, see SRI-29986). However, upon visual inspection, it is clear that whereas SRI-29986 dose-response curve is well described by a one-component equation, the compound 18 dose-response curve is not. Fitting the same three dose-response curves to a two-component equation led to a highly significant improvement in the goodness-of-fit for compound 18, but not the other two agents (FIG. 1B, Table 7). Without wishing to be bound by theory, these data illustrate that the initial set of compounds binned into three groups of [$^3$H]DA uptake inhibitors: (1) apparent full-efficacy one-component agents; (2) apparent full-efficacy agents; and (3) partial-efficacy agents. Further studies were thus focused on partial-efficacy agents. Interestingly, preliminary experiments suggest that some of the apparent full-efficacy one-component agents may also act as allosteric modulators (data not shown).

TABLE 6

| No. | SRI No. | Structure |
|---|---|---|
| — | SRI-29070 | |
| — | SRI-29072 | |
| — | SRI-29153 | |
| — | SRI-29155 | |

TABLE 6-continued

| No. | SRI No. | Structure |
|---|---|---|
| — | SRI-29212 | |
| — | SRI-29213 | |
| — | SRI-29338 | |
| — | SRI-29554 | |
| — | SRI-29574 | |
| 50 | SRI-29577 | 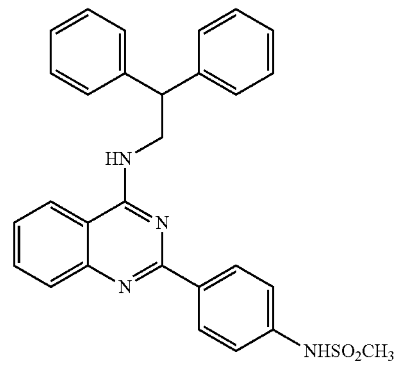 |
| — | SRI-29776 | |
| — | SRI-29779 | |

TABLE 6-continued

| No. | SRI No. | Structure |
|---|---|---|
| 51 | SRI-29786 | 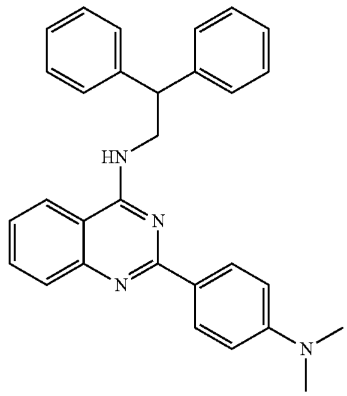 [SMILES: CN(C)c1ccc(-c2nc(NCC(c3ccccc3)c3ccccc3)c3ccccc3n2)cc1] |
| — | SRI-29982 | |
| — | SRI-29983 | |
| — | SRI-29986 | |
| — | SRI-29991 | |
| 4 | SRI-30504 | |
| — | SRI-30507 | |
| — | SRI-30508 | |

TABLE 6-continued

| No. | SRI No. | Structure |
|---|---|---|
| — | SRI-30513 | |
| — | SRI-20517 | |
| — | SRI-30522 | |
| 10 | SRI-30524 | 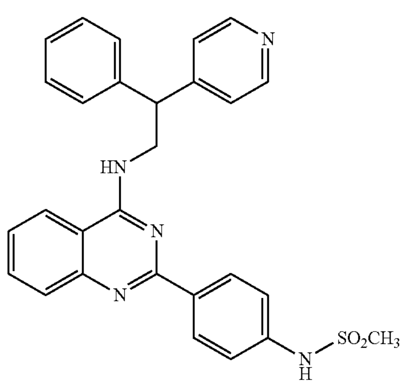 [SMILES: CS(=O)(=O)Nc1ccc(-c2nc(NCC(c3ccccc3)c3ccncc3)c3ccccc3n2)cc1] |

TABLE 6-continued

| No. | SRI No. | Structure |
|---|---|---|
| — | SRI-30810 | |
| — | SRI-30826 | |
| — | SRI-30827 | |
| 52 | SRI-30828 | |

TABLE 6-continued
| No. | SRI No. | Structure |
|---|---|---|
| 18 | SRI-30835 | 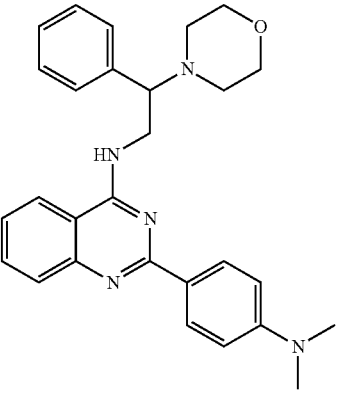 [SMILES: CN(C)c1ccc(-c2nc(NCC(c3ccccc3)N3CCOCC3)c3ccccc3n2)cc1] |
| — | SRI-30946 | 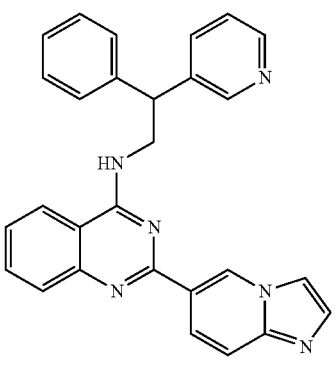 [SMILES: c1ccc(C(CNc2nc(-c3ccc4nccn4c3)nc3ccccc23)c2cccnc2)cc1] |
| — | SRI-31034 | 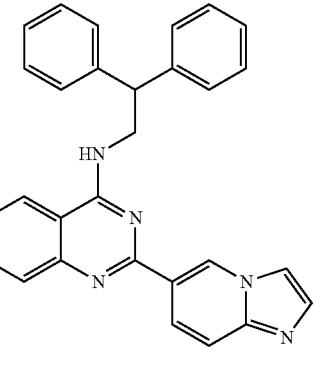 |
| 29 | SRI-31039 | 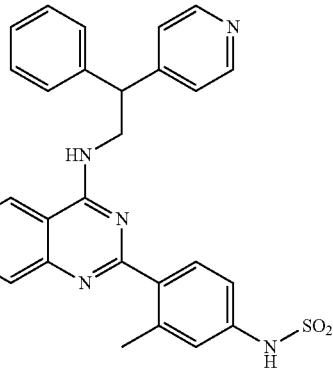 |
TABLE 6-continued
| No. | SRI No. | Structure |
|---|---|---|
| — | SRI-31040 | 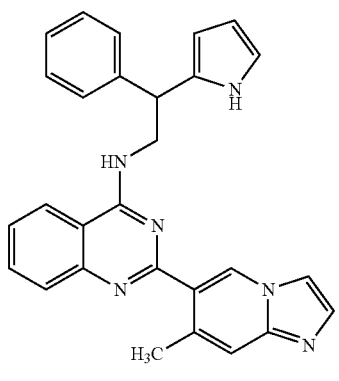 [SMILES: Cc1cc2nccn2cc1-c1nc(NCC(c2ccccc2)c2ccc[nH]2)c2ccccc2n1] |
| 53 | SRI-31043 | 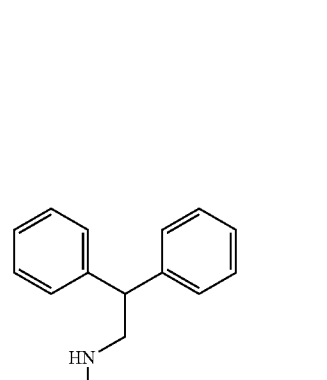 |
| — | SRI-31142 | 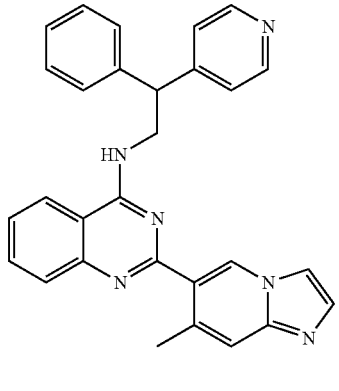 [SMILES: Cc1cc2nccn2cc1-c1nc(NCC(c2ccccc2)c2ccncc2)c2ccccc2n1] |

TABLE 6-continued

| No. | SRI No. | Structure |
|-----|---------|-----------|
| —   | SRI-31143 | 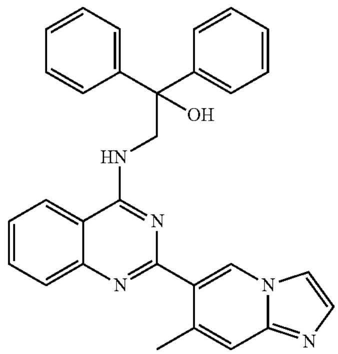 [SMILES: Cc1cc2nccn2cc1-c1nc(NCC(O)(c2ccccc2)c2ccccc2)c2ccccc2n1] |
| 36  | SRI-31335 | 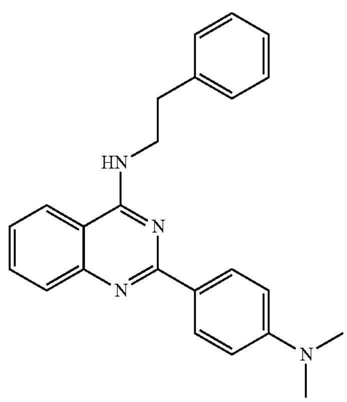 [SMILES: CN(C)c1ccc(-c2nc(NCCc3ccccc3)c3ccccc3n2)cc1] |

Figure 2A:
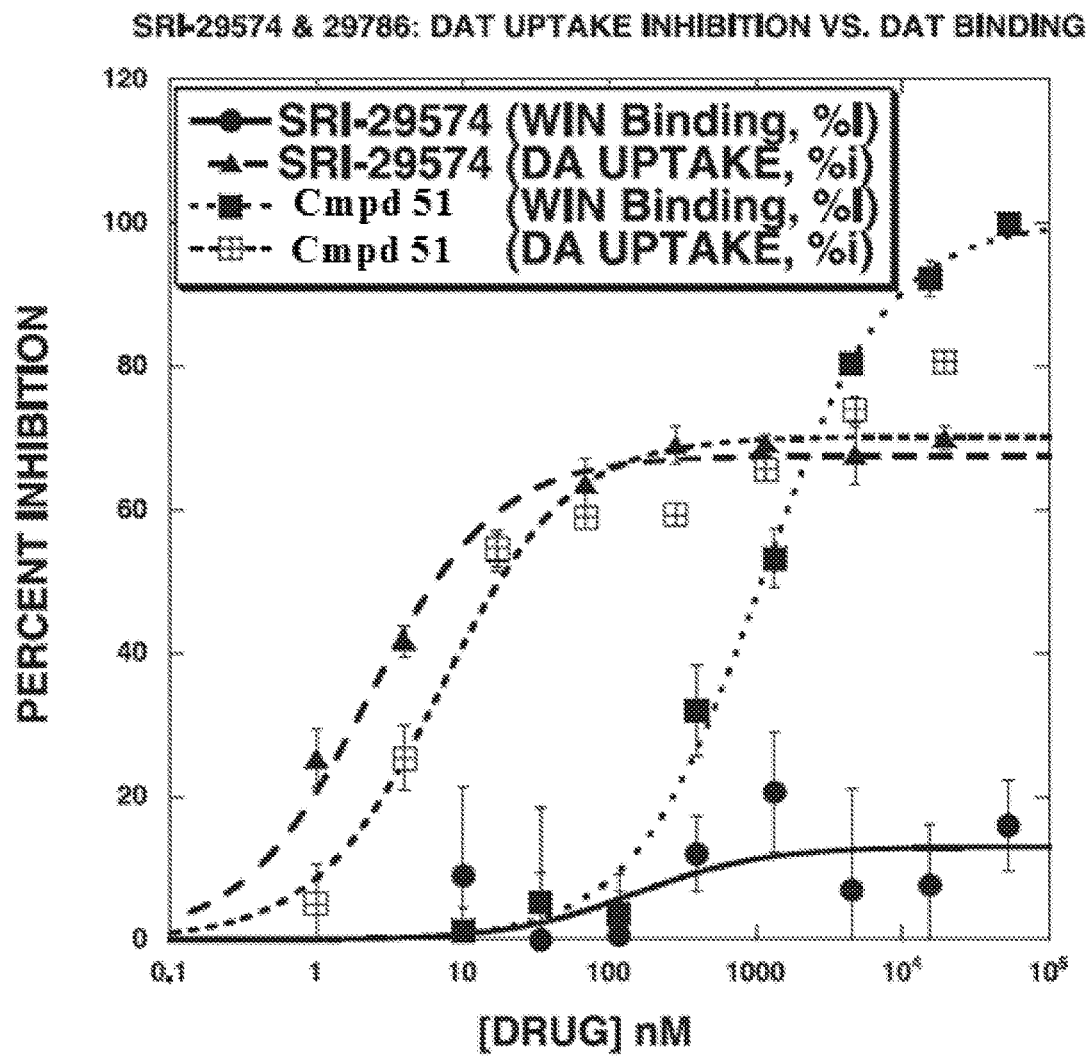
FIG. 2A shows representative data comparing the inhibition of [$^3$H]WIN35428 binding versus [$^3$H]DA uptake by compound 51.
Figure 2B:
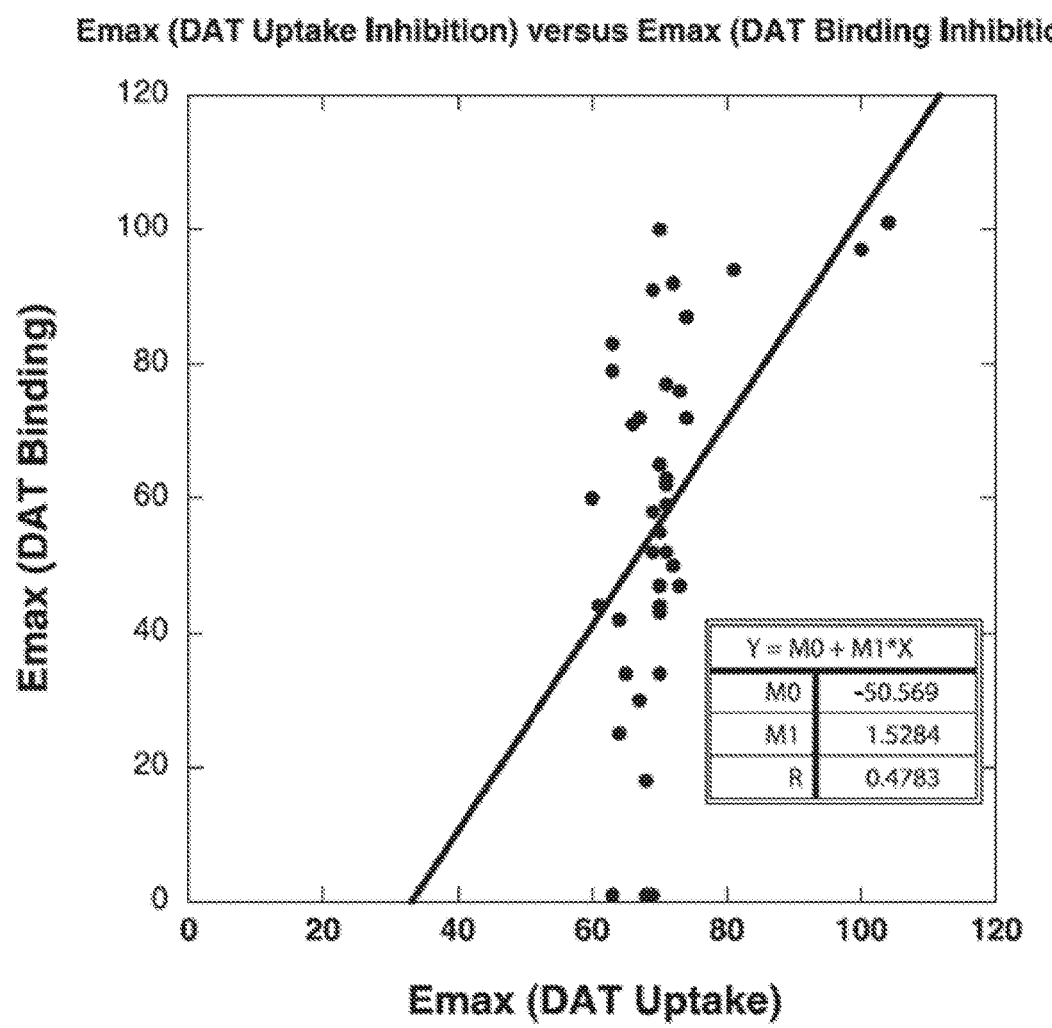
FIG. 2B shows a representative correlation plot of DAT uptake $E_{max}$ versus DAT binding $E_{max}$ for compounds shown in Table 6 herein below.

10. Evaluation of Test Agents for Inhibition of DAT<SERT, and NET Uptake and DAT Binding All agents tested (see Table 8) were partial inhibitors of DAT, SERT, and NET uptake, though in general the efficacy was lower at SERT than at NET and DAT. Although many of the test agents had similar $IC_{50}$ values for BAT uptake inhibition, in general the order of potency was DAT>SERT>NET. Another striking aspect of the data set was that most compounds were ~3 orders of magnitude less potent in inhibiting [$^3$H]WIN35428 binding to DAT than in blocking uptake of [$^3$H]DA. This is illustrated in FIG. 2A for two compounds. SRI-29574 partially inhibited DAT uptake ($IC_{50}$=2.3±0.4 nM) while being inactive in inhibiting DAT binding. In contrast, compound 51 partially inhibited DAT uptake ($IC_{50}$=7.1±2.2 nM) but also inhibited DAT binding, with full efficacy and an $IC_{50}$ value (1100±10 nM) 155-fold weaker than the $IC_{50}$ for inhibition of DAT uptake. Overall, only 5 of the 26 compounds were full efficacy inhibitors of DAT binding, and in most cases the agents were much less potent at DAT binding inhibition than at DAT uptake inhibition. In contrast, the prototypical DAT blockers GBR12935 and cocaine displayed similar potency and efficacy in both assays. There was no significant correlation between the $E_{max}$ values observed in the DAT uptake and binding assays (FIG. 2B).

TABLE 7

| No. | One-Site $IC_{50}$ (nM) | One-Site $E_{max}$ (% I) | Sum-of-Squares One-Site Fit | F Test |
|---|---|---|---|---|
| SRI-29986 | 18 ± 4 | 75 ± 3 | 175 | 0 |
| 36 | 156 ± 12 | 100 ± 1.5 | 28.9 | 1.56 |
| 18 | 15 ± 7 | 75 ± 5 | 677 | 140* |

| No. | Two-Site $IC_{50-1}$ (nM) | Two-Site $E_{max-1}$ (% I) | Two-Site $IC_{50-2}$ (nM) | Two-Site $E_{max-2}$ (% I) | Sum-of-Squares Two-Site Fit |
|---|---|---|---|---|---|
| SRI-29986 | $18 \times 10^5 \pm 1.7 \times 10^5$ | $37 \times 10^8 \pm 2.7 \times 10^8$ | $18 \times 10^5 \pm 1 \times 10^5$ | $37 \times 10^8 \pm 0.7 \times 10^8$ | 175 |
| 36 | 99 ± 63 | 76 ± 54 | 564 ± 1177 | 27 ± 53 | 19.0 |
| 18 | 6 ± 0.9 | 57 ± 2 | 4000 ± 1330 | 42 ± 4 | 14.2 |

*P < 0.001 vs. one-component fit (F test).

TABLE 8

Summary of results obtained for the 36 partial-efficacy DAT uptake blockers
Dose-response curves for each indicated agent were generated as described in *Materials and Methods*
for DAT, NET, and SERT uptake inhibition and DAT binding. Each value is the mean ± S.D.; n = 3.

| Drug | DAT Uptake IC$_{50}$ nM | DAT Uptake E$_{max}$ % | NET Uptake IC$_{50}$ nM | NET Uptake E$_{max}$ % | SERT Uptake IC$_{50}$ nM | SERT Uptake E$_{max}$ % | DAT Binding IC$_{50}$ nM | DAT Binding E$_{max}$ % | 5-HT/DA IC$_{50}$ (Uptake) | NE/DA IC$_{50}$ (Uptake) |
|---|---|---|---|---|---|---|---|---|---|---|
| SRI-29070 | 174 ± 58 | 66 ± 4 | 1740 ± 1150 | 64 ± 10 | 699 ± 164 | 48 ± 3 | 1.8 ± 0.4 | 71 ± 4 | 4 | 10 |
| SRI-29072 | 212 ± 49 | 71 ± 3 | 5850 ± 1746 | 62 ± 5 | 6382 ± 2636 | 56 ± 9 | 2.7 ± 0.3 | 77 ± 2 | 30 | 28 |
| SRI-29153 | 20 ± 1 | 73 ± 1 | 181 ± 46 | 73 ± 4 | 37 ± 18 | 55 ± 5 | 1.7 ± 0.2 | 76 ± 2 | 1.9 | 9 |
| SRI-29155 | 10 ± 1.0 | 74 ± 1 | 290 ± 52 | 70 ± 3 | 68 ± 13 | 54 ± 2 | 0.9 ± 0.2 | 87 ± 4 | 6.8 | 29 |
| SRI-29212 | 672 ± 204 | 67 ± 4 | 8126 ± 2273 | 64 ± 5 | 3805 ± 1645 | 50 ± 7 | 2.2 ± 0.5 | 72 ± 4 | 5.7 | 12 |
| SRI-29213 | 16 ± 4 | 81 ± 3 | 346 ± 59 | 77 ± 3 | 89 ± 51 | 43 ± 4 | 0.2 ± 0.0 | 94 ± 2 | 5.6 | 22 |
| SRI-29338 | 9.0 ± 1.5 | 71 ± 2 | 204 ± 47 | 62 ± 3 | 56 ± 21 | 52 ± 3 | 1.18 ± 0.93 | 63 ± 4 | 6 | 23 |
| SRI-29554 | 11 ± 1 | 71 ± 1 | 179 ± 27 | 78 ± 2 | 57 ± 18 | 60 ± 3 | 0.98 ± 0.46 | 59 ± 6 | 5 | 16 |
| SRI-29574 | 2.3 ± 0.4 | 68 ± 2 | 52 ± 15 | 72 ± 4 | 23 ± 5 | 52 ± 2 | Inactive | Inactive | 10 | 23 |
| SRI-29577 | 4.4 ± 0.8 | 70 ± 2 | 90 ± 15 | 71 ± 2 | 20 ± 5 | 56 ± 2 | 3.4 ± 1.2 | 65 ± 6 | 4.6 | 20 |
| SRI-29776 | 19 ± 4 | 69 ± 2 | 229 ± 43 | 71 ± 3 | 106 ± 19 | 61 ± 2 | 6.09 ± 0.97 | 58 ± 3 | 6 | 12 |
| SRI-29779 | 7.3 ± 2.2 | 63 ± 3 | 147 ± 63 | 71 ± 6 | 42 ± 12 | 51 ± 2 | 1.2 ± 0.2 | 83 ± 3 | 5.8 | 20 |
| SRI-29786 | 7.1 ± 2.2 | 70 ± 3 | 143 ± 61 | 68 ± 7 | 49 ± 27 | 44 ± 4 | 1.1 ± 0.1 | 100 ± 3 | 6.9 | 20 |
| SRI-29982 | 13 ± 2 | 73 ± 2 | 259 ± 41 | 71 ± 2 | 54 ± 7 | 51 ± 1 | 2.46 ± 1.21 | 47 ± 6 | 4 | 20 |
| SRI-29983 | 11 ± 2 | 70 ± 2 | 203 ± 79 | 73 ± 6 | 35 ± 9 | 57 ± 2 | 1.29 ± 0.34 | 55 ± 3 | 3 | 19 |
| SRI-29991 | 2.1 ± 0.3 | 68 ± 1 | 63 ± 9 | 69 ± 2 | 4.7 ± 0.6 | 51 ± 1 | 1.22 ± 1.12 | 18 ± 4 | 2 | 30 |
| SRI-30503 | 9.2 ± 1.2 | 70 ± 1 | 98 ± 23 | 65 ± 3 | 16 ± 5 | 55 ± 2 | 0.67 ± 0.37 | 34 ± 4 | 2 | 11 |
| SRI-30504 | 11 ± 2 | 70 ± 2 | 426 ± 49 | 70 ± 2 | 50 ± 14 | 55 ± 3 | 0.97 ± 0.65 | 47 ± 7 | 5 | 39 |
| SRI-30507 | 18 ± 3 | 71 ± 2 | 132 ± 16 | 77 ± 2 | 28 ± 6 | 54 ± 2 | 4.80 ± 1.81 | 62 ± 7 | 2 | 7 |
| SRI-30508 | 9.3 ± 1.1 | 65 ± 1 | 69 ± 18 | 76 ± 9 | 3.9 ± 0.4 | 56 ± 1 | 0.15 ± 0.09 | 34 ± 3 | 0.4 | 8 |
| SRI-30513 | 12 ± 2 | 72 ± 2 | 153 ± 55 | 65 ± 4 | 83 ± 28 | 59 ± 4 | 2.97 ± 1.03 | 50 ± 4 | 7 | 13 |
| SRI-30517 | 6.0 ± 0.7 | 70 ± 1 | 95 ± 12 | 70 ± 2 | 23 ± 3 | 54 ± 1 | 0.16 ± 0.08 | 43 ± 4 | 4 | 16 |
| SRI-30522 | 8.8 ± 1.1 | 63 ± 1 | 86 ± 55 | 40 ± 5 | 13 ± 6 | 35 ± 3 | Inactive | Inactive | 1 | 10 |
| SRI-30524 | 4.8 ± 0.6 | 71 ± 1 | 44 ± 6 | 76 ± 2 | 8.7 ± 0.9 | 56 ± 1 | 2.36 ± 1.17 | 52 ± 6 | 2 | 9 |
| SRI-30810 | 5.6 ± 0.8 | 64 ± 1 | 60 ± 10 | 69 ± 2 | 11 ± 3 | 51 ± 2 | 0.82 ± 0.36 | 25 ± 2 | 2 | 11 |
| SRI-30826 | 6.1 ± 1 | 64 ± 2 | 88 ± 15 | 81 ± 2 | 18 ± 4 | 56 ± 2 | 1.28 ± 0.40 | 42 ± 3 | 3 | 14 |
| SRI-30827 | 0.5 ± 0.1 | 63 ± 2 | 21 ± 7 | 67 ± 3 | 3.2 ± 0.9 | 58 ± 3 | 1.99 ± 0.33 | 79 ± 3 | 6 | 42 |
| SRI-30828 | 8.9 ± 1.6 | 60 ± 2 | 144 ± 30 | 65 ± 3 | 20 ± 5 | 50 ± 2 | 2.61 ± 1.14 | 60 ± 7 | 2 | 16 |
| SRI-30837 | 11 ± 1 | 61 ± 1 | 300 ± 56 | 75 ± 3 | 67 ± 8 | 55 ± 1 | 1.70 ± 0.62 | 44 ± 4 | 6 | 27 |
| SRI-30946 | 21 ± 3 | 70 ± 2 | 78 ± 17 | 75 ± 3 | 35 ± 11 | 59 ± 3 | 1.17 ± 0.32 | 44 ± 3 | 2 | 4 |
| SRI-31034 | 7.4 ± 1.1 | 69 ± 1 | 94 ± 22 | 63 ± 3 | 25 ± 7 | 49 ± 2 | Inactive | Inactive | 3 | 13 |
| SRI-31039 | 7.4 ± 2 | 74 ± 4 | 31 ± 7 | 71 ± 3 | 8.0 ± 2.8 | 58 ± 3 | 3.15 ± 1.11 | 72 ± 7 | 1 | 4 |
| SRI-31040 | 1.2 ± 0.1 | 69 ± 1 | 11 ± 4 | 70 ± 4 | 3.1 ± 0.7 | 54 ± 2 | 3.74 ± 1.10 | 91 ± 7 | 3 | 9 |
| SRI-31043 | 11 ± 1 | 67 ± 1 | 47 ± 10 | 67 ± 2 | 22 ± 5 | 51 ± 2 | 2.16 ± 0.97 | 30 ± 3 | 2 | 4 |
| SRI-31142 | 1.9 ± 0.3 | 72 ± 2 | 17 ± 4 | 61 ± 2 | 2.4 ± 0.4 | 48 ± 1 | 2.34 ± 0.45 | 92 ± 4 | 1.3 | 9 |
| SRI-31143 | 1.7 ± 0.1 | 69 ± 1 | 16 ± 5 | 69 ± 4 | 3.0 ± 0.6 | 51 ± 2 | 3.39 ± 1.99 | 52 ± 8 | 1.8 | 9 |
| Cocaine | 200 ± 19 | 100 ± 2 | 329 ± 22 | 102 ± 2 | 273 ± 24 | 98 ± 2 | 0.28 ± 0.03 | 97 ± 3 | 1.4 | 1.7 |
| GBR12935 | 1.1 ± 0.1 | 104 ± 3 | N.D. | N.D. | N.D. | N.D. | $2.0 \times 10^{-3} \pm 0.08 \times 10^{-3}$ | 101 ± 0.9 | | |

N.D., not determined.

11. Effect of Test Agents on DAT-Mediated [$^3$H]MPP$^+$ Release

The first set of release experiments determined the effect of test agents on DAT-mediated [$^3$H]MPP$^+$ release in the absence and presence of 100 nM d-amphetamine. Overall, at concentrations of <1 μM, none of the agents altered DAT-mediated [$^3$H]MPP$^+$ release in the absence or presence of 100 nM d-amphetamine (data not shown). The ability of these agents to shift d-amphetamine-induced DAT-mediated [$^3$H]MPP$^+$ release, using blocking concentrations ~25 times greater than the corresponding IC$_{50}$ for DAT uptake inhibition, were then determined. Of the 23 agents tested in this manner (see Table 9), only SRI-29574 increased EC$_{50}$ and decreased E$_{max}$. GBR12935, a competitive DAT uptake inhibitor, shifted the d-amphetamine release curve to the right in a parallel fashion without changing the E$_{max}$ value.

TABLE 9

Effect of test agents on d-amphetamine-induced, DAT-mediated [$^3$H]MPP$^+$ or [$^3$H]DA release
d-Amphetamine dose-response curves were generated in the absence and presence of each test agent as
described in Materials and Methods and illustrated in FIG. 5A. Each value is the mean ± S.D.; n = 3. The apparent $K_c$ was
calculated according to the following equation: Apparent $K_c$ = [Blocker]/(($EC_{50-2}$/$EC_{50-1}$) − 1), where $EC_{50-1}$ is the $EC_{50}$ in
the absence of blocker and $EC_{50-2}$ is the $EC_{50}$ in the presence of blocker. A negative apparent $K_c$ occurs when a
shifted $EC_{50}$ is less than the control $EC_{50}$ value.

| Blocker | $IC_{50}$ for DAT Uptake Inhibition nM | $E_{max}$ for DAT Uptake Inhibition % | Blocker Concentration nM | d-Amphetamine $EC_{50}$ | d-Amphetamine $E_{max}$ % | Apparent $K_c$ nM |
|---|---|---|---|---|---|---|
| [$^3$H]MPP$^+$ Release | | | | | | |
| None | — | — | — | 6.4 ± 1.2 | 104 ± 4 | — |
| SRI-29574 | 2 | 68 | 50 | 5.4 ± 0.6 | 103 ± 3 | −368 |
| SRI-29577 | 4 | 70 | 125 | 4.8 ± 0.4 | 102 ± 2 | −553 |
| SRI-29786 | 7 | 70 | 250 | 7.0 ± 0.5 | 101 ± 2 | 1940 |
| SRI-29779 | 7 | 63 | 250 | 7.9 ± 0.6 | 99 ± 2 | 912 |
| SRI-29155 | 10 | 74 | 250 | 9.6 ± 1.0* | 94 ± 2* | 456 |
| SRI-29213 | 16 | 81 | 500 | 9.7 ± 1.0* | 78 ± 2*** | 886 |
| SRI-29153 | 20 | 73 | 500 | 7.9 ± 0.9 | 101 ± 3 | 1820 |
| SRI-29070 | 174 | 66 | 5000 | 10.6 ± 0.7** | 98 ± 1 | 7050 |
| SRI-29072 | 212 | 71 | 5000 | 7.4 ± 1.0 | 96 ± 3 | 25830 |
| SRI-29212 | 672 | 67 | 12,500 | 7.4 ± 0.8 | 103 ± 2 | 64580 |
| SRI-29991 | 2 | 68 | 50 | 6.1 ± 0.7 | 102 ± 2 | −1070 |
| SRI-30517 | 6 | 70 | 150 | 7.0 ± 1.3 | 104 ± 4 | 1600 |
| SRI-30522 | 9 | 63 | 250 | 6.4 ± 1.1 | 105 ± 4 | N.A. |
| SRI-30524 | 5 | 71 | 125 | 7.1 ± 0.9 | 103 ± 3 | 1140 |
| SRI-30810 | 6 | 64 | 150 | 7.2 ± 1.5 | 104 ± 5 | 1200 |
| SRI-30826 | 6 | 64 | 150 | 7.0 ± 1.3 | 105 ± 4 | 1600 |
| SRI-30827 | 0.5 | 63 | 12.5 | 6.7 ± 0.9 | 104 ± 3 | 267 |
| SRI-31034 | 7 | 69 | 200 | 6.8 ± 1.5 | 104 ± 5 | 3200 |
| SRI-31040 | 1 | 69 | 25 | 9.3 ± 1.3* | 105 ± 3 | 55 |
| SRI-31142 | 2 | 72 | 50 | 7.2 ± 1.0 | 103 ± 3 | 400 |
| SRI-31143 | 2 | 67 | 50 | 6.9 ± 1.3 | 104 ± 4 | 46 |
| GBR12935 | 2 | 100 | 5 | 150 ± 25*** | 122 ± 8* | 0.22 |
| [$^3$H]DA Release | | | | | | |
| None | — | — | — | 67 ± 10 | 97 ± 3 | — |
| GBR12935 | 2 | 100 | 5 | 519 ± 95** | 91 ± 6 | 0.74 |
| SRI-29574 | 2 | 68 | 50 | 53 ± 6 | 95 ± 2 | −239 |
| SRI-29213 | 16 | 81 | 500 | 72 ± 12 | 71 ± 3*** | 6700 |

N.A., not applicable.
*P < 0.05 vs. control (Student's t test);
**P < 0.01 vs. control (Student's t test);
***P < 0.001 vs. control (Student's t test).

What is claimed is:

1. A compound selected from the group consisting of:
2-(4-(Dimethylamino)phenyl)-N-(2-phenyl-2-(pyridin-2-yl)ethyl)quinazolin-4-amine;
N-(4-(4-((2-Hydroxy-2,2-diphenylethyl)amino)quinazolin-2-yl)phenyl)methanesulfonamide;
2-((2-(4-(Dimethylamino)phenyl)quinazolin-4-yl)amino)-1,1-diphenylethanol;
N-(4-(4-((2-Cyclohexyl-2-phenylethyl)amino)quinazolin-2-yl)phenyl)methanesulfonamide;
N-(2-Cyclohexyl-2-phenylethyl)-2-(4-(dimethylamino)phenyl)quinazolin-4-amine;
N-(4-(4-((2-Phenyl-2-(pyridin-4-yl)ethyl)amino)quinazolin-2-yl)phenyl)methanesulfonamide;
2-(4-(Dimethylamino)phenyl)-N-(2-phenyl-2-(pyridin-4-yl)ethyl)quinazolin-4-amine;
2-(4-(Dimethylamino)phenyl)-N-(2-phenyl-2-(1H-pyrrol-2-yl)ethyl)quinazolin-4-amine;
N-(4-(4-((2-Phenyl-2-(1H-pyrrol-2-yl)ethyl)amino)quinazolin-2-yl)phenyl)methanesulfonamide;
2-(4-(Dimethylamino)phenyl)-N-(2-phenyl-2-(piperidin-1-yl)ethyl)quinazolin-4-amine;
2-(4-(Dimethylamino)phenyl)-N-(2-morpholino-2-phenylethyl)quinazolin-4-amine;
N-(4-(4-((2-Morpholino-2-phenylethyl)amino)quinazolin-2-yl)phenyl)methanesulfonamide;
2-(4-(Dimethylamino)phenyl)-N-(2-(4-methylpiperazin-1-yl)-2-phenylethyl)quinazolin-4-amine;
2-(4-(Dimethylamino)phenyl)-N-(2-phenyl-2-(pyridin-3-yl)ethyl)quinazolin-4-amine;
N-(4-(4-((2-Phenyl-2-(pyridin-3-yl)ethyl)amino)quinazolin-2-yl)phenyl)methanesulfonamide;
2-(4-(Dimethylamino)phenyl)-N-(2,3-diphenylpropyl)quinazolin-4-amine;
(5-(2-((2-(4-(Dimethylamino)-2-methylphenyl)quinazolin-4-yl)amino)-1-phenylethyl)-1H-pyrrol-2-yl)methanol;
N-(3-Methyl-4-(4-((2-phenyl-2-(pyridin-4-yl)ethyl)amino)quinazolin-2-yl)phenyl)methanesulfonamide;
2-(4-(Dimethylamino)phenyl)-N-(2-(pyridin-3-yl)-2-(1H-pyrrol-2-yl)ethyl)quinazolin-4-amine;
N-(2,2-Di(pyridin-4-yl)ethyl)-2-(4-(dimethylamino)phenyl)quinazolin-4-amine;
N-(4-(4-((2,2-Di(pyridin-4-yl)ethyl)amino)quinazolin-2-yl)phenyl)methanesulfonamide;
2-(4-(Dimethylamino)phenyl)-N-(2,2-diphenylpropyl)quinazolin-4-amine;
N-(4-(4-((2,2-Diphenylpropyl)amino)quinazolin-2-yl)phenyl)methanesulfonamide;
2-(4-(Dimethylamino)phenyl)-N-(1,2-diphenylethyl)quinazolin-4-amine;

2-(4-(Dimethylamino)phenyl)-N-(3-methyl-2-phenylbutyl)quinazolin-4-amine;
N-(4-(4-((3-Methyl-2-phenylbutyl)amino)quinazolin-2-yl)phenyl)methanesulfonamide;
2-(4-(Dimethylamino)phenyl)-N-(2-phenoxy-2-phenylethyl)quinazolin-4-amine;
N-(4-(4-((2-Phenoxy-2-phenylethyl)amino)quinazolin-2-yl)phenyl)methanesulfonamide; and
pharmaceutically acceptable salts thereof.

2. A compound having a structure selected from:

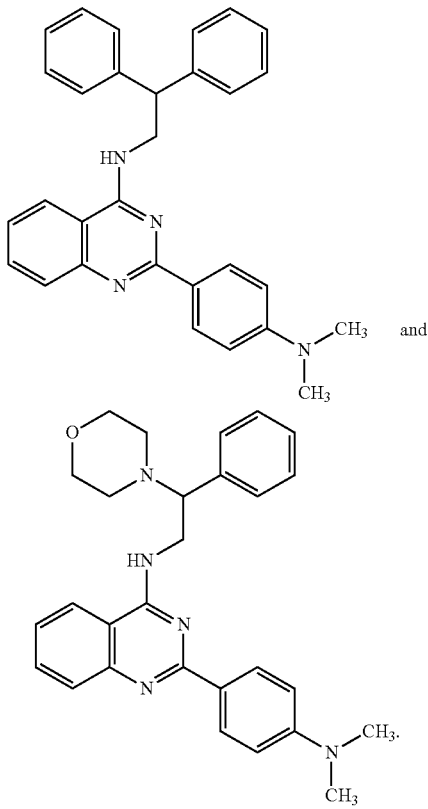

3. A pharmaceutical composition comprising a compound according to claim 2 or pharmaceutically acceptable salts thereof and a pharmaceutically acceptable carrier.

4. The compound of claim 1, selected from the group consisting of:
N-(4-(4-((2-Hydroxy-2,2-diphenylethyl)amino)quinazolin-2-yl)phenyl)methanesulfonamide;
N-(4-(4-((2-Cyclohexyl-2-phenylethyl)amino)quinazolin-2-yl)phenyl)methanesulfonamide;
N-(4-(4-((2-Phenyl-2-(pyridin-4-yl)ethyl)amino)quinazolin-2-yl)phenyl)methanesulfonamide;
N-(4-(4-((2-Phenyl-2-(1H-pyrrol-2-yl)ethyl)amino)quinazolin-2-yl)phenyl)methanesulfonamide;
N-(4-(4-((2-Morpholino-2-phenylethyl)amino)quinazolin-2-yl)phenyl)methanesulfonamide;
N-(4-(4-((2-Phenyl-2-(pyridin-3-yl)ethyl)amino)quinazolin-2-yl)phenyl)methanesulfonamide;
N-(3-Methyl-4-(4-((2-phenyl-2-(pyridin-4-yl)ethyl)amino)quinazolin-2-yl)phenyl)methanesulfonamide;
N-(4-(4-((2,2-Di(pyridin-4-yl)ethyl)amino)quinazolin-2-yl)phenyl)methanesulfonamide;
N-(4-(4-((2,2-Diphenylpropyl)amino)quinazolin-2-yl)phenyl)methanesulfonamide;
N-(4-(4-((3-Methyl-2-phenylbutyl)amino)quinazolin-2-yl)phenyl)methanesulfonamide;
N-(4-(4-((2-Phenoxy-2-phenylethyl)amino)quinazolin-2-yl)phenyl)methanesulfonamide; and
pharmaceutically acceptable salts thereof.

5. The compound of claim 1, selected from the group consisting of:
N-(4-(4-((2-Hydroxy-2,2-diphenylethyl)amino)quinazolin-2-yl)phenyl)methanesulfonamide;
N-(4-(4-((2-Phenyl-2-(pyridin-4-yl)ethyl)amino)quinazolin-2-yl)phenyl)methanesulfonamide;
N-(3-Methyl-4-(4-((2-phenyl-2-(pyridin-4-yl)ethyl)amino)quinazolin-2-yl)phenyl)methanesulfonamide; and
pharmaceutically acceptable salts thereof.

6. The compound of claim 1, selected from the group consisting of:
N-(4-(4-((2-Hydroxy-2,2-diphenylethyl)amino)quinazolin-2-yl)phenyl)methanesulfonamide; and
pharmaceutically acceptable salts thereof.

7. The compound of claim 1, selected from the group consisting of:
N-(4-(4-((2-Phenyl-2-(pyridin-4-yl)ethyl)amino)quinazolin-2-yl)phenyl)methanesulfonamide; and
pharmaceutically acceptable salts thereof.

8. The compound of claim 1, selected from the group consisting of:
N-(3-Methyl-4-(4-((2-phenyl-2-(pyridin-4-yl)ethyl)amino)quinazolin-2-yl)phenyl)methanesulfonamide; and
pharmaceutically acceptable salts thereof.

9. The compound of claim 1, selected from the group consisting of:
2-(4-(Dimethylamino)phenyl)-N-(2-phenyl-2-(pyridin-2-yl)ethyl)quinazolin-4-amine
2-((2-(4-(Dimethylamino)phenyl)quinazolin-4-yl)amino)-1,1-diphenylethanol;
N-(2-Cyclohexyl-2-phenylethyl)-2-(4-(dimethylamino)phenyl)quinazolin-4-amine;
2-(4-(Dimethylamino)phenyl)-N-(2-phenyl-2-(pyridin-4-yl)ethyl)quinazolin-4-amine;
2-(4-(Dimethylamino)phenyl)-N-(2-phenyl-2-(1H-pyrrol-2-yl)ethyl)quinazolin-4-amine;
2-(4-(Dimethylamino)phenyl)-N-(2-phenyl-2-(piperidin-1-yl)ethyl)quinazolin-4-amine;
2-(4-(Dimethylamino)phenyl)-N-(2-morpholino-2-phenylethyl)quinazolin-4-amine;
2-(4-(Dimethylamino)phenyl)-N-(2-(4-methylpiperazin-1-yl)-2-phenylethyl)quinazolin-4-amine;
2-(4-(Dimethylamino)phenyl)-N-(2-phenyl-2-(pyridin-3-yl)ethyl)quinazolin-4-amine;
2-(4-(Dimethylamino)phenyl)-N-(2,3-diphenylpropyl)quinazolin-4-amine;
(5-(2-((2-(4-(Dimethylamino)-2-methylphenyl)quinazolin-4-yl)amino)-1-phenylethyl)-1H-pyrrol-2-yl)methanol;
2-(4-(Dimethylamino)phenyl)-N-(2-(pyridin-3-yl)-2-(1H-pyrrol-2-yl)ethyl)quinazolin-4-amine;
N-(2,2-Di(pyridin-4-yl)ethyl)-2-(4-(dimethylamino)phenyl)quinazolin-4-amine;
2-(4-(Dimethylamino)phenyl)-N-(2,2-diphenylpropyl)quinazolin-4-amine;
2-(4-(Dimethylamino)phenyl)-N-(1,2-diphenylethyl)quinazolin-4-amine;
2-(4-(Dimethylamino)phenyl)-N-(3-methyl-2-phenylbutyl)quinazolin-4-amine;
2-(4-(Dimethylamino)phenyl)-N-(2-phenoxy-2-phenylethyl)quinazolin-4-amine; and
pharmaceutically acceptable salts thereof.

10. A pharmaceutical composition comprising a compound according to claim 1 or pharmaceutically acceptable salts thereof and a pharmaceutically acceptable carrier.
11. The compound of claim 2, wherein the compound has a structure:
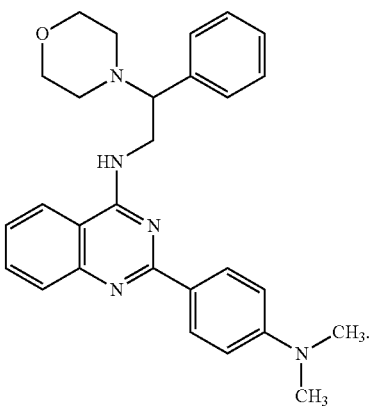 [SMILES: CN(C)c1ccc(-c2nc(NCC(c3ccccc3)N3CCOCC3)c3ccccc3n2)cc1]
12. The compound of claim 2, wherein the compound has a structure:
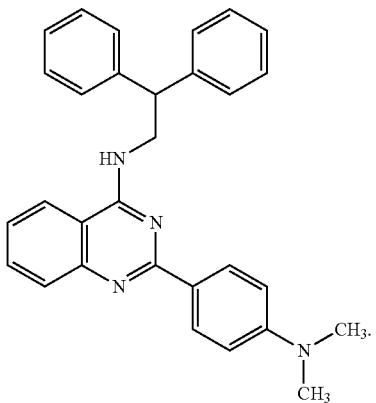 [SMILES: CN(C)c1ccc(-c2nc(NCC(c3ccccc3)c3ccccc3)c3ccccc3n2)cc1]
* * * * *